US011883103B2

(12) United States Patent
Toth et al.

(10) Patent No.: US 11,883,103 B2
(45) Date of Patent: Jan. 30, 2024

(54) ANS ASSESSMENT SYSTEMS, KITS, AND METHODS

(71) Applicant: Autonomix Medical, Inc., Ivyland, PA (US)

(72) Inventors: Landy Toth, Doylestown, PA (US); Robert S. Schwartz, Inver Grove Heights, MN (US)

(73) Assignee: Autonomix Medical, Inc., Ivyland, PA (US)

( * ) Notice: Subject to any disclaimer, the term of this patent is extended or adjusted under 35 U.S.C. 154(b) by 433 days.

(21) Appl. No.: 17/005,600

(22) Filed: Aug. 28, 2020

(65) Prior Publication Data
US 2020/0390328 A1 Dec. 17, 2020

Related U.S. Application Data

(63) Continuation of application No. 15/503,180, filed as application No. PCT/US2015/044235 on Aug. 7, 2015, now Pat. No. 10,791,924.
(Continued)

(51) Int. Cl.
*A61B 5/00* (2006.01)
*A61B 3/113* (2006.01)
(Continued)

(52) U.S. Cl.
CPC ............ *A61B 3/113* (2013.01); *A61B 3/0025* (2013.01); *A61B 3/0033* (2013.01);
(Continued)

(58) Field of Classification Search
CPC ..... A61B 3/113; A61B 3/0025; A61B 3/0033; A61B 3/0041; A61B 3/14; A61B 5/0024;
(Continued)

(56) References Cited

U.S. PATENT DOCUMENTS 5,617,872 A 4/1997 Scinto et al.
5,737,061 A * 4/1998 Sinclair .................. A61B 3/112
514/54

(Continued)

FOREIGN PATENT DOCUMENTS

AU 2010207062 B2 5/2015
AU 2014233285 A1 9/2015
(Continued)

OTHER PUBLICATIONS

F. Bremner, "Pupil Evaluation as a Test for Autonomic Disorders," Clinical Autonomic Research, 2009, pp. 88-101, vol. 19, No. 2.
(Continued)

*Primary Examiner* — May A Abouelela
(74) *Attorney, Agent, or Firm* — Ryan, Mason & Lewis, LLP

(57) ABSTRACT

Systems, devices, methods, and kits for monitoring one or more physiologic and/or physical signals from a subject are disclosed. A system including a head mounted display to monitor one or more physiologic signals from the face or head of the subject is disclosed. A method for analyzing an ocular parameter of the subject to determine a sympathetic and a parasympathetic outflow thereto is disclosed.

20 Claims, 9 Drawing Sheets

Related U.S. Application Data

(60) Provisional application No. 62/060,302, filed on Oct. 6, 2014, provisional application No. 62/035,444, filed on Aug. 10, 2014.

(51) Int. Cl.

| | | |
|---|---|---|
| *A61B 5/16* | (2006.01) | |
| *A61B 5/11* | (2006.01) | |
| *A61B 5/107* | (2006.01) | |
| *A61B 90/00* | (2016.01) | |
| *A61B 3/00* | (2006.01) | |
| *A61B 3/14* | (2006.01) | |
| *A61B 5/0205* | (2006.01) | |
| *A61B 18/02* | (2006.01) | |
| *A61B 18/06* | (2006.01) | |
| *A61B 18/14* | (2006.01) | |
| *A61B 18/18* | (2006.01) | |
| *A61B 18/24* | (2006.01) | |
| *A61F 7/00* | (2006.01) | |
| *A61M 5/00* | (2006.01) | |
| *A61N 1/36* | (2006.01) | |
| *A61N 7/02* | (2006.01) | |
| *A61B 5/024* | (2006.01) | |
| *A61B 5/0533* | (2021.01) | |
| *A61B 5/08* | (2006.01) | |
| *A61B 5/145* | (2006.01) | |
| *A61B 5/1455* | (2006.01) | |
| *A61B 5/026* | (2006.01) | |
| *A61B 5/01* | (2006.01) | |
| *A61B 5/113* | (2006.01) | |
| *A61B 5/103* | (2006.01) | |
| *A61B 5/021* | (2006.01) | |
| *A61B 5/259* | (2021.01) | |
| *A61B 5/318* | (2021.01) | |
| *A61B 5/389* | (2021.01) | |
| *A61B 5/398* | (2021.01) | |
| *A61B 18/00* | (2006.01) | |

(52) U.S. Cl.
CPC ............ *A61B 3/0041* (2013.01); *A61B 3/14* (2013.01); *A61B 5/0024* (2013.01); *A61B 5/02055* (2013.01); *A61B 5/1075* (2013.01); *A61B 5/1128* (2017.08); *A61B 5/40* (2013.01); *A61B 5/486* (2013.01); *A61B 5/4884* (2013.01); *A61B 5/6803* (2013.01); *A61B 18/02* (2013.01); *A61B 18/06* (2013.01); *A61B 18/1492* (2013.01); *A61B 18/18* (2013.01); *A61B 18/1815* (2013.01); *A61B 18/24* (2013.01); *A61B 90/37* (2016.02); *A61F 7/007* (2013.01); *A61M 5/00* (2013.01); *A61N 1/36014* (2013.01); *A61N 7/02* (2013.01); *A61B 5/0051* (2013.01); *A61B 5/01* (2013.01); *A61B 5/021* (2013.01); *A61B 5/026* (2013.01); *A61B 5/0261* (2013.01); *A61B 5/02405* (2013.01); *A61B 5/0533* (2013.01); *A61B 5/0816* (2013.01); *A61B 5/1032* (2013.01); *A61B 5/1079* (2013.01); *A61B 5/1103* (2013.01); *A61B 5/1104* (2013.01); *A61B 5/1118* (2013.01); *A61B 5/1135* (2013.01); *A61B 5/14542* (2013.01); *A61B 5/14551* (2013.01); *A61B 5/165* (2013.01); *A61B 5/259* (2021.01); *A61B 5/318* (2021.01); *A61B 5/389* (2021.01); *A61B 5/398* (2021.01); *A61B 5/4035* (2013.01); *A61B 5/6814* (2013.01); *A61B 5/6833* (2013.01); *A61B 5/721* (2013.01); *A61B 5/7221* (2013.01); *A61B 5/744* (2013.01); *A61B 2018/00434* (2013.01); *A61B 2018/00577* (2013.01); *A61B 2018/0293* (2013.01); *A61B 2018/1861* (2013.01); *A61B 2090/365* (2016.02); *A61B 2090/374* (2016.02); *A61F 2007/0075* (2013.01)

(58) Field of Classification Search
CPC . A61B 5/02055; A61B 5/1075; A61B 5/1128; A61B 5/163; A61B 5/40; A61B 5/486; A61B 5/4884; A61B 5/6803; A61B 18/02; A61B 18/06; A61B 18/1492; A61B 18/18; A61B 18/1815; A61B 18/24; A61B 90/37; A61B 5/0051; A61B 5/01; A61B 5/021; A61B 5/02405; A61B 5/026; A61B 5/0261; A61B 5/0533; A61B 5/0816; A61B 5/1032; A61B 5/1079; A61B 5/1103; A61B 5/1104; A61B 5/1118; A61B 5/1135; A61B 5/14542; A61B 5/14551; A61B 5/165; A61B 5/259; A61B 5/318; A61B 5/389; A61B 5/398; A61B 5/4035; A61B 5/6814; A61B 5/6833; A61B 5/721; A61B 5/7221; A61B 5/744; A61B 2018/00434; A61B 2018/00577; A61B 2018/0293; A61B 2018/1861; A61B 2090/365; A61B 2090/374; A61B 5/16; A61F 7/007; A61F 2007/0075; A61M 5/00; A61N 1/36014; A61N 7/02; G16H 40/63; G16H 50/20; G16H 50/70
See application file for complete search history.

(56) References Cited

U.S. PATENT DOCUMENTS

| | | | | |
|---|---|---|---|---|
| 5,865,832 | A * | 2/1999 | Knopp | B23K 26/04 606/5 |
| 6,120,460 | A * | 9/2000 | Abreu | A61B 5/1455 600/405 |
| 6,466,817 | B1 | 10/2002 | Kaula et al. | |
| 6,916,096 | B2 * | 7/2005 | Eberl | G02B 21/0028 351/209 |
| 7,177,677 | B2 | 2/2007 | Kaula et al. | |
| 7,562,981 | B2 * | 7/2009 | Togino | A61B 5/165 351/223 |
| 7,865,236 | B2 | 1/2011 | Cory et al. | |
| 7,885,700 | B2 | 2/2011 | Clark et al. | |
| 8,097,926 | B2 | 1/2012 | De Graff et al. | |
| 8,320,990 | B2 | 11/2012 | Vij | |
| 8,536,667 | B2 | 9/2013 | De Graff et al. | |
| 8,690,750 | B2 | 4/2014 | Krueger | |
| 8,702,857 | B2 | 4/2014 | Venema et al. | |
| 8,706,219 | B2 | 4/2014 | Feldman et al. | |
| 8,712,549 | B2 | 4/2014 | Zdeblick et al. | |
| 9,186,060 | B2 | 11/2015 | De Graff et al. | |
| 9,295,842 | B2 | 3/2016 | Ghaffari et al. | |
| 9,326,816 | B2 | 5/2016 | Srivastava | |
| 9,339,332 | B2 | 5/2016 | Srivastava | |
| 9,629,586 | B2 | 4/2017 | Ghaffari et al. | |
| 9,655,509 | B2 * | 5/2017 | Rotenstreich | A61B 3/0091 |
| 9,662,069 | B2 | 5/2017 | De Graff et al. | |
| 9,750,421 | B2 | 9/2017 | Ghaffari et al. | |
| 9,801,557 | B2 | 10/2017 | Ghaffari et al. | |
| 9,820,673 | B2 | 11/2017 | Feldman et al. | |
| 9,931,047 | B2 | 4/2018 | Srivastava | |
| 10,034,605 | B2 * | 7/2018 | Holt | A61B 3/152 |
| 10,186,546 | B2 | 1/2019 | De Graff et al. | |
| 10,258,230 | B2 * | 4/2019 | Rotenstreich | A61B 3/0041 |
| 10,271,898 | B2 | 4/2019 | Cao et al. | |
| 10,292,610 | B2 | 5/2019 | Srivastava | |
| 10,426,545 | B2 | 10/2019 | Asirvatham et al. | |
| 10,737,123 | B2 | 8/2020 | Sullivan et al. | |
| 10,918,298 | B2 | 2/2021 | Rogers et al. | |

(56) References Cited

U.S. PATENT DOCUMENTS

| | | | |
|---|---|---|---|
| 11,058,484 B2 | 7/2021 | Asirvatham et al. | |
| 11,515,029 B2 | 11/2022 | Sullivan et al. | |
| 11,540,775 B2 | 1/2023 | Shachar et al. | |
| 2002/0024633 A1* | 2/2002 | Kim | A61B 3/112 382/117 |
| 2002/0036750 A1* | 3/2002 | Eberl | G02B 27/0093 351/207 |
| 2004/0075812 A1* | 4/2004 | Kardon | A61B 3/0058 351/215 |
| 2004/0009783 A1 | 5/2004 | Epley | |
| 2007/0091265 A1* | 4/2007 | Kardon | A61B 3/12 351/206 |
| 2007/0123794 A1 | 5/2007 | Togino | |
| 2008/0198330 A1* | 8/2008 | Taylor | A61B 3/112 351/221 |
| 2009/0147217 A1 | 6/2009 | Molnar et al. | |
| 2009/0157751 A1 | 6/2009 | Jung et al. | |
| 2009/0174865 A1 | 7/2009 | Privitera et al. | |
| 2010/0022814 A1 | 9/2010 | Labat | |
| 2010/0298895 A1 | 11/2010 | Ghaffari et al. | |
| 2011/0077546 A1 | 3/2011 | Fabian | |
| 2011/0077548 A1* | 3/2011 | Torch | A61B 5/165 600/558 |
| 2011/0170067 A1 | 7/2011 | Sato et al. | |
| 2011/0172555 A1* | 7/2011 | Kolanko | A61B 3/11 600/558 |
| 2011/0242306 A1* | 10/2011 | Bressler | A61B 3/12 382/128 |
| 2012/0017804 A1 | 1/2012 | Venema et al. | |
| 2012/0083667 A1* | 4/2012 | Isogai | A61B 3/14 600/300 |
| 2012/0157804 A1 | 6/2012 | Rogers et al. | |
| 2012/0188149 A1* | 7/2012 | Yamada | G02B 27/0176 345/8 |
| 2012/0268715 A1* | 10/2012 | Stark | A61B 5/163 351/205 |
| 2013/0245486 A1* | 9/2013 | Simon | A61B 5/4836 607/46 |
| 2013/0278899 A1 | 10/2013 | Waldorf et al. | |
| 2014/0171756 A1* | 6/2014 | Waldorf | A61B 3/032 600/301 |
| 2014/0268047 A1* | 9/2014 | Hirsh | A61B 3/112 351/246 |
| 2014/0275993 A1 | 9/2014 | Ballakur | |
| 2015/0116665 A1* | 4/2015 | Finkel | G16H 30/40 351/210 |
| 2015/0141865 A1* | 5/2015 | Nakajima | A61B 5/6803 600/558 |
| 2015/0190194 A1 | 7/2015 | Weber et al. | |
| 2015/0234206 A1* | 8/2015 | Lee | G02C 7/083 351/158 |
| 2015/0245766 A1* | 9/2015 | Rennaker | A61B 3/14 351/210 |
| 2016/0113727 A1* | 4/2016 | Tripathi | A61B 3/0033 606/107 |
| 2017/0188942 A1 | 7/2017 | Ghaffari et al. | |
| 2018/0078169 A1 | 3/2018 | Feldman et al. | |
| 2019/0069949 A1 | 3/2019 | Vrba et al. | |
| 2020/0337765 A1 | 10/2020 | Smith | |
| 2020/0375541 A1 | 12/2020 | Shachar et al. | |
| 2021/0307824 A1 | 10/2021 | Asirvatham et al. | |
| 2022/0047202 A1 | 2/2022 | Shachar et al. | |
| 2023/0057437 A1 | 2/2023 | Sullivan et al. | |

FOREIGN PATENT DOCUMENTS

| | | |
|---|---|---|
| AU | 2013230893 B2 | 12/2015 |
| AU | 2013305279 B2 | 7/2017 |
| AU | 2015358385 B2 | 9/2020 |
| CA | 2934245 A1 | 7/2015 |
| CA | 2969129 A1 | 6/2016 |
| CA | 2749024 C | 10/2016 |
| CN | 203138452 U | 8/2013 |
| CN | 102292395 B | 7/2014 |
| CN | 103284693 B | 12/2014 |
| CN | 103271766 B | 8/2015 |
| CN | 105828709 A | 8/2016 |
| CN | 106068105 A | 11/2016 |
| CN | 105120785 B | 11/2017 |
| CN | 107802341 B | 7/2020 |
| CN | 105658163 B | 8/2020 |
| CN | 111700677 A | 9/2020 |
| DK | 2389415 T3 | 11/2014 |
| EP | 1451595 B1 | 7/2009 |
| EP | 2389415 B1 | 8/2014 |
| EP | 2513953 B1 | 10/2017 |
| EP | 3038555 B1 | 7/2018 |
| EP | 2986243 B1 | 6/2020 |
| EP | 3226795 B1 | 8/2020 |
| EP | 2887900 B1 | 12/2020 |
| EP | 2967713 B1 | 12/2020 |
| EP | 3799815 A1 | 4/2021 |
| EP | 3038556 B1 | 5/2021 |
| EP | 3884897 A1 | 9/2021 |
| EP | 4144294 A1 | 3/2023 |
| EP | 23182480.6 | 10/2023 |
| ES | 2329773 T3 | 12/2009 |
| ES | 2523498 T3 | 11/2014 |
| JP | 2006509547 A | 3/2006 |
| JP | 5405706 B2 | 2/2014 |
| JP | 5681117 B2 | 3/2015 |
| JP | 5694947 B2 | 4/2015 |
| JP | 2016534842 A | 11/2016 |
| JP | 2017502752 A | 1/2017 |
| JP | 6109863 B2 | 4/2017 |
| JP | 2017148514 A | 8/2017 |
| JP | 6204616 B2 | 9/2017 |
| JP | 2017536187 A | 12/2017 |
| JP | 6574134 B2 | 9/2019 |
| KR | 101590005 B1 | 1/2016 |
| KR | 20160106582 A | 9/2016 |
| KR | 101743628 B1 | 6/2017 |
| NL | 2002442 C2 | 7/2010 |
| WO | 2001093759 A1 | 12/2001 |
| WO | 2003048789 A2 | 6/2003 |
| WO | 2004052182 A2 | 6/2004 |
| WO | 2005046464 A1 | 5/2005 |
| WO | 2006044868 A1 | 4/2006 |
| WO | 2009128563 A1 | 10/2009 |
| WO | 2010030373 A2 | 3/2010 |
| WO | 2010082993 A2 | 7/2010 |
| WO | 2010085140 A1 | 7/2010 |
| WO | 2011084450 A1 | 7/2011 |
| WO | 2011093991 A1 | 8/2011 |
| WO | 2013134479 A1 | 9/2013 |
| WO | 2014029355 A1 | 2/2014 |
| WO | 2014172398 A1 | 10/2014 |
| WO | 2015031643 A1 | 3/2015 |
| WO | 2015031648 A1 | 3/2015 |
| WO | 2015061457 A1 | 4/2015 |
| WO | PCT/US2015/044235 | 4/2015 |
| WO | 2015102951 A2 | 7/2015 |
| WO | 2015103541 A1 | 7/2015 |
| WO | 2016090175 A1 | 6/2016 |
| WO | 2020242753 A1 | 12/2020 |
| WO | 2023038682 A1 | 3/2023 |
| WO | 2023038748 A1 | 3/2023 |

OTHER PUBLICATIONS

P. Baum, "Dysfunction of Autonomic Nervous System in Childhood Obesity: A Cross-Sectional Study," PLoS One, Jan. 2013, 8 pages, vol. 8, No. 1.

D. H. McDougal et al., "Pupillary Control Pathways," The Senses: A Comprehensive Reference, 2008, pp. 521-536, vol. 1.

* cited by examiner

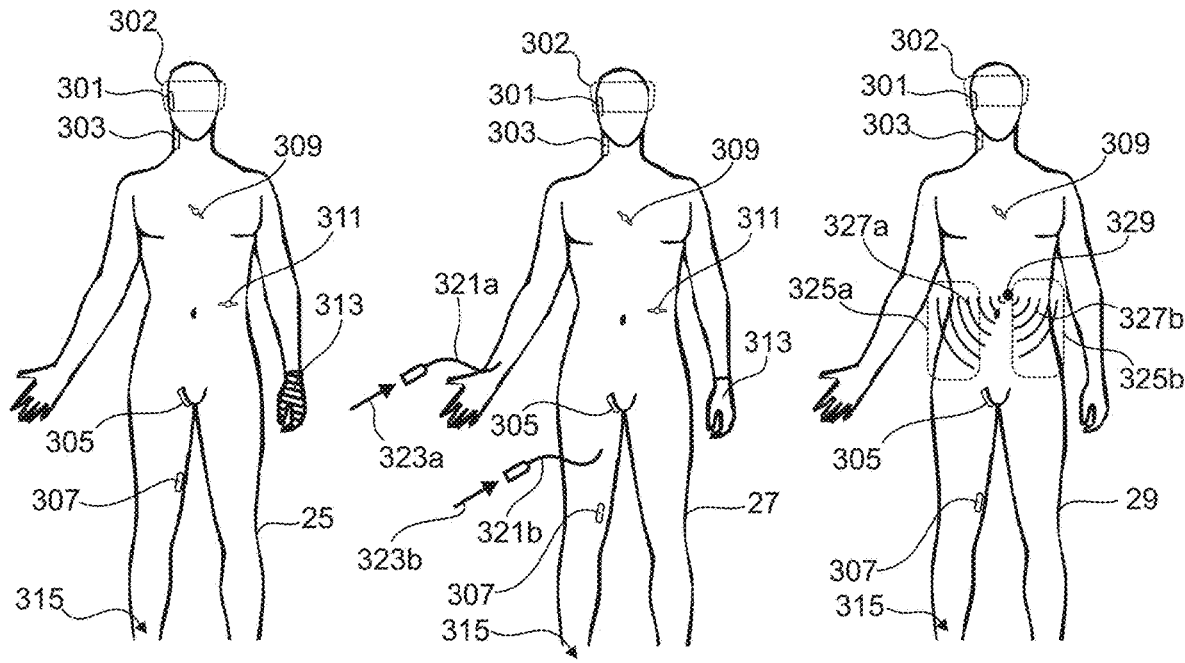
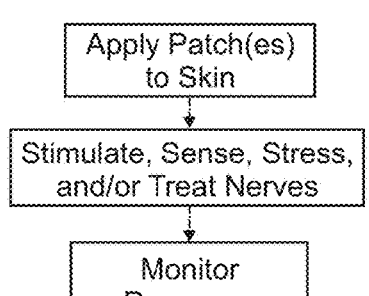
Fig 4a
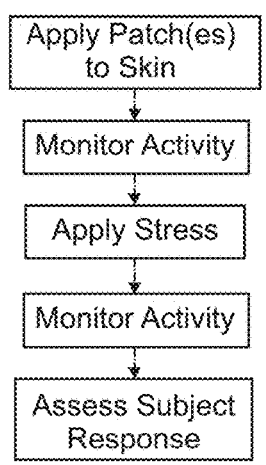
Fig 4b
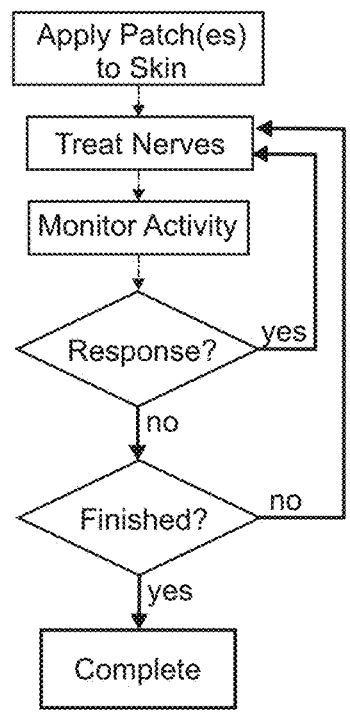
Fig 4c

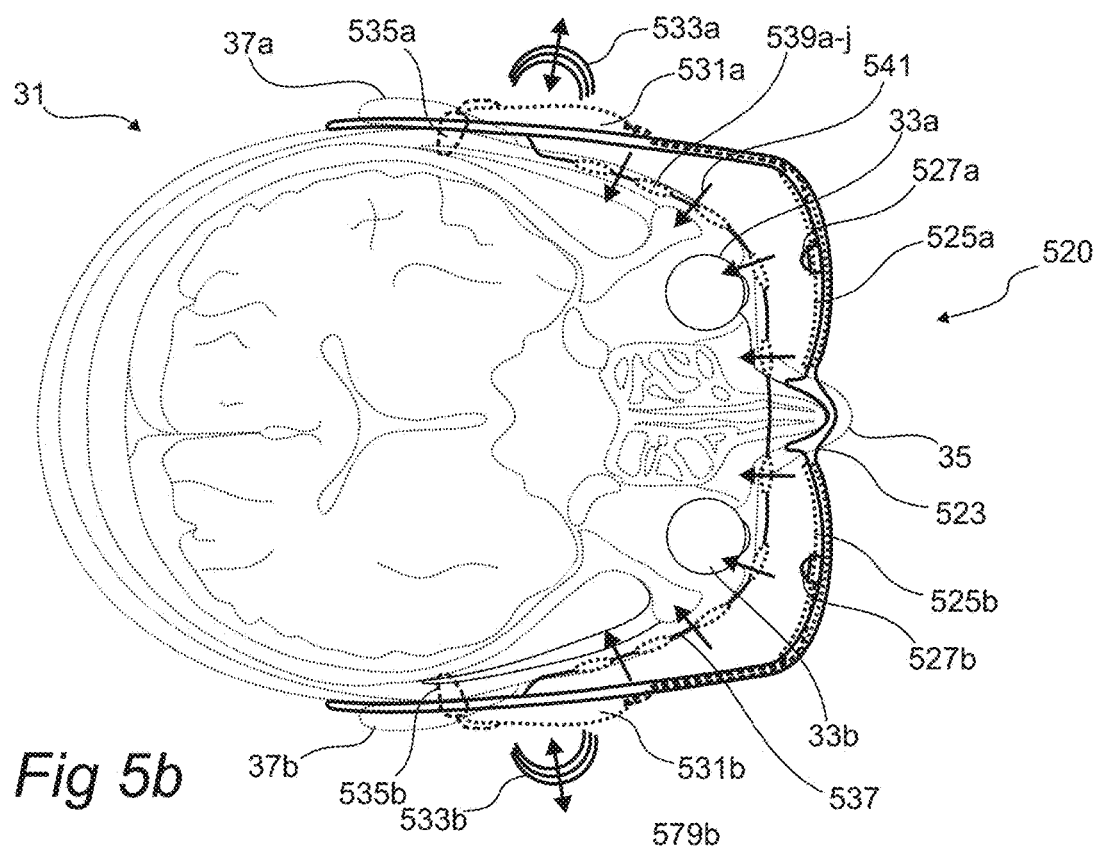

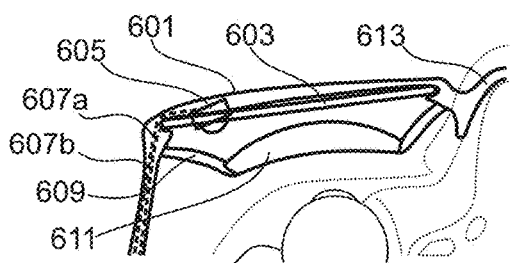
Fig 6a
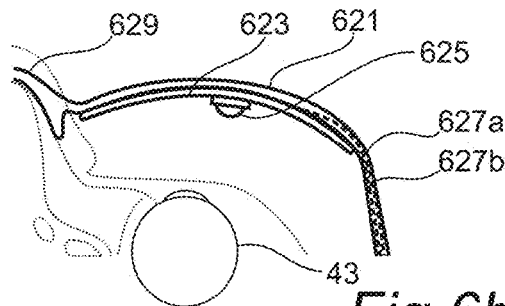
Fig 6b
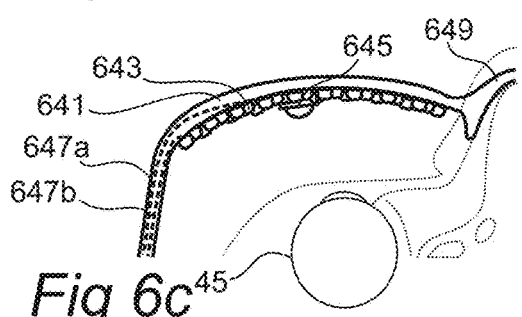
Fig 6c
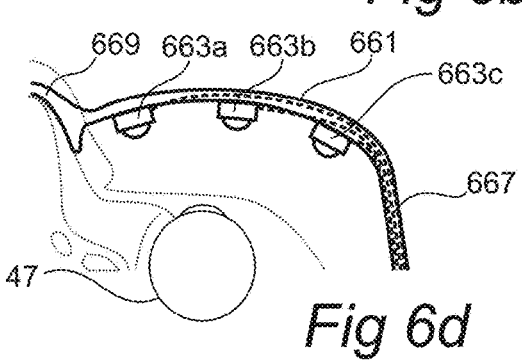
Fig 6d
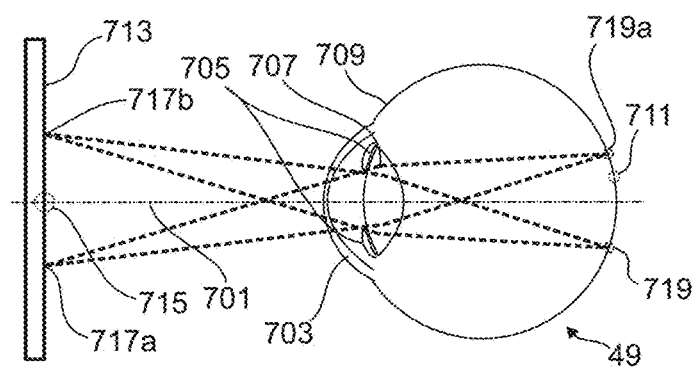
Fig 7
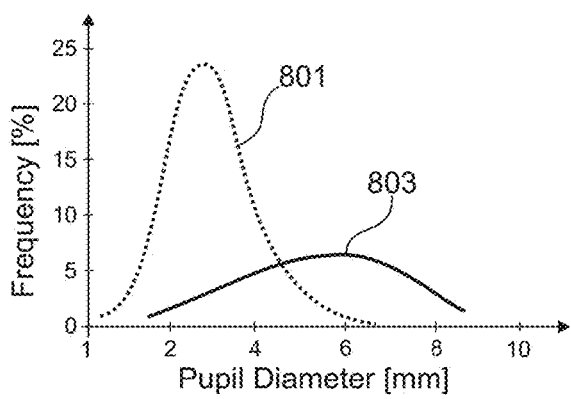
Fig 8a
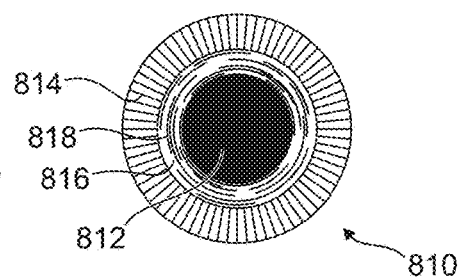
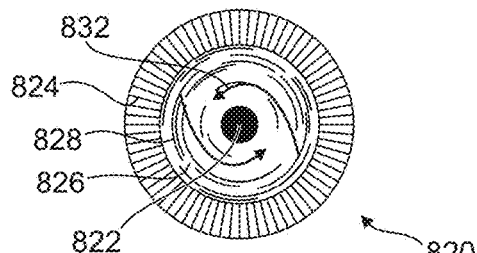
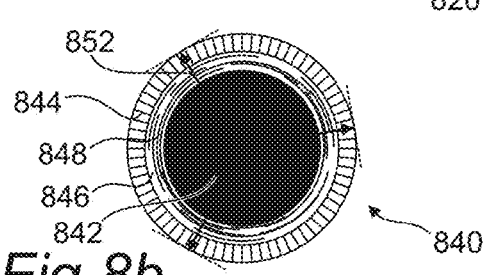
Fig 8b

ANS ASSESSMENT SYSTEMS, KITS, AND METHODS

CROSS REFERENCE TO RELATED APPLICATION

The present application is a continuation of U.S. patent application Ser. No. 15/503,180, filed Feb. 10, 2017, which is a national stage of International Application PCT/US2015/044235 which claims benefit of and priority to U.S. Provisional Application Ser. No. 62/035,444, filed on Aug. 10, 2014 and U.S. Provisional Application Ser. No. 62/060, 302, filed on Oct. 6, 2014, each entitled "ANS Assessment Systems, Kits, and Methods," by Landy Toth et al., the entire contents of both of which are incorporated by reference herein for all purposes.

BACKGROUND

Technical Field

The present disclosure relates to the field of physiologic monitoring. The disclosure relates to systems and methods for assessment of autonomic neural system (ANS) activity and/or neuroendocrine function of a subject. In particular, the disclosure relates to aspects of systems and methods for unobtrusively monitoring ANS activity and surrogates thereof from a subject while interfacing with a virtual and/or augmented reality environment.

Background

As chronic diseases continue to proliferate throughout the world, there is a heightened need to treat such conditions in a cost effective manner. New treatments and remote monitoring of patients with cardiovascular diseases (heart failure, post stroke, etc.), diabetes, kidney failure, chronic obstructive pulmonary disease (COPD), obesity, neurological disorders (depression, Alzheimer's disease, migraines, stress disorders, etc.), arthritis, among other ailments, for purposes of treatment or prevention of such diseases may substantially improve patient outcomes.

Congestive heart failure, hypertension, diabetes, and chronic renal failure have many different initial causes; however, all may include some form of autonomic dysfunction such as renal sympathetic nerve hyperactivity. Renal sympathetic nerves communicate signals with sympathetic centers located in the spinal cord and brain via afferent renal nerve activity, increasing systemic sympathetic tone; meanwhile, through efferent activity, renal nerves and arteries participate in sympathetic hyperactivity in response to signals from the brain, further increasing systemic sympathetic tone.

Sympathetic activation can initially be beneficial but eventually becomes maladaptive. In a state of sympathetic hyperactivity, a number of pathological events take place: abnormalities of hormonal secretion such as increased catecholamine, renine and angiotensin II levels, increased blood pressure due to peripheral vascular constriction and/or water and sodium retention, renal failure due to impaired glomerular filtration and nephron loss, cardiac dysfunction and heart failure due to left ventricular hypertrophy and myocyte loss, stroke, and even diabetes. Therefore, modulation (reduction/removal) of this increased sympathetic activity can slow or prevent the progression of these diseases.

Although ablation and neuromodulation of such nerves can have positive effects on drug resistant hypertension, glucose metabolism abnormality, among other neural disorders, current methodologies for denervation (e.g. ablation) and neuromodulation are conducted without adequate feedback. Furthermore, there are few clear and clinically implementable biomarkers for patient selection, outcome prediction, and surgical feedback of such procedures.

A head mounted display (HMD) is a display device worn on or about the head. HMDs usually incorporate some sort of near-to-eye optical system to emit a light image within a few centimeters of the human eye. Single eye displays are referred to as monocular HMDs while dual eye displays are referred to as binocular HMDs. Some HMDs display only a computer generated image (CGI) while blocking the user's external view. These HMD displays are often referred to as virtual reality (VR) displays. Other HMDs are capable of superimposing CGI over a real-world view. This latter type of HMD can serve as the hardware platform for realizing augmented reality (AR). With AR the viewer's image of the world is augmented with an overlaying CGI. Another term used to refer to various types of HMDs is a heads-up display (HUD). A HUD is any display that permits the user to view a CGI without having to look down or otherwise take their eyes significantly off their head up forward position. Both VR and AR HMDs can be implemented as HUDs.

SUMMARY

One objective of this disclosure is to provide systems, devices, methods, and kits for monitoring physiologic and/or physical signals from a subject. Another objective is to provide systems and methods for assessing the autonomic nervous system (ANS), and/or neuroendocrine system of a subject for the purposes of patient selection for a treatment, treatment feedback, treatment outcome prediction, and treatment follow-up. Yet another objective is to provide emotional, visual, and/or autonomic feedback of a subject immersed in a virtual and/or augmented reality environment.

The above objectives are wholly or partially met by devices, systems, and methods according to the appended claims in accordance with the present disclosure. Features and aspects are set forth in the appended claims, in the following description, and in the annexed drawings in accordance with the present disclosure.

According to a first aspect there is provided, a method for assessing sympathetic and/or parasympathetic neural activity in an eye of a subject including: taking a plurality of images of the eye over a period of time; identifying and tracking a position of one or more features of an iris of the eye across the images to generate one or more trajectories thereof; and analyzing the trajectories to generate one or more metrics relating to sympathetic and/or parasympathetic neural activity in the eye.

In aspects, the features of the iris may include one or more of a ciliary zone, a pupil, a sphincter muscle/pupillary zone, a crypt, a peripheral crypt, a contraction furrow, a mole, a region of alternative/distinct color, a color distorted region, a region of contrast, an identifiable region, a diameter, boundary, centroid, area, distortion, a combination thereof, or the like.

In aspects, the position of one or more of the features may be calculated relative to a reference point in the images (e.g. a center of the pupil of the eye, a contrast point in the eye, a fiduciary light field marking on the eye, a region of a sclera, to a boundary of the pupil, etc.).

In aspects, the trajectory may include a radial movement and/or a rotational movement about the reference point. Such movement of interest may include high speed microscopic movements of the feature, macroscopic movements of the feature, etc. A metric may be generated from one or more aspects of the trajectory (e.g. radial only, rotational only, radial and rotational, relative movement between features, combinations thereof, or the like).

In aspects, one or more of the metrics may be generated from a relative distance between features.

The method may include altering a light field near to one or more of the features in one or more of the images. Such altering may be performed within a visual spectrum of the subject and/or the altering the light field may occur over an optical spectrum visible in the images but without substantially impacting a light reflex of the eye.

The method may include analyzing microscopic movements in one or more of the trajectories to generate one or more of the metrics.

The method may include administering a medicament to the eye so as to affect the parasympathetic and/or sympathetic muscular response thereof. Some non-limiting examples of medicaments include an anticholinergic agent, an alpha andrenergic agent, a muscarinic receptor agonist, a sympathomimetic agent, combinations thereof, or the like.

The method may include performing a stress test on the subject before and/or during the tracking, the metric related to a subject response to the stress test.

In aspects, the stress test may include administration of a chemical, a drug, medicament, a hormone, an enzyme, a diuretic, a solution, electrolytes, a peptide, steroid, saline, a hypotonic solution, a hypertonic solution, a combination thereof, or the like to the subject. The administration may be topical, systemic, intravenous, intra-arterial, intra-parenchymal, sub-dermal delivery, transdermal delivery, rectal, via vaginal suppositories, via urethral suppositories, via nasal suppositories, via rectal suppositories, inhaled, a combination thereof, or the like.

In aspects, the stress test may include delivery of energy to, delivery of a focused ultrasound dose to a neural structure within, stimulation of, electrical stimulation of, presenting an audio field to, application of thermal stress to, presenting a light field to, presenting an image to, asking a question to, and/or playing music for the subject, or the like.

In aspects, the stress test may include providing a tactile input to one or more sites on the subject, stimulating, blocking, ablating, and/or treating one or more of a neural structure, a receptor, a nerve, a ganglion, a renal nerve, a renal receptor, a carotid sinus, a carotid body, a baroreceptor, a vagus nerve receptor, a skin surface, and/or an erogenous zone of the subject, a combination thereof, or the like.

In aspects, the stress test may include applying an electromagnetic field to, injecting a current into, applying pressure to, applying stroking to, or applying a change in barometric pressure surrounding the subject, or the like.

In aspects, the stress test may include having the subject sleep, cry, speak, laugh, lie down, jump, walk, run, change posture, exercise, perform a breath holding exercise, climb stairs, have sex, fight, play a game, relax, or the like.

In aspects, the method may include treating a target site within the patient, the metric related to a subject response to the treatment. Some non-limiting examples of treatments include one or more of performing an ablation, a neuromodulation, implantation of a neuromodulation device, a focused energy delivery, a radio frequency ablation, a microwave ablation, a high intensity focused ultrasound (HIFU) delivery, a cryoablation, a chemical ablation, a radiosurgical treatment, an optical ablation, an infrared ablation, a laser ablation, an MR guided HIFU treatment, or the like.

In aspects, the method may include administering a subsequent treatment and/or stress test to the target site, the metric during and/or after the subsequent treatment and/or stress test indicative of a state of completion of the treatment of the target site.

According to aspects there is provided, a method for assessing sympathetic and/or parasympathetic neural activity in a first eye and/or a second eye of a subject including: administering one of a muscarinic receptor agonist or an anticholinergic agent to the first eye; administering one of an alpha adrenergic agent or a sympathomimetic agent to the second eye; and tracking a position of one or more features of the first eye to generate a first metric relating to the sympathetic neural activity and tracking a position of one or more features of the second eye to generate a second metric relating to the parasympathetic neural activity.

In aspects, one or more of the features may include one or more of a ciliary zone, a pupil, a sphincter muscle/pupillary zone, a crypt, a peripheral crypt, a contraction furrow, a mole, a region of alternative/distinct color, a color distorted region, a region of contrast, an identifiable region, a diameter, boundary, centroid, area, distortion, combination thereof, or the like.

In aspects the method may include comparing the first metric to the second metric to determine a differential change in the sympathetic neural activity and the parasympathetic neural activity.

According to aspects there is provided, a system for monitoring one or more physiologic, autonomic neural, and/or electrophysiological signals from a subject, including: a head mounted display sized for placement onto a head of the subject including a visual input device and a back-facing imaging sensor; the visual input device arranged within a field of view of the subject when the head mounted display is coupled thereto, the visual input device configured to display an output image for the subject; the back-facing imaging sensor arranged with a field of view covering one or more facial features of the subject when the head mounted display is coupled thereto, the back-facing imaging sensor configured to generate one or more feedback images the subject; and a processor electrically and/or wirelessly coupled to the visual input device and the back-facing imaging sensor, the processor configured to deliver the output images, accept the feedback images, and analyze the images to determine one or more of the physiologic, autonomic neural, and/or electrophysiological signals.

In aspects, the head mounted display may include a facial interfacing member in accordance with the present disclosure (e.g. herein referred to as a shroud), the shroud arranged so as to isolate one or more eyes of the subject from a surrounding environment, when the head mounted display is coupled to the head of the subject.

In aspects, the shroud may include one or more sensors and/or electrodes, the sensors and/or electrodes arranged along the shroud so as to bias against one or more skin sites of the subject when the head mounted display is coupled to the head of the subject, the processor coupled to the sensors and/or electrodes.

In aspects, the electrodes may be arranged along the shroud so as to capture, in conjunction with the processor, an electroretinogram, an electrooculogram, an electroencephalogram, an electromyogram, or a combination thereof from the subject.

In aspects, the visual input device may be configured to alter a light field near to one or more of the facial features via an output image, the back-facing imaging sensor configured to capture one or more aspects of the light field in a feedback image. The altered light field may occur over an optical spectrum without substantially impacting a light reflex of the eye.

In aspects, one or more of the facial features may include an iris, the back-facing imaging sensor configured to image the iris with a pixel count across the diameter of the iris of more than 50 pixels, more than 100 pixels, more than 200 pixels, more than 400 pixels, or the like, the processor including an algorithm configured to track one or more features of the iris.

In aspects, the back-facing imaging sensor may be configured to take more than 10 images per second, more than 20 images per second, more than 40 images per second, more than 80 images per second, or the like.

In aspects, one or more of the features of the iris may include one or more of a ciliary zone, a pupil, a sphincter muscle/pupillary zone, a crypt, a peripheral crypt, a contraction furrow, a mole, a region of alternative/distinct color, a color distorted region, a region of contrast, an identifiable region, a diameter, boundary, centroid, area, distortion, a combination thereof, or the like.

In aspects, the visual input device may include a display, a light emitting diode (LED), a visible light LED, a broadband light source, one or more narrow band light sources, an infrared (IR) light source, an ultraviolet (UV) light source, an IR LED, a light source array, a curved display, an active-matrix organic light-emitting diode (AMOLED) display, a flexible AMOLED display, a transparent display, a semi-transparent display, an augmented reality display, a projected display, a smart glass display, an electrochromatic film, a combination thereof, or the like.

In aspects, the back-facing imaging sensor may include or be a camera, a visible light camera, a near infrared camera, an infrared camera, a short wavelength infrared camera, a complementary metal-oxide-semiconductor (CMOS) imaging sensor, an infrared imaging sensor, a laser speckle imaging sensor, a coherence tomographic imaging element, a combination thereof, or the like.

In aspects, the head mounted display may include a plurality of visual feedback devices, and/or a plurality of back-facing imaging sensors.

In aspects, the head mounted display may include one or more audio input devices, arranged so as to interface with the ears of the subject when the head mounted display is coupled to the head of the subject, the audio input devices coupled to the processor, the audio input devices configured to render an audio stream provided by the processor. The processor may be configured to assess one or more physiologic responses to the audio stream, a combined audio/visual stream, an audio/visual presentation, etc.

In aspects, the head mounted display may include one or more optical sensors arranged so as to bias against one or more skin sites of the subject when the head mounted display is coupled to the head of the subject, the processor coupled to the optical sensors to receive one or more hemodynamic and/or tissue analyte signals. In aspects, one or more of the optical sensors may be integrated into the shroud, integrated into the audio input device, and/or arranged so as to interface with a nose, a nasal bridge, a temple region, an ocular region, an ear, an earlobe, and/or an ear canal of the subject.

In aspects, the system may include one or more physiologic sensors coupled to the body of the subject to produce one or more physiologic signals therefrom, each of the physiologic sensors in wireless communication with the processor to provide the physiologic signals thereto. One or more of the physiologic sensors may include an electrophysiologic sensor, a heart-rate sensor, a skin neural activity sensor, a temperature sensor, a thermal gradient sensor, a barometer, an altimeter, an accelerometer, a gyroscope, a humidity sensor, a magnetometer, an inclinometer, an oximeter, a colorimetric monitor, a perfusion sensor, a sweat analyte sensor, a galvanic skin response sensor, an interfacial pressure sensor, a flow sensor, a stretch sensor, a microphone, or the like.

In aspects, one or more of the physiologic sensors may be arranged for placement onto the perineal region, the perianal region, the pubic region, the inner thigh region, the posterior knee region, the neck, the ear, the ocular region, the breast, the axilla, the elbow, the wrist, the palm, the foot, the lips, and/or an erogenous zone of the subject.

In aspects, the system may include a stimulating device selected from an electrical stimulator, a thermoregulating device, a heating coil, a thermoelectric device, a Peltier device, a tactile stimulating component, a vibratory stimulating element, a combination thereof, or the like arranged so as to interface with the skin of the subject when coupled thereto.

In aspects, the system may include a treatment system for treating a target site within the subject, the treatment system including one or more of an ablation system, a neuromodulation device, a neuromodulation implant, an ablation catheter, a focused energy delivery device, a radio frequency ablation system or catheter, a microwave ablation system or catheter, an ultrasound energy delivery system, a high intensity focused ultrasound (HIFU) delivery system or catheter, a cryoablation system or catheter, a chemical ablation system or catheter, a radiosurgical system, an optical ablation system, an infrared ablation system, a laser ablation system, an MR guided HIFU system, or the like.

In aspects, the system may include a vascular substance delivery device, configured so as to administer a substance to an artery, a vein, an arteriole, and/or a venule of the subject.

In aspects, the processor may be included in or coupled to a host device, the host device integrated into a bedside alarm clock, housed in an accessory, within a purse, a backpack, a wallet, is or is included in a mobile computing device, a smartphone, a tablet computer, a pager, a laptop, a local router, a data recorder, a network hub, a server, a secondary mobile computing device, a repeater, or a combination thereof.

According to aspects there is provided, use of a system in accordance with the present disclosure to confirm completion of, follow up on, confirm partial completion of, monitor a patient response to, or patient selection in connection with, a denervation procedure, a renal denervation procedure, ablation of a renal nerve, ablation of renal artery, and/or ablation of an accessory renal artery.

According to aspects there is provided, use of a system in accordance with the present disclosure to enhance a gaming experience of, assess an emotional state of, perform a lie detection test on, enhance a virtual shopping experience of, reduce a stress state of, or enhance a virtual interaction between a user and a subject.

According to aspects there is provided use of a system in accordance with the present disclosure to perform an electroretinogram, an electroencephalogram, and/or an electrooculogram on a subject.

According to aspects there is provided, a method for assessing an autonomic nervous system of a subject, including: monitoring neural activity in an ocular feature of the subject to obtain one or more neural activity signals; performing a stress test on the subject; and analyzing the signals obtained before, during, and/or after the stress test to generate a metric, diagnostic, report, and/or additional signals therefrom relating to the autonomic nervous system of the subject.

In aspects, the stress test may include administration of a chemical, a drug, medicament, a hormone, an enzyme, a diuretic, a solution, electrolytes, a peptide, steroid, saline, a hypotonic solution, a hypertonic solution, a combination thereof, or the like to the subject. In aspects, the administration may be topical, systemic, intravenous, intra-arterial, intra-parenchymal, sub-dermal delivery, transdermal delivery, rectal, via vaginal suppositories, via urethral suppositories, via nasal suppositories, via rectal suppositories, inhaled, a combination thereof, or the like.

In aspects, the stress test may include delivery of energy to, stimulation of, electrical stimulation of, presenting an audio field to, application of thermal stress to, presenting a light field to, presenting an image to, asking a question to, or playing music for, the subject.

In aspects, the stress test may include providing a tactile input to one or more sites on the subject. In aspects, the stress test may include stimulating one or more of a carotid sinus, a carotid body, a baroreceptor, a vagus nerve receptor, or an erogenous zone of the subject.

In aspects, the stress test may include applying an electromagnetic field to, injecting a current into, applying pressure to, applying stroking to, or applying a change in barometric pressure surrounding the subject (e.g. such as to the skin of the subject, to an internal stimulation site, etc.).

In aspects, the stress test may include having the subject sleep, cry, laugh, lie down, jump, walk, run, change posture, exercise, perform a breath holding exercise, climb stairs, or the like.

In aspects, one or more stimulation and/or monitoring sites may be coupled to the perineal region, the perianal region, the pubic region, the inner thigh region, the posterior knee region, the neck, the ear, the ocular region, the breast, the axilla, the elbow, the wrist, the palm, the foot, the lips, and/or an erogenous zone of the subject.

One or more of the steps of a method in accordance with the present disclosure may be performed at least in part by a system in accordance with the present disclosure.

According to aspects there is provided, a system for performing a neuromodulation and/or ablation procedure on a target site within a subject including: a treatment system for delivering energy or a chemical to the target site; a head mounted display including a back-facing imaging sensor configured to measure one or more electrophysiological signals, neural traffic signals, and/or physiologic parameters from the head of the subject so as to produce one or more activity signals; and a processor included in or coupled to the head mounted display, the processor configured to receive the activity signal(s), and/or one or more signals generated therefrom, the processor including an algorithm, the algorithm configured to analyze the activity signal(s) to determine the effect of the treatment system on the target site.

In aspects, the system may include one or more additional monitoring devices, the algorithm configured to compare activity signal(s) generated by the plurality of monitoring devices and the head mounted display against each other to determine the effect of the treatment system on the target site.

In aspects, the treatment system may include one or more of an ablation system, a neuromodulation device, a neuromodulation implant, an ablation catheter, a focused energy delivery device, a radio frequency ablation system or catheter, a microwave ablation system or catheter, an ultrasound energy delivery system, a high intensity focused ultrasound (HIFU) delivery system or catheter, a cryoablation system or catheter, a chemical ablation system or catheter, a radiosurgical system, an optical ablation system, an infrared ablation system, a laser ablation system, an MR guided HIFU system, or the like.

In aspects, the algorithm may be configured to indicate when only a partial neuromodulation and/or ablation procedure has been performed on a target site, and/or when a complete procedure has been performed on the target site.

In aspects, the system may include a stimulating device selected from an electrical stimulator, a thermoregulating device, a heating coil, a thermoelectric device, a Peltier device, a tactile stimulating component, a vibratory stimulating element, or a combination thereof, the stimulating device configured to stimulate the subject at one or more stimulation sites, the algorithm configured to compensate for the stimulation in the analysis. In aspects, one or more of the stimulating devices may be embedded in the treatment system. In aspects, the treatment system may be configured to deliver a stimulating energy or chemical agent to the target site, and/or one or more stimulatory sites within the subject (e.g. such as a HIFU stimulation of a neural structure in order to assess the function thereof, perform a stress test thereupon, assess treatment thereof, etc.).

In aspects there is provided, a method for assessing and/or selecting a subject for a renal denervation procedure, including monitoring blood pressure of the subject to obtain one or more physiologic signals, performing a stress test on the subject, and analyzing the physiologic signal(s) obtained before, during, and/or after the stress test to generate a metric, diagnostic, report, and/or additional signals therefrom relating to the autonomic nervous system of the subject, the metric, diagnostic, report, and/or additional signal relating to the suitability of the subject for a renal denervation procedure.

In aspects, the stress test includes administration of a chemical, an adrenoceptor agonist/antagonist, a drug, medicament, a hormone, an enzyme, a diuretic, a solution, electrolytes, a peptide, steroid, saline, a hypotonic solution, a hypertonic solution, or a combination thereof to the subject.

In aspects, the method includes monitoring one or more of sympathetic neural outflow, the renal blood flow, urine flow rate, sodium excretion rate, pupil diameter, iris feature movement, skin temperature, heart rate, heart rate variability, combinations and/or surrogates thereof to generate one or more of the physiologic signals. In aspects, the substance is guanethidine.

In aspects, the subject is considered suitable if the blood pressure changes by more than 1%, more than 5%, more than 10%, or more than 20%, during the stress test. In aspects, the subject is considered suitable if the renal blood flow, urine flow rate, sodium excretion rate, or pupil diameter, changes by more than 1%, by more than 5%, or by more than 10% during the stress test.

In aspects, the blood pressure change is normalized with the sympathetic neural outflow, the renal blood flow, urine flow rate, sodium excretion rate, and/or a surrogate thereof, to enhance the selectivity of the assessment.

In aspects, the administration is topical, systemic, intravenous, intra-arterial, intra-parenchymal, sub-dermal delivery, transdermal delivery, rectal, via vaginal suppositories, via urethral suppositories, via nasal suppositories, via rectal suppositories, inhaled, or a combination thereof.

In aspects, the stress test includes delivery of energy to, stimulation of, electrical stimulation of, presenting an audio field to, application of thermal stress to, presenting a light field to, presenting an image to, asking a question to, or playing music for, the subject. In aspects, the stress test includes applying a cooling thermal stress to the hand, forehead, nose, lip, ear, and/or neck of the subject. In aspects, the stress test includes applying a cooling thermal stress to the hand and to the forehead of the subject to obtain separate reflex responses thereto, at least a portion of the metric derived from the difference in physiological signals obtained during the separate reflex responses. In aspects, the stress test includes providing a tactile input to one or more sites on the subject. In aspects, the stress test includes stimulating one or more of a carotid sinus, a carotid body, a baroreceptor, a vagus nerve receptor, or an erogenous zone of the subject. In aspects, the stress test includes applying an electromagnetic field to, injecting a current into, applying pressure to, applying stroking to, or applying a change in barometric pressure surrounding the subject. In aspects, the stress test includes having the subject sleep, cry, laugh, lie down, jump, walk, run, change posture, exercise, perform a breath holding exercise, or climb stairs.

In aspects, one or more of the sites is coupled to the perineal region, the perianal region, the pubic region, the inner thigh region, the posterior knee region, the neck, the ear, the ocular region, the breast, the axilla, the elbow, the wrist, the palm, the foot, the lips, and/or an erogenous zone of the subject.

In aspects, one or more of the steps are performed at least in part by a system in accordance with the present disclosure.

BRIEF DESCRIPTION OF THE DRAWINGS

Several aspects of the disclosure can be better understood with reference to the following drawings. In the drawings, like reference numerals designate corresponding parts throughout the several views.

FIGS. 3a-3c show aspects of multi-site monitoring, stimulation, stress application, and/or treatments applied to a subject each in accordance with the present disclosure.

FIGS. 4a-4c illustrate aspects of methods for monitoring, stressing, and/or treating one or more regions of a subject each in accordance with the present disclosure.

FIGS. 5a-5c illustrate aspects of head mounted displays (HMD) each in accordance with the present disclosure.

FIG. 6a-6d show aspects of an HMD in accordance with the present disclosure.

FIG. 7 shows aspects of an eye interacting with a visual input device in accordance with the present disclosure.

FIGS. 8a-8b show aspects of the pupil and the iris of interest for inspection with a system in accordance with the present disclosure.

DETAILED DESCRIPTION

Figure 1A:
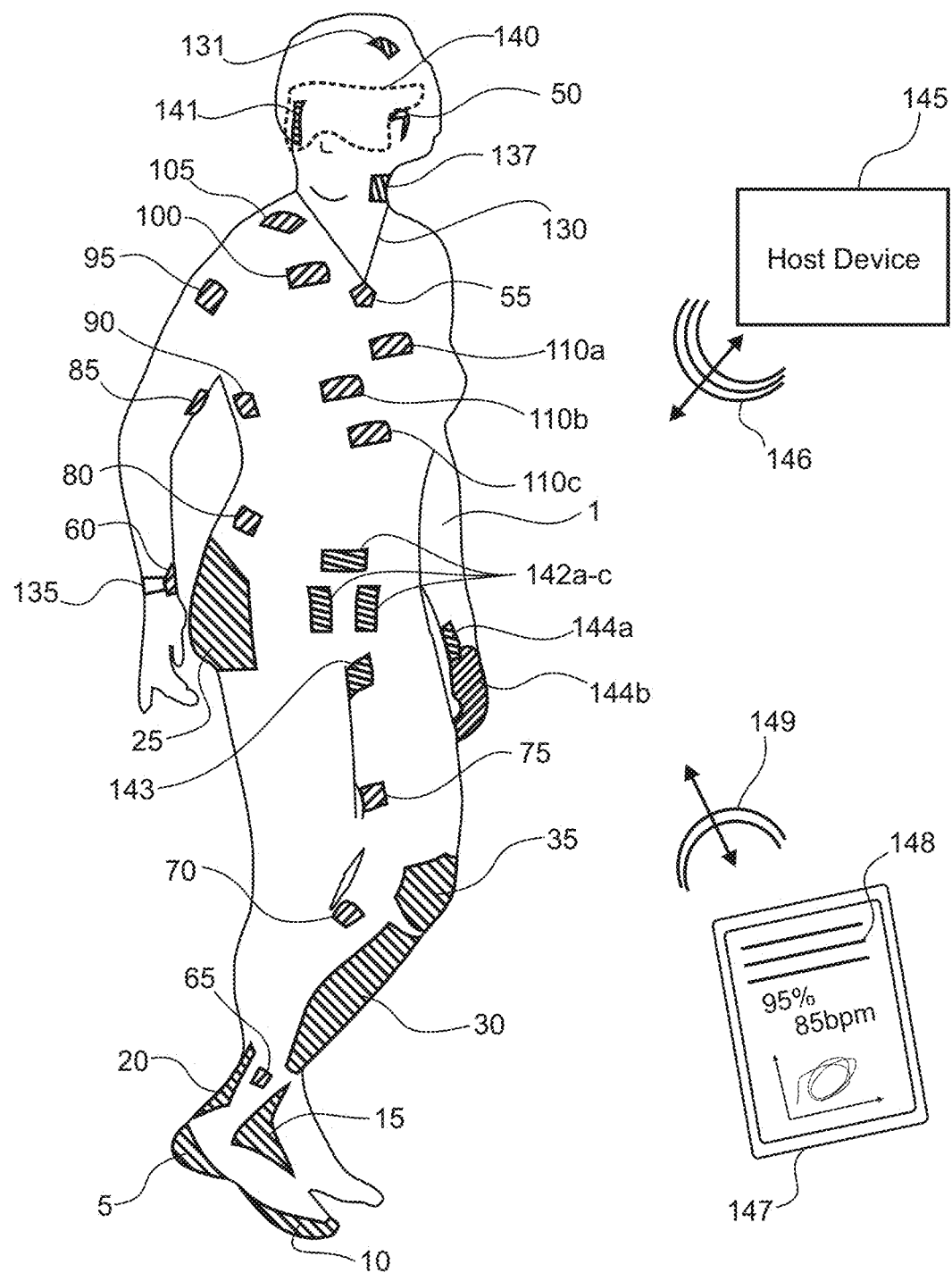
FIGS. 1a-1c show aspects of modular physiologic monitoring systems in accordance with the present disclosure.

Particular embodiments of the present disclosure are described herein below with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

A modular physiologic monitoring system in accordance with the present disclosure for assessing one or more physiologic parameters of a subject (e.g. a human subject, a patient, an athlete, a trainer, an animal, such as equine, canine, porcine, bovine, etc.) with a body may include one or more patches, each patch adapted for attachment to the body of the subject (e.g. attachable to the skin thereof, reversibly attachable, adhesively attachable, with a disposable interface and a reusable module, etc.). In aspects, the physiologic monitoring system may include one or more modules, each module may include a power source (e.g. a battery, a rechargeable battery, an energy harvesting transducer, microcircuit, and an energy reservoir, a thermal gradient harvesting transducer, a kinetic energy harvesting transducer, a radio frequency energy harvesting transducer, a fuel cell, a biofuel cell, etc.), signal conditioning circuitry, communication circuitry, one or more sensors, or the like, configured to generate one or more signals (i.e. physiologic and/or physical signals).

Each patch or patch/module pair may be configured to monitor one or more local physiologic and/or physical parameters of the attached subject (e.g. local to the site of attachment, etc.), local environment, combinations thereof, or the like, and to relay such information in the form of signals to a host device (e.g. via a wireless connection, via a body area network connection, or the like), one or more patches or modules on the subject, or the like.

In aspects, the host device may be configured to coordinate information exchange to/from each module and/or patch, and to generate one or more physiologic signals, physical signals, environmental signals, kinetic signals, diagnostic signals, alerts, reports, recommendation signals, commands, combinations thereof, or the like for the subject, a user, a network, an EHR, a database (e.g. as part of a data management center, an EHR, a social network, etc.), a processor, combinations thereof, or the like.

Some non-limiting examples of systems, devices, and methods which may be suitable for performing one or more aspects of a modular monitoring system in accordance with the present disclosure are generally detailed in co-pending international patent application PCT/US2014/041339, and U.S. provisional patent applications 62/032,515 and 62/032,565 the disclosures of which are expressly incorporated herein by reference.

According to aspects there is provided a head mounted display (HMD) with one or more back facing cameras, the back facing camera(s) oriented so as to capture ocular parameters, pupil diameters, iris features, iris surface properties, uvea features, uvea blood flow, iris tonal changes, uvea tonal changes, uvea color changes, facial expressions, eye movements, combination thereof, or the like from the subject during use. In aspects, the HMD may include a plurality of back facing cameras, each camera positioned so as to capture a portion of the facial response of the subject, a facial feature (e.g. an eye, lips, an eyebrow, etc.), the HMD or a processor coupled thereto programmed with machine readable code and/or imaging algorithms configured so as to analyze inputs from the plurality of cameras and assemble an array of subject responses, physiologic metrics, or the like during use.

In aspects, one or more of the back facing cameras may be arranged so as to capture light from the retina of an eye of the subject during use. The retinal reading camera may be configured to generate one or more retinal images, a processor and/or microcircuit programmed with an image analysis algorithm coupled thereto may be configured to analyze the retinal images to determine aspects such as retinal blood flow, red lesion detection, blood vessel segmentation, detection of neovascularization in related fundus images, diabetic retinopathy, macular degeneration, lesion analysis, etc.

The retina reading camera or an equivalent photodetector may be configured to analyze the state of the retina of the subject, monitor a plethysmographic aspect of the retina, of the eye, generate a pulse from a temporal stream of retinal images, a substantially continuous blood pressure surrogate therefrom, or the like. Such a configuration may be advantageous for assessing a blood pressure response of the subject during use thereof.

The HMD may include one or more photoplethysmographic (PPG) sensors. The PPG sensor may be directed towards one or more tissue sites on the face, neck, head, of the subject (e.g. an eye, a retina, an ocular tissue, a nose, a nostril, a nasal lining, an ear lobe, etc.). The PPG sensor may be advantageous for capturing one or more cardio-vascular parameters like blood oxygen saturation level, heart pulse rate, respiratory rate, bilirubin, or the like in the target tissues. Such sensor incorporation may be advantageous for monitoring apnea and respiratory sinus arrhythmia in a subject. Such PPG sensors may be used to obtain information about tissue oxygenation, local blood flow, changes in blood flow in a tissue. The PPG sensor may include a reflectance probe to interact with a facial tissue, eye, etc. or a transmittance probe to interact with one or more of a nostril, lip, ear lobe, etc.

In aspects, the HMD may include one or more physiologic sensors in accordance with the present disclosure, arranged upon the HMD such that the sensors interface with the subject when the HMD is worn. Such physiologic sensors may be arranged on the HMD such that they interface with the skin, facial muscles, nasal bridge, ear, ear canal, temple, cheek, mouth, or the like of the subject. The HMD may include one or more electrodes, the electrodes integrated into a padding, landing pad, face-biased padding, mounting feature, or the like. The electrodes may be arranged within the HMD so as to interface with the eye, muscles around the eye, around the cheek, face, temple, forehead, around the head, etc. so as to measure one or more of electroencephalogram (EEG), electroretinogram (ERG), electrooculography (EOG), local tissue perfusion, bioimpedance, activity, etc.

Some non-limiting aspects of facial expressions that may be monitored include all facial expressions, monitoring mouth, eye, neck, and jaw muscles, smiling, frowning, voluntary and involuntary muscle contractions, tissue positioning and gestural activity, twitching, blinking, eye movement, saccade, asymmetrical movements, patterned head movement, rotating or nodding, head positioning relative to the body, vocal cord tension and resulting tonality, vocal volume (decibels), and speed of speech.

Some non-limiting emotional states conveyed by one or more facial expressions include happy, sad, fearful, angry, surprised, disgusted, appalled, happily surprised, happily disgusted, sadly fearful, sadly angry, sadly surprised, sadly disgusted, fearfully angry, fearfully surprised, fearfully disgusted, angrily surprised, angrily disgusted, disgustedly surprised, hatred, and awed. The HMD or a processor coupled thereto may be programmed with machine readable code including image processing software to predict one or more emotional states of the subject or changes therein as monitored by the one or more cameras during use.

Some non-limiting examples of involuntary physiologic metrics which may be monitored include muscle movement, twitching, ocular orientation, skin neural activity, pupil size, pupil dilation, iris sphincter movement, iris dilation movement, iris feature movement, tearing, blink rate, lip movement, snickering, rates of change of such metrics, recovery of such metrics, etc.

The HMD may include one or more light sources (e.g. LEDs, OLEDs, an active-matrix organic light-emitting diode, etc.), a display, a flexible display, a curved display, a partially transparent display, or the like to convey a visual image or environment into the field of view of the subject. The HMD may include one or more light pipes to deliver light between the eyes of the subject and one or more of the displays, cameras, or light sources. The HMD may include one or more ear buds to deliver an audible stream to one or both ears of the subject.

In aspects, the HMD may include one or more sensors arranged to measure one or more of, but not limited to, respiration (breathing rate, breathing volume, lung stress or load, or the like), blood pressure, blood oxygen level, heart rate variability, heat flux, galvanic skin response, core body temperature, skin temperature, sympathetic or parasympathetic response, combinations thereof, or the like in order to assess the function of the ANS or changes therein during an assessment, before, during, and/or after a stress test, before, during, and/or after a procedure, etc.

The monitoring solutions described herein may be applied to a wide range of monitoring situations. Some non-limiting examples of such applications include hospital based monitoring of patients, remote monitoring of patients, heart-rate monitoring, electrocardiographic monitoring of fitness, athletic, aerobic activities, yoga, stress management, biomechanics and biometric monitoring systems (e.g. so as to monitor electromyography (EMG), proprioceptive inputs, etc.), heart-rate variability training, heart-rate variability assessment, traumatic brain injury assessment, muscle tension assessment, tissue assessment (e.g. determination of fat content in tissues around the body, changes in fat content during workout, etc.), sleep studies, sleep monitoring, sleep apnea assessment, physiologic assessment of sleep state, sleep biofeedback, snoring analysis, bruxism monitoring, physiotherapy, event response (e.g. stroke capture, assessment, response, and therapy, heart attack, heart attack prediction, atrial fibrillation, syncope, ST-segment depression or elevation, onset of myocardial ischemia, p-wave analysis, onset of snoring, night terrors, sleep walking, etc.), hydration and fluid management, long-term monitoring, gaming or computer input devices, product testing, marketing analysis, virtualization of emotional experiences, physiotherapy, combinations thereof, or the like.

Some non-limiting examples of procedures which may be completed at least in part by a system or device in accordance with the present disclosure include patient selection for, procedural feedback, procedural confirmation, and follow-up of a neuroendocrine treatment, an ANS treatment, a neuromodulation procedure, a neural ablation procedure, a chemotherapy, a subject reaction to a drug, a subject reaction to a stress test in accordance with the present disclosure, or the like.

Some non-limiting examples of applications which may be enabled at least in part by a system, device, and/or procedure in accordance with the present disclosure include gaming, assessment of the neurological state of an athlete, performing a retinogram on a subject, assessment of retinal function of a subject, determination of retinal detachment of a subject, assessment of a stroke patient, assessment of retinal function, assessment of the cognitive function of a subject, assessment of the oculomotor function of subject, independent assessment of the sympathetic nervous system (SNS) and parasympathetic nervous system (PNS) of a subject, assessment of traumatic brain injury of a subject, assessment of fatigue of a subject, shopping, interaction with a digital concierge, integration of a subject's emotional response into a game, a shopping transaction, as marketing feedback, interaction with a digital concierge, feedback to a suggestion, to gauge an intent of the subject, or the like, for representation of physiologic metrics for other gamers in a cooperative gaming environment, alerts associated with a physiologic metric of a subject, etc.

In aspects, the monitoring of emotional response and selection preference of the subject, may provide a company, manufacturer, advertiser, or retailer, superior feedback with regard to consumer's behavior and reactions to their products. In aspects, such an emotional response may include a behavioral (physiological) and query (questionnaires) component. The query component may be conducted in real-time, before, during, and/or after the consumer has been exposed to the intended environment, store, concierge suggestion, game event, website, journal entry, etc. The query component may include asking the subject about their emotional state, confirming the measured state, confirming a preference, persuading the subject to make a purchase, or the like.

A system in accordance with the present disclosure may be configured to assess the emotional response of the subject related to one or more stimulatory inputs thereto and to generate an emotional state vector or metrics therefrom (e.g. a semi-quantitative structure containing the present emotional and/or physiological state of the subject, a state gradient, so as to better quantify the actual state of the subject, etc.). Such emotional response may be advantageous for determining the subject's level of interest to a stimulatory input (e.g. an audio/visual presentation, a visual image, an audio field, an olfactory input, a gustatory "taste" input, etc.). Such information may be provided to a search engine, a digital concierge, an adaptive learning algorithm, or the like in order to more deeply assess the interests and/or desires of the subject. Such information may be incorporated into a task or product suggestion engine, a marketing report, personalization of a customer preference list, suggestion of a partner, a dating application, suggestion of news, suggestion of reading materials, etc. Thus, the emotional and/or physiologic feedback provided by a system in accordance with the present disclosure may be advantageous in improving man-machine interaction, improving the "human" quality of machine learning algorithms, improving the suggestions made by a digital concierge, etc.

Such emotional state metrics may be provided to a learning algorithm so as to improve the responsiveness and/or utility of a digital concierge. Such guidance may be incorporated into a digital concierge in order to improve its ability to judge the intentions of the subject, to assess an (internal) response of the subject to a suggestion (e.g. to assess a response, which the subject would not likely provide openly to the digital concierge, etc.), or the like.

According to aspects, the HMD and/or a processor programmed with an algorithm coupled thereto may be configured for assessment of gaze (e.g. to assess where the subject is looking, where the subject is focusing within a virtual and/or augmented reality, or the like). Such gaze assessment may be coupled in real-time with the visual field provided to the subject by the HMD in order to improve the realism of the visual field for the subject. In one non-limiting example, the biometrics of the ocular configuration of the subject may be determined in order to personalize the visual field presented to the subject, such customization may include eye positioning with respect to one or more displays in the HMD, determining one or more ocular parameters of the subject (e.g. such as determined during a calibrating visual test of the subject, axial length (AL), central anterior chamber depth (CACD) and lens thickness (LT) of the eyes of the subject, etc., field of view, near sightedness, far sightedness, astigmatism, etc.), and/or compensating in the visual field for one or more movements (e.g. compensation for saccade, blind spot related movement, nystagmus related movements, etc.).

In aspects, the HMD may visually and/or via one or more physiologic sensors, assess the state of alertness of the subject, the state of hydration, etc. based upon one or more images of the eye of the subject, changes in the positioning of the eyelids, changes in the blink-rate of the eye, changes in the radius of the eye, changes in the surface texture of the eye (e.g. assess based on reflection of the light from the visual field therefrom), or the like. In aspects, such information may be used to evaluate a state of sleep deprivation of the subject, a state of eye strain, or the like. Facial muscular movements such as blinking may be assessed optically and/or via one or more electromyographic sensors coupled to the ocular regions of the face of the subject during use. The blink rate of the subject may be related to a state of irritation of the subject, a lack of hydration, a state of tiredness, a state of activity of tear glands, etc.

Such information may be coupled with biometric identification of the subject, such that the subject may be identified automatically when the HMD is initially interfaced with the head of the subject (via one or more biometrics, iris properties, ocular parameters, facial features, etc.), the compensation in the display occurring automatically thereafter. Such a configuration may be advantageous so as to enhance the user experience associated with interfacing with the HMD without having to manually configure any calibration aspects thereof.

In aspects, a plurality of metrics may be collected from the different sites on the subject: amplitude, time delay, polarity, ratio between wave components of the signal, movement artifacts, breathing artifacts, etc. may be used to generate a series of location metrics. Such information may be compared against previously collected maps (e.g. generated from studies with correlated camera images and electrophysiologically collected signals, etc.) and compared against the data collected during a calibration test to determine the location of one or more patch/module pairs.

One or more patch/module pairs may be equipped with one or more orientation determining sensors, such as one or more accelerometers, barometers, tilt sensors, gyroscopes, combinations thereof, etc. Information gleaned from one or more of such orientation determining sensors may be used in combination with one or more methods in accordance with the present disclosure to determine, enhance, confirm, etc. placement of the patch/module pairs on the subject.

In aspects, a system in accordance with the present disclosure may include one or more feedback components (e.g. a device with audible feedback, tactile feedback, visual feedback, combinations thereof, etc.), to provide a subject, coach, practitioner, caregiver, partner, or the like with information, commands, or prompts, pertaining to the physiologic and/or physical signals captured by one or more patch/modules arranged upon the subject. In aspects, such feedback may be used to enhance the sleep state of a subject, interrupt a sleep event to return a subject to a safe or comfortable sleeping state (e.g. interrupt a sleep walking event, a snoring event, a sleep apnea event, night terrors, nightmares, etc.). In aspects, such feedback may be analyzed in combination with the electrophysiological and/or physiologic signals to alter the state of the subject (e.g. the mood, the sleep pattern, the state of sleep, to prevent wake-up, to initiate wake-up, etc.).

In aspects, a feedback component in accordance with the present disclosure may include a heads-up-display (HUD), optionally integrated into an HMD in accordance with the present disclosure, such as may be provided by a pair of HUD ready glasses, Google Glass™, or the like. In aspects, the HUD may include visual representation of the physiologic and/or physical signals for a wearer (e.g. the subject, a coach, a caregiver, etc.), and/or signals or metrics related thereto or derived therefrom. In aspects, a plurality of such feedback mechanisms may be used to enhance the user experience, such as a combination of audible feedback (i.e. via a loudspeaker), and visual feedback (e.g. on a HUD, via an LED, etc.).

In aspects, an augmented reality application may be envisaged using a pair of HUD ready glasses, HMD, or via a handheld device with both display and camera functionality (e.g. a tablet, etc.). In aspects, aspects associated with muscle exertion, electrocardiographic data, etc. may be superimposed onto movements associated with the monitoring site so as to highlight such activities to an observer. In one non-limiting example, heart-rate data may be translated into an amplitude parameter for pixel movements and overlaid onto the display or HUD over top of the torso of the subject as displayed in the image. In such an example, a physiotherapist may be able to visualize "exertion" of a muscle group of a subject as it is overlaid onto that particular muscle group during a monitoring session. The exertion may be compared against previous bests, in the context of physiotherapy, may be compared against capabilities (i.e. from previously collected history) and compared against maximal exertion levels, etc. so as to avert injury, optimize an exercise for a subject, maximize the exertion of a local muscle group within a safety window, monitor muscle fatigue during exercise, or the like. Such a system may be advantageous for allowing a user (e.g. the subject, a physiotherapist, a physician, a nurse, etc.) to assess one or more physiologic parameters of the subject while observing the subject or aspects thereof in a display (i.e. without taking attention away from the subject).

A system in accordance with the present disclosure may be configured to assess one or more physiologic responses of the subject to one or more stress tests. Some non-limiting examples of stress tests in accordance with the present disclosure include administration of a chemical, a drug, medicament, a hormone, an enzyme, a diuretic, a solution, electrolytes, a peptide, steroid, a combination thereof, or the like to a subject (e.g. delivery via topical, systemic, intravenous, intra-arterial, intra-parenchymal, sub-dermal delivery, oral, transdermal delivery, rectal, vaginal, urethral, oral, or nasal suppositories, inhaled approaches, into a target artery, into a target organ, or the like), delivery of energy, stimulation, electrical stimulation, presenting an audio field to a subject, application of thermal stress, a light field, an image, asking the subject a question, playing music, generating an audible signal for the subject, a change in humidity, a tactile input (e.g. to one or more sites on the body, to a region of skin, to a carotid sinus, to a carotid body, to a baroreceptor, to a vagus nerve receptor, to an erogenous zone on the skin, etc.), application of an electromagnetic field, injection of a current, application of pressure, application of stroking to a region of skin, a change in barometric pressure, a change in posture, an exercise, a breath holding exercise, a stair climbing exercise, to evoke an emotional response therefrom, to alter an environmental state thereabout, and/or combinations thereof to a subject or one or more sites there upon or therein. The stress tests may be devised and implemented so as to cause a differential response between the parasympathetic state and the sympathetic state of a subject (e.g. overall, of a branch of the ANS, as relating to afferent traffic of one or more parts of the ANS, or the like).

The stress test may include having the subject perform a Valsalva maneuver, a tilt table test, elevating one or more legs, transient sitting to standing exercises, execute a change in posture, move from a prone position to a sitting or standing position, a breath hold technique, or combinations thereof. In aspects, the stress test may include administration, injection, and/or infusion of an α-receptor agonist/antagonist, a β-receptor agonist/antagonist, a vasodilator (e.g. endothelium-derived hyperpolarizing factor (EDHF), potassium, nitric oxide, a nitrovasolidator, sodium nitropusside, nitroglycerin, β-2 adrenergic receptor agonists, histamine, prostacyclin, prostaglandin, vasoactive intestinal peptides, adenosine, adenosine triphosphate (ATP), adenosine diphosphate (ADP), L-arginine, bradykinin, substance P, niacin, carbon dioxide ($CO_2$), etc.), a vasoconstrictor (e.g. ATP, muscarinic agents, acetylcholine, neuropeptide Y (NPY), adrenergic agonists, epinephrine, norepinephrine, dopamine, thromboxane, endothelin, angiotensin II, asymmetric dimethylarginine, antidiuretic hormone, vasopressin, etc.), a neuroblocker, a neurostimulant, a diuretic, insulin, glucose, a receptor agonist, a receptor antagonist, a beta-adrenergic receptor antagonist, angiotensin-11 converting enzyme inhibitor, calcium channel blocker, an 3-hydroxy-3-methylglutaryl-coenzyme A (HMG-CoA) reductase inhibitor, digoxin, anticoagulants, beta blockers, angiotensin-converting-enzyme (ACE) inhibitors (e.g. captopril, perindopril, lisinopril, enalapril, ramipril, etc.), one or more steroids (e.g. diflorasone, betamethasone, dexamethasone, clobetasol, prednisolone, mometasone, methylprednisolone, Deprodone, difluprednate, fluocinonide, amcinonide, triamcinolone, difluprednate, hydrocortisone, etc.), testosterone, or the like, into the body of the subject, into an organ of the subject, into a lumen of the subject, into an artery, a vein, a renal artery, into one or more of the monitoring sites, etc.

In aspects, the stress test may include administering a bolus of a nitrovasodilator to the subject. Some non-limiting examples of nitrovasodilators include glyceryl trinitrate (nitroglycerine), isosorbide mononitrate (ISMN) and isosorbide dinitrate (ISDN), itramin, pentaerithrityl tetranitrate, propatylnitrate, tenitramine, trolnitrate, nicorandil, molsidomine and its active metabolite linsidomine, and sodium nitroprusside. In aspects, a bolus of nitroglycerine (TNG) may be administered orally under the tongue of the subject as part of a stress test in accordance with the present disclosure.

In aspects, the stress test may include administering a bolus of an ACE inhibitor orally to the subject, and/or a bolus of enalapril or enalaprilat intravenously to the subject.

In aspects, a stress test may include having a subject breath air that is a different temperature than that of the skin of the subject and/or have air of a different temperature blown onto the skin thereof, so as to elicit a strong ANS response. In aspects, a warm air gust may substantially stimulate more of the parasympathetic system of the subject and a cold air gust may stimulate the SNS of the subject.

In aspects, the stress test may be devised so as to elucidate a differential response between aspects of the sympathetic state of a subject, a branch of the sympathetic nervous system, and a parasympathetic state of a subject, an initial neural state, etc. One non-limiting example may include assessment of acetylcholine nerve states separately from that of epinephrine nerve states, or that of substance P, cholinergic, and/or vesicular acetylcholinetransporter (VAChT) nerve states. In aspects, such differentiation may be determined by assessing neural traffic at a plurality of sites on the body such as near a particularly sweaty region of the skin to assess acetylcholine nerve states, or near a muscular structure for assessment of epinephrine related nerve states, simultaneously so as to assess relationships there between, near an erogenous zone for assessment of cholinergic or vesicular acetylcholinetransporter related nerves, and the like. Comparison between a plurality of responses recorded over alternative regions of skin of a subject may be advantageous for extracting independent measures of the functionality of one or more branches of the autonomic nervous system, sympathetic nerves, parasympathetic nerves, somatosensory nerves, or the like.

In aspects, as part of a stress test, or in preparation for a stress test, one or more eye drops may be administered to an eye of the subject, such as in the form of an eye drop. Some non-limiting eye drops that may be considered include saline-containing drops, and/or drops containing one or more steroids, antihistamines, sympathomimetics, beta receptor blockers, parasympathomimetics, parasympatholytics, prostaglandins, non-steroidal anti-inflammatory drugs (NSAIDs), antibiotics, antifungal, or topical anesthetics.

In aspects, a method may include delivery of an alpha or beta agonist or antagonist intravenously or intra arterially to a subject and following/monitoring the response of one or more nerves with a system, device, or method in accordance with the present disclosure to determine the state, response, suitability for treatment, thereof, etc. Such a stress test may include monitoring the activity for a period of greater than 30 seconds, greater than 1 minute, greater than 5 minutes, greater than 15 minutes after initiation of the stress test, etc. The analysis may include comparing the neural response associated with one or more tissue sites of the subject, generating an overall assessment of traffic (e.g. an assessment of tone, afferent traffic, efferent traffic, etc.), for use in the comparison, etc. The analysis may include mapping the input strength—output intensity of the relationship between the stress test input and the monitored neural response, or surrogate thereof.

The method may include subsequent administration of a beta or alpha antagonist or agonist to the subject, to monitor the response of one or more neural circuits, traffic, etc. under the changing pharmacological conditions caused by the stress test. The differential response of the subject between a first and subsequent test may be advantageous to assess a neuroendocrine relationship within a neural circuit of the subject (e.g. such as within a renal neuroendocrine circuit of the subject, a pancreatic circuit, a carotid circuit, etc.). The magnitude of the differential response as related to one or more of the physiologic parameters, etc. may be a suitable parameter for diagnosing a disease state of the subject, assessing the suitability of the subject for a treatment, predicting the responsiveness of the subject to a treatment, etc.

The method may include monitoring, via an HMD, one or more ocular and/or facial parameters of the subject (e.g. gaze, ocular hydration, ocular blood flow, pupil properties, pupil diameter, iris properties, iris features, iris muscle strain, iris sphincter muscle strain, iris dilator muscle strain, iris crypt movement, retinal properties, retinal blood flow, ERG, facial EMG, EOG, facial neural traffic, tissue perfusion, sweating, fatigue, facial expressions, tissue analyte levels, etc.), so as to contribute to the generation of the metric. A system in accordance with the present disclosure may be configured to capture physiologic parameters at a plurality of sites on the body of the subject so as to obtain signals from different tissue types, to capture differential SNS/PNS signals from tissue sites, etc. Such information may contribute to the generation of the assessment.

In aspects, such an approach may be advantageous to assess and/or troubleshoot a disease state, treatment, medication effect, etc. on a subject, troubleshooting and/or state characterization of various autonomic functions of a subject, individual assessment of sympathetic and parasympathetic state of a subject, or the like.

In aspects, the posture of the subject may be altered during the monitoring (such as via a tilt table), alteration of a peripheral resistance (e.g. such as via application/removal of a tourniquet, etc.), a sudden rise or fall in a peripheral resistance, a change in local barometric pressure, a sudden decompression, a sudden compression, a sitting to standing movement, a Valsalva maneuver, an exercise, or the like may be performed during monitoring to further assess aspects of the ANS of the subject.

In aspects, a stress test may include applying a visual, olfactory, gustatory "taste", and/or audible field or experience to a subject, while monitoring a physiologic response, a neural response, or a surrogate thereof. Such sensation of sight, smell, sound, taste, or the like may evoke an ANS response from individuals. SNS or PNS outflow associated with such a response may be monitored with a system, device, patch, and/or method in accordance with the present disclosure. Abnormal responses may be determined during such tests, the abnormal response being an indication of a disease state, suitability, or unsuitability for a treatment, etc. A visual, olfactory, and/or audible field may be applied to the subject at least in part with an HMD in accordance with the present disclosure.

The HMD may be configured to deliver a series of visual fields, lighting conditions, changing lighting conditions, images, video sequences (with or without audible inputs), left/right differentiated images, disturbing images, inviting images, product suggestions, audible fields, left/right differentiated audible fields, sudden/startling sounds, images, and/or nonspecific visual stimuli, mis-matched visual and auditory fields, to the subject as part of a stress test, during use, during a physiologic calibration procedure, or the like each in accordance with the present disclosure. Such input may be advantageous to establish a standard ANS responsiveness for the subject, lull the subject into a state of visual-auditory sensory deprivation, generate a standard response state, substantially remove the influence of and/or control visual/auditory artifacts experienced by a subject during a stress test in accordance with the present disclosure, etc. The response of the subject to such inputs may be simultaneously monitored by one or more sensors in accordance with the present disclosure. In aspects, an electroencephalogram of the subject may be monitored before, during, and/or after the stress test, presentation, etc.

In aspects, the HMD may be configured to deliver an audio/visual presentation to the subject, the audio/visual presentation arranged so as to lull the subject into a standard state of awareness (e.g. to slowly lull the subject into a sensory deprived state, to establish a baseline ANS activity state for the subject, etc.) with possible sudden/startling stimuli of audible, and/or visual origins. In aspects, the audio/visual presentation may include presenting a changing light field to the subject (e.g. a changing color field, a color gradient field, a changing ambient intensity, a flicker-rate, a changing flicker-rate, etc.), so as to assess a physiologic response thereto. The HMD may be configured to monitor one or more ocular parameters, facial expressions, facial muscle tone, perfusion, retinal blood flow, etc. during the presentation. Such audio/visual presentations may be applied before, during, and/or after one or more stress tests and/or procedures each in accordance with the present disclosure. Such audio/visual presentations may be suitable for assessing the state of the ANS of the subject before, during, and/or after a stress test, a procedure, a neuromodulation test, an ablation, etc.

In aspects, a stress test in accordance with the present disclosure may include application of a thermal input (such as heating, cooling, or regulating the response of), a region of skin of a subject, airflow around a subject, air breathed by a subject, or the like. In aspects, such a stress test may be performed by a system, or device in accordance with the present disclosure, the device including a thermal regulating unit (e.g. a thermoelectric device, a Peltier device, an endothermic reactive specie, an exothermic reactive specie, a temperature regulating gel, a fluid cooling/heating system, etc.). In aspects, the device and/or system may be configured to monitor the generated afferent traffic associated with the thermal stress that may adjust the SNS/PNS differential relationship in the body, an SNS/PNS output or surrogate thereof associated with the changes in ANS caused by application of the thermal stress state, etc. Such outflow may be monitored with one or more devices in accordance with the present disclosure (at an alternative site on the body, at the same site on the body as the thermal stress application, etc.). An associated system may be configured so as to monitor changes in PNS related outflow, SNS related outflow, somatosensory response, etc. and determine the relationships associated therewith. In aspects, the system may include one or more sensors located within or near to the thermal regulating site, the sensors configured to monitor afferent traffic generated in the skin by the change in thermal load thereupon. Simultaneously, additionally, alternatively, or in combination, the system may include one or more sensors each in accordance with the present disclosure, each sensor located at one or more alternative sites on the body, configured to monitor corresponding outflow from the ANS caused, at least in part by the stimulus. Such a system may be advantageous to map correlating ANS inputs (e.g. afferent traffic from various ANS coupled organs, eye, skin, audio, scent, taste, thermal, tactile skin response, etc.), to changes in the ANS outflows (e.g. SNS outflow, PNS outflow, changes in branches, changes in physiologic parameters associated with the ANS outflow, such as changes in HR, HRV, BP, etc.). By varying the stimulatory loads during stress tests, a processor programmed with an appropriate stress evaluation algorithm may be suitably configured to generate a transfer function for the subject in this regard (e.g. a transfer function, a SIMO transfer function, a MIMO transfer function, or the like relating the stress inputs to the monitored afferent, efferent, and outflows). Such a transfer function may be suitably derived and/or compared between tests performed before/during/after a medical procedure, etc. Changes in the test observed after a procedure may be used to determine the extent of the procedure, etc.

In aspects, a stress test may include application of a tactile input to one or more regions of the skin of a subject. Such tactile input may include penetration, penetration-like movements, vibratory movement, pinching, burning, flicking, stroking, lateral movements, rotary vibrations, or the like. In aspects, the site of the excitation may be selected so as to excite particular regions of the ANS (e.g. such as exciting the parasympathetic nervous system, via tactile input to one or more parasympathetic receptors located near to the ear, etc.).

In aspects, energy, tactile input, massage, or the like may be applied to a carotid sinus, carotid body, etc. In aspects, energy delivery may be provided by a device in accordance with the present disclosure. In aspects, a systemic variable, such as a change in blood pressure, heart rate, heart rate variability, neural activity, skin SNA, etc. (such as may be monitored by a device in accordance with the present disclosure) may provide a global feedback that the stimulus, energy input, etc. was delivered to the carotid sinus, and reflect the degree of excitation thereof for the subject, one or more devices in accordance with the present disclosure may be arranged on the body so as to monitor an associated change in the ANS, the PNS, the SNS, an overall change, in a branch of the ANS, such as a skin branch, may be representative of the ANS, SNS, and/or PNS outflow generated therefrom. In aspects, such a stress test may be used to determine the suitability of a subject for a procedure, a sympathectomy, a neuromodulation implant, a neural ablation procedure, a renal denervation procedure, etc.

In aspects, the amount of change in one or more of the monitored signals, whether the signals recovered near to the original values after the test, how quickly the signals changed, recovered, differential changes between signals, etc. may be considered in deciding if the subject is a suitable candidate for a procedure, a therapy, an implant, or the like.

In aspects, a stress test may include altering an environment around a subject, such as changing the temperature, ambient light levels, humidity, airflow, etc. In aspects, such ambient changes may be monitored with a sensor in accordance with the present disclosure, the magnitudes of the changes compared against the response in the generation of a transfer function, a response map, etc.

In aspects, the purpose of such stress tests may be to quantify a subject response thereto, to establish a neuroendocrine transfer function relating various aspects of a neural circuit, and/or neural functional relationship for a subject at the time of testing. Such stress tests may be used to determine a "control window" relating a neural influence on a function of an organ, the control window meaning the range of influence that a neural input can have on the function of an organ in the subject, or a portion thereof. The stress tests may be used to determine the "set point" of a neurological tone in the subject relating to such a control window. The stress tests may be used to determine a sensitivity of the subject to a range of "stressors". The stress tests may be used to determine a control margin (i.e. a differential range between the set point and a maximum or minimum limit of the control window for the subject at the time of the test, etc.). In aspects, the control margin may be only relatively related to an overall control margin due to the time scale of the test. In a non-limiting example, a test in accordance with the present disclosure may demonstrate a characteristic change in blood pressure of the subject during the test, which may be indicative of a larger blood pressure change for a prolonged test, etc. The test may also result in changes in physiologic processes and organ function, which may lead to long term changes in blood pressure, which may not sufficiently manifest during the timescale of the stress test, or associated monitoring period. Thus a relative assessment of the control window, set point, and/or control margin for a subject may be determined with such stress tests, etc. In aspects, subject responses measured with a plurality of instruments, collected from a group of physiologic parameters, may be monitored to generate the relative metric.

According to aspects, there is provided a method for assessing the neural—renal function of a subject. The method includes applying a stress test to a subject in accordance with the present disclosure, monitoring one or more physiologic parameters in accordance with the present disclosure, and calculating one or more performance metrics for the subject, the performance metric representing a quantitative value of the neural-renal function of the subject.

In aspects, the method may be used to select a subject for suitability of a drug therapy, a surgical procedure, and/or an interventional procedure, and/or to assess the outcome, dosage level, and/or to determine the window of dosing for the subject.

In aspects, the renal-neural function of a subject may be assessed by applying a plurality of stress tests to the subject (e.g. a baroreceptor stress test, a warming or cooling of tissue, a cold pressor stress test, a cold pressor stress test applied to the forehead of the subject, the wrist of the subject, the hand of the subject, the nose of the subject, a cold air breathing test, a Valsalva test, a breath hold test, a head-up tilt test, administration of a medication, etc.). The metric being generated by comparing one or more physiologic parameter responses to the plurality of stress tests.

In aspects, a non-limiting example of a method for assessing neural-renal function of a subject in accordance with the present disclosure may include administering a dose of a medication (e.g. an antihypertensive medication, an adrenergic antagonist, agonist, etc.) to the subject and monitoring a response thereto.

In a non-limiting example of such a method, a subject is positioned in a supine posture, and instrumentation for monitoring one or more physiologic parameters is/are coupled to the subject. A beat-to-beat blood pressure monitor (e.g. a Finapres®, a Nexfin® system, a patch based blood pressure system in accordance with the present disclosure, or the like) is coupled to the subject during the test to register a blood pressure reading therefrom. In aspects, a renal blood flow monitoring apparatus (e.g. an ultrasound imaging system, a Doppler flow meter, etc.) is coupled to the subject during the test to register a renal blood flow reading therefrom. In aspects, a urinary flow monitor (e.g. a urinary flow catheter, a bladder filling ultrasound imaging system, etc.) is coupled to the subject during the test to register or establish a urinary flow rate therefrom. In aspects, an initial blood sample may be drawn from the subject, which is tested for circulatory analyte concentrations (e.g. water, saline, renin, angiotensin, epinephrine, dopamine, etc.) prior to a stress test.

The stress test is administered to the subject and one or more of the physiologic parameters are monitored so as to determine the response of the subject thereto. In aspects, one or more processes in the body may be monitored during the stress to determine one or more organ or subsystem responses to the associated test. Some non-limiting examples of processes that may be monitored include renal nerve traffic, efferent renal nerve traffic, afferent renal nerve traffic, renal tubule function, macula densa function, right axis deviation (i.e. increased workload of the right ventricle), glomerular filtration rate, urine production rate, sodium excretion rate, hypothalamus and/or pituitary gland activity (e.g. such as via fMRI, systemic hormonal release, etc.), cardiac functional changes (e.g. heart rate, blood pressure, cardiac output, stoke volume, etc.), gastrointestinal processes, central nervous system activity, or the like.

In one non-limiting example, the stress test includes intravascular administration of a dose of an antihypertensive medication. During the antihypertensive stress test, the blood pressure, sympathetic neural traffic, renal neural traffic, pupil diameter, and/or circulating analyte levels of renin, angiotension, dopamine, etc. of the subject may decrease, while the urine excretion rate, sodium excretion rate, vascular diameter, venous capacity, and/or renal blood flow may increase during the test. In aspects, a second blood sample, taken at predetermined time period after initiation of the stress test may be taken from the subject. The second blood sample may be compared against the first blood sample to determine how circulating analyte levels changed during the stress test. Such changes may be compared against other metrics to determine the sensitivity of the subject to the stress test.

Some non-limiting examples of analytes that may be analyzed and compared in the blood samples include blood urea nitrogen, calcium, chloride, carbon dioxide, creatinine, glucose, potassium, sodium, albumin, phosphorus, alkaline phosphatase, alanine aminotransferase, renin, angiotensin, aspartate aminotransferase, protein, testosterone, prolactin, progesterone, dopamine, aldosterone brain natriuretic peptide, atrial natriuretic peptide, plasma renin activity, etc. Changes in analyte levels during the stress test may be used in the generation of one or more metrics.

In aspects, the blood sample draw may be performed periodically during the test or pseudo continuously with a corresponding microdialysis system. Such a configuration may be advantageous for assessing dynamics of the system that take place during the stress test(s).

In aspects, a metered dose of the antihypertensive medication may be administered to the subject, a dose may be varied during the test, a sequence of doses with varied bolus may be administered, etc. during the test, so as to generate a dose response curve for the subject between the medicament and the measured response variables. From the monitored responses, a dose response curve, a characteristic dynamic of the test results, or the like may be extracted and used to generate the metric. In one non-limiting example, the peak drop in blood pressure of the subject during the stress test may be used as an indicator of the sensitivity of the blood pressure of the subject to the mechanism of action of the medicament. A patient may be considered sensitive if the blood pressure changes by more than 1%, more than 5%, more than 10%, more than 20%, during the stress test. A patient may be considered sensitive if the renal blood flow, urine flow rate, sodium excretion rate, pupil diameter, etc. changes by more than 1%, by more than 5%, or by more than 10% during the stress test.

In aspects, such an antihypertensive stress test may be used to classify a subject as more or less sensitive to the mechanism of action of the medicament used in the stress test. The subject sensitivity may be a strong indicator of the successful long-term treatment of the subject with the medicament, or a procedure that targets one or more aspects of the same mechanism.

In one non-limiting example, a subject that is classified as "sensitive" to an antihypertensive stress test performed with an adrenergic receptor antagonist, a noreprinephrine displacing agent, one or more boluses of guanethidine, or the like may be a suitable candidate for a renal denervation procedure. In aspects, the subject sensitivity to such a test may correlate strongly with the effectiveness of a renal denervation procedure on the subject. Thus the subject sensitivity to an antihypertensive stress test in accordance with the present disclosure may be used to select patients for a renal denervation procedure.

In aspects, the stress test may include administering a baroreflex test, a thermal test, a hepatorenoreflex test, or the like each in accordance with the present disclosure to the subject, separately or in conjunction with a corresponding medication based test. In aspects, the comparative variation in the subject responses to the different tests may be a strong indicator of the sensitivity of the subject to a range of potential procedures, including renal denervation, hepatic stimulation, carotid body ablation, baroreceptor stimulation, etc. Such stress tests may be used to select patients for such procedures, test the expected magnitude of the response of the subject to one or more such procedures, or the like.

In aspects, one or more portions of a response (e.g. a renal functional component, a stimulatory component, a sympathetic reflex component, etc.) may be extracted via simultaneous measurement of a plurality of corresponding physiologic parameters (e.g. parameters associated with renal function, with baroreceptor function, with sympathetic outflow, parasympathetic outflow, somatosensory function, hepatic receptor function, etc.). Based upon the serial interplay between the measured responses, a functional view of the different subsystems of the subject may be quantified. After quantification, the targets for therapy, procedural intervention, etc. may be selected so as to establish a rational treatment plan for the subject.

In aspects, a hepatorenoreflex test may be performed as part of a stress test on the subject. The hepatorenoreflex includes stimulating and/or blocking receptors in the hepatic artery of the subject, and monitoring one or more physiologic parameters associated with renal function of the subject. Such a test may include direct stimulation of the hepatic receptors (such as via application of energy or a medication thereto), or physiologic stimulation (such as via changing local sodium content of the blood therein, having the subject consume a beverage or food which is high/low in sodium, etc.). In aspects, if the renal function does not substantially change during such a test, the neural connection between the hepatic receptors and the kidney may be non-functioning, successfully ablated, etc. In aspects, if the renal function responds in a hypersensitive manner to the stimulation, the subject may be a suitable candidate for an ablation procedure, etc.

In aspects, if a subject is found to be substantially unresponsive to a blood pressure increasing test, a baroreceptor reflex test, etc. the subject may be a strong candidate for a renal denervation procedure, as the differential control margin between the sympathetic set point and the maximum range for the subject may be substantially small (e.g. by corollary the differential control margin between the sympathetic set point and the minimum range for the subject may be substantially large).

In aspects, a combination of tests may be administered to the subject to determine the gain or control window of the subject along with the natural set point of the control variable (e.g. autonomic tone, renal nerve activity, etc.), to determine the suitability of the subject for a renal denervation procedure. In aspects, the ideal subject for such a procedure may have a wide control window, with an initial set point located near to the maximal range of the control window (i.e. such that there is maximal potential to drop blood pressure in the subject via application of the target procedure).

In aspects, a method for following up on the treatment of a subject may include performing a stress test in accordance with the present disclosure and comparing the results of the stress test against a previously performed, and/or pre-treatment stress test. Such comparison may be used to assess changes in the control window, movement of the set point, changes in organ function, neural function, etc. associated with the therapy applied to the subject. The results of such follow up stress tests may be used to alter therapy, manage medication dosages, assess dosage windows, introduce a new therapeutic component to the overall therapy, etc.

In aspects, a metric relating to the sensitivity of the subject measured during a stress test in accordance with the present disclosure may include assessing a dynamic characteristic of the subject response during the test, such as a rate of change of a physiologic assess temporal dynamics of the test response, a peak response, a settling parameter, an overshoot of the response before settling, a stochastic aspect of the response, a flutter in the response, an overall change in value, etc. The metric or a plurality of metrics may be assessed to determine the sensitivity of the subject, an organ, a functional aspect, or a subsystem of the subject, to the stress test.

In aspects, a method for determining the extent of a renal denervation procedure includes performing one or more stress tests (e.g. a baroreceptor reflex test, a cold pressor test, a breath hold test, a salt load test, etc.), which are known to affect kidney function via a predominantly neural pathway (e.g. via a sympathetically or afferent mediated process in the body over the time course of the test). The stress test may include monitoring one or more renal functional parameters (e.g. renal blood flow, afferent renal traffic, urinary excretion rate, sodium excretion rate, renal perfusion, renal vasospasm, renal analyte spillover, etc.), direct neural traffic, sympathetic neural outflow, contralateral kidney function, or the like in response to the stress test. If the response is blunted, as compared against a population norm, a pre-procedural test on the subject, etc. then the procedure may have been at least partially completed. If the response is entirely blunted, than the renal neural interconnection to the CNS has been substantially abolished in the subject. If the response is only partially blunted, the procedure was partially completed and/or the nerves have begun to reinnervate the kidney.

According to aspects there is provided, a method for assessing the neural regrowth in a subject following a renal denervation procedure. The method includes comparing a follow-up stress test to a previously performed, post procedural stress test on the subject. Comparison of the results of the follow-up stress test to the post procedural stress test may be used to determine the extent of reinnervation of the organ post procedurally. If the results from the follow-up stress test illustrate a similarly blunted response to the results obtained by the post-procedural stress test, the organ (e.g. kidney, pancreas, liver, etc.), may be similarly innervated (e.g. no substantial nerve regrowth). If the follow-up stress test results illustrate a statistically significant change in the stress response compared against the post-procedural stress test, then a substantial degree of reinnervation of the organ may be occurring (e.g. substantial levels of nerve regrowth are occurring).

According to aspects there is provided, a method for assessing the adaptation of a physiological process of a subject to a therapeutic intervention (e.g. a medication based therapy, a change in medication, a procedure, a neuromodulation procedure, a neurostimulator implant, an ablation procedure, a renal ablation procedure, etc.). The method includes assessing one or more physiologic parameters of a subject during a stress test, the stress test applied to the subject after a period of time following the initiation, or alteration of a therapeutic process for the subject.

In aspects, a non-limiting example of a method for assessing the sensitivity of renal tissue to circulating epinephrine following a renal denervation procedure, includes applying one or more doses of a neurotransmitter, and adrenoceptor agonist, etc. to the subject via an intravenous injection, monitoring one or more renal functional changes, and/or physiologic surrogates thereof to collect related physiologic data, and assessing the changes in the physiologic data to assess a functional relationship, a dose response curve, etc. between the dose and the physiologic response(s). If the functional relationships are outside of a normal range, or have changed between the present test and a previous test, the epinephrine sensitivity of the renal tissues may have substantially changed after the procedure. In aspects, such elevated circulating epinephrine sensitivity may be a strong indication that a previously applied renal denervation procedure was successfully completed.

In another non-limiting example, a method for determining a change in the sensitivity of an atrial natriuretic peptide (ANP) receptors in the body to circulating atrial natriuretic peptides includes coupling a subject to a kit for monitoring blood pressure, heart rate, renal function, sympathetic outflow, vascular perfusion, ocular response, or the like and collecting one or more physiologic signals therefrom during a stress test, and administering an atrial natriuretic peptide receptor agonist/antagonist to the subject (e.g. via an intravenous injection, an intra-arterial injection, etc.). If the functional relationships are outside of a normal range, or have changed between the present test and a previous test, the atrial natriuretic peptide receptor sensitivity in the subject may have substantially changed after the procedure. In aspects, such detection of elevated atrial natriuretic peptide sensitivity may be a strong indicator that a previously applied renal denervation procedure was successful.

According to aspects, there is provided a method for assessing an afferent receptor contribution, or indication of the afferent receptor contribution to a disease state in an organ, the method including coupling one or more elements, components, systems, or the like in accordance with the present disclosure, to the subject so as to monitor one or more physiologic signals during an associated stress test, administering an afferent stress test to the subject in accordance with the present disclosure, measuring the physiologic signals in response thereto, and generating a metric associated with the response. In aspects, such an afferent stress test may include stimulation and/or blocking of one or more receptors, baroreceptors, carotid baroreceptors, cardiopulmonary baroreceptors, renal baroreceptors, chemoreceptors, renal chemoreceptors, hepatic chemoreceptors, carotid chemoreceptors, gastrointestinal receptors, parathyroid receptors, or the like. In aspects, the stimulation and/or blocking of the receptors may be applied directly (e.g. such as via direct application of energy, and/or a chemical agent to the targeted receptor sites, etc.), or physiologically (e.g. such as by introduction of a stimulating agent, by influencing the environment around the targeted receptor sites, etc.).

In aspects, in a non-limiting example relating to assessment of the renal function of a subject, the afferent stress test may include applying an excitatory/inhibitory stressor to a renal pelvis, a ureter, a renal vein, a bladder wall, or the like within the subject. In aspects, the excitatory/inhibitory stressor may be provided by a focused ultrasound delivery (e.g. a low level focused ultrasound signal for stimulatory effect, a mid-level focused ultrasound for a temporary inhibitory effect, etc.), etc. In aspects, the excitatory/inhibitory stressor may be provided by local electrical stimulus to a renal pelvis, a ureter, a renal vein, a bladder wall, or the like within the subject. In aspects, the excitatory/inhibitory stressor may be provided by an excitatory/inhibitory chemical agent, administered to one or more sites within a kidney, within a renal pelvis, a ureter, a renal vein, a bladder wall, or the like within the subject. In aspects, the chemical agent may be selected so as to generally affect receptors in the target site, or selected so as to selectively interact with specific sensory receptors in the target site (e.g. such as via application of a capsaicin, etc.).

In aspects, a non-limiting example of an afferent stress test for assessing the renal neuroendocrine system of a subject as related to treating a hypertensive disease state in the subject may include, applying a stimulatory and/or excitatory input to one or more of the target sites (e.g. via ultrasound energy delivery to a renal pelvis, via electromagnetic energy delivery to a renal site, via low level magnetic stimulation to a renal site, via thermal stimulation of the renal pelvis, via chemical delivery to the renal pelvis, etc.), while monitoring one or more physiologic parameters including the blood pressure of the subject (e.g. via beat to beat monitoring method, a patch/module pair in accordance with the present disclosure, etc.), and one or more physiologic indicators of sympathetic outflow (e.g. skin sympathetic outflow, CNS activity, ocular neural outflow, etc.).

In aspects, the method may include comparing the stimulus level to the physiologic indicator of sympathetic outflow (e.g. so as to normalize the response curve for the subject, to standardize the test results, etc.). In this non-limiting example, the physiologic indicator of sympathetic outflow may be used to standardize the test results for the subject, thus improving selectivity when comparing the results against a population norm. Such standardization may be advantageous to reduce test variation and/or uncertainty associated with stimulation level (i.e. capture of receptors with respect to the stressor application thereto, relationship between the stimulation and the sympathetic outflow, etc.), as compared to only assessing a physiologic response to the stressor.

In aspects, a plurality of metrics may be generated from the synchronously measured outputs. The metrics may be used to extract sub-system functional relationships from the subject, as they pertain to the overall assessment. Such relationships may be advantageous to highlight the contribution to the subject response from sub-systems (e.g. what portion(s) of a response are neural, renal functional, input variation, output variation, neural outflow controlled, CNS controlled, etc.). Such relationships may be advantageous for determining a path for treating the disease state of the subject (i.e. so as to provide quantitative evaluation of function for selecting procedures, drug programs, dosages, etc. personalized to the nature of the subject response to the stressors, and/or changes in response versus previous tests, etc.). In one-non-limiting example, a plurality of receptors are stimulated in a subject as part of a stress test in accordance with the present disclosure, sympathetic outflow of the subject is monitored at a plurality of sites on the subject (e.g. via ocular feedback, skin neural activity), and via changes in vital signs (e.g. blood pressure, heart rate, heart rate variability, tissue perfusion, skin piloerection, one or more ipsilateral and/or contralateral renal functions, etc.). The relationship between the sympathetic outflow as measured at one or more skin sites, may be compared against the changes in blood pressure to assess a sensitivity between renal-afferent instigated sympathetically mediated blood pressure changes in the subject, the changes in renal function may be compared against the sympathetic outflow as measured via the ocular feedback, as to assess the relationship between ANS stimulation in the subject and changes in renal function, or the like. Such configurations may be advantageous for quantitatively compensating for the unknown inputs to the system (e.g. how many/sensitivity of renal receptors stimulated, resulting afferent traffic, etc.), but also for extracting intermediate variables within the reflex chain under study (e.g. such as sympathetic or parasympathetic spillover to other organs in the subject during the test, etc.), relationships between key outputs (e.g. comparison of renal functional changes versus blood pressure changes, etc.), and/or temporal changes in functionality (e.g. emotionally influenced changes, circadian rhythm based changes, therapeutic changes, neuroplastic remodulation, etc.), so as to assess key organ function in the reflex chain as potential targets for interventional treatment of the disease.

In one non-limiting example, the renal stimulation may result in a rise in blood pressure of a subject, indicating that ablation of the afferent renal nerves may advantageously influence the blood pressure of the subject. A renal stimulation resulting in a decrease in blood pressure of a subject, may be an indicator that ablation of afferent renal nerves may not reduce blood pressure of the subject.

In aspects, a method in accordance with the present disclosure may include monitoring the peripheral neural traffic directly with a locally placed catheter (e.g. such as along the renal artery, along a ureter, within the parenchyma of the kidney, or the like for a renal procedure). Such neural traffic may serve as an additional physiologic parameter relating to the functional assessment of the neural endocrine system of the subject under study. The input-output relationships may be developed in conjunction with the neural traffic readings in order to further remove unknowns in the system, and/or to establish functional relationships between input and neural traffic, neural traffic and other physiologic changes, etc.

In aspects, a method in accordance with the present disclosure may be used to determine the extent of a procedure, extent of a drug therapy, or the like each in accordance with the present disclosure. If the input stressor (e.g. renal stimulus, baroreceptor stimulus, etc.) does not substantially affect the measured physiologic parameter (e.g. renal functional parameter, vital signs, blood pressure, neural outflow, ANS function, or the like and/or surrogates thereof), post procedure (e.g. as relating to an associated blocking procedure, a renal denervation procedure, etc.), then the procedure may have substantially achieved the desired effect. In a non-limiting example, where the follow on stress test is performed on a subject several weeks, months, or years after the procedure, if the input stressor does not result in a substantial change in the measured physiologic parameter, then it may be concluded that the procedure was durably performed on the subject.

In aspects, a stress test in accordance with the present disclosure may include application of a thermal input to the subject (e.g. altering of the temperature of a site on/in the body of the subject, a cold pressor test, a warm pressor test, etc.) in accordance with the present disclosure. In one non-limiting example, a thermal input to the subject may be regulated with a Peltier type device (e.g. a thermoelectric unit interfaced with the tissue at a site on/in the body of the subject so as to influence the temperature thereof). The thermal input may be configured so as to controllably change the temperature at the site on/in the subject, so as to generate a temporal temperature profile at the site, so as to cause a known heat flux at the site, etc. In aspects, the device may include a plurality of control sites, so as to interact with the subject with conflicting temperatures (hot at one site, cold at another site), or to apply the thermal input over a larger tissue surface (e.g. an array of smaller thermoelectric devices so as to alter the thermal input over a large region of tissue of the subject, etc.). Such thermal inputs may be strategically applied to different regions of the body and/or tissue types so as to evoke specific responses therefrom. Multi-site and/or sequential application of such thermal inputs may be advantageous to evaluate the specific evoked responses from the subject, and to assess alternative reflex pathways on the subject during the associated stress tests.

Some non-limiting examples of thermal input sites on a subject include the forehead, ocular region, temple, ear, tongue, mouth, nasal lining, neck, nose, lips, chin, axilla, elbow, cubital fossa, wrist, hand, palm, fingers, back of the hand, a nipple, abdomen, genital, lower back, sacral region, leg, foot, etc. Such thermal sites may be coordinated ipsilaterally, and/or contralaterally from each other (e.g. applied to wrists, hands, etc.), or at multiple sites on the body. Such thermal inputs may evoke substantially different responses from the subject based upon the location and temporal history of temperature at the site of the inputs. Thermal input to glabrous or erotic tissues of the subject may evoke strong parasympathetic reaction from the subject, while thermal input to hairy tissue may evoke a strong sympathetic reaction from the subject. An ocular assessment system in accordance with the present disclosure may be configured to monitor iris and/or pupil changes in the subject so as to determine an extent of the stimulation of the parasympathetic and/or sympathetic input to the subject during the associated stress test.

In aspects, the thermal control units may include one or more sensors in accordance with the present disclosure so as to measure neural activity, tissue temperature, tissue perfusion, piloerection, or the like associated with an associated stress test and/or subject monitoring session.

In aspects, a drug may be administered to the subject so as to perform a stress test and/or to alter functionality of one or more aspects of the reflex chain associated with the stress test (e.g. so as to enhance and/or block action of one or more sub-systems associated with the reflex response to the stress test). Some non-limiting examples of such drugs include anesthetic agents, which may strongly influence the test outcomes.

In aspects, the duration of the test (seconds, minutes, hours, days, etc.), may be determined so as to balance the test duration against the physiologic functional changes of interest with the test. In one non-limiting example, functions such as renal blood flow, renin secretion, and renal tubular sodium resorption may change quickly during a test, while the influence of those parameters on systemic variables (such as blood pressure), may take time to manifest themselves. An associated stress test configured so as to monitor quickly changing variables may be substantially shorter in duration than a test configured to monitor the longer term changes in the system under study.

In aspects, a stress test in accordance with the present disclosure may include directly influencing renal neural traffic and/or renal neural traffic driven processes (e.g. changes in renin secretion, dopamine secretion, renal blood flow, glomerular filtration rates, urinary sodium excretion rates, glomerular resistance (efferent arteriole, afferent arteriole, capillary hydrostatic pressure gradient, capillary ultrafiltration coefficient), etc.), and monitoring one or more systemic, blood analyte levels, and/or renal functions associated therewith.

In aspects, a cardiopulmonary baroreceptor reflex test may be administered to the subject. The blood pressure response to the baroreceptor stimulation may be monitored during the test and a metric associated with the sensitivity of the blood pressure change in the subject to the test generated (e.g. low, mid, high, graded response, etc.). A good candidate for a renal denervation procedure may demonstrate a poor response to the baroreflex sensitivity test and/or a strong response to a vasodilation test (such as may be determined with a stress test in accordance with the present disclosure).

Some non-limiting examples of stress/emotional reflex tests that may be performed on a subject in accordance with the present disclosure include a visual input, an audible input, application of a fear, shock, pleasure, disgust, inducing image/sound (e.g. such emotional responses may alter sodium excretion and urine processes), electric shock, application of an air jet to a site on the skin (e.g. at a thermal stress site), cold/warm air breathing, breathing air of different relative temperature to the rest of the body, cold/hot pressors (such as to the forehead, nose, back of the neck, hands, wrist, feet, genitals, ear, tongue, etc.), breathing hot/cold air versus skin cold tests (different receptor reflexes depending on the relative temperatures between the body and the air), application of cardiopulmonary stress, a Valsalva maneuver, a breath hold (with/without pressure, with/without strong abdomenal tension, etc.), a head up/down tilt test, a head out of water test, hand clenching, tourniquet application to lower limb, a temporary ganglion blockade (e.g. via cold, hot, electrical block, chemical block, ultrasound, focused radio frequency energy, low intensity magnetic field application, etc.), a renoreflex test, direct simulation of renal nerves and response (hot, ultrasound, electrical, chemical, magnetic field, etc.), one or more afferent neural traffic tests, direct or physiological stimulation of renal pelvis, renal vein nerves, uretral occlusion (such occlusion may increase renal pelvis pressure and thus drives afferent traffic, even pressures as low as a few mmHg may influence afferent traffic, etc.), uretral analyte levels (e.g. changes in sodium, urea, substance P, etc. may influence afferent nerve traffic), renal vein block (may induce large changes in afferent nerve traffic), local analgesic application to a receptor site (e.g. lidocaine application to the renal pelvis can significantly decrease afferent traffic, etc.), a baroreceptor reflex test, a baroreceptor unloading or stimulation test, direct pressure-based tests (i.e. changing the pressure on the baroreceptors), vibration or thermal influence on a baroreceptor, application of suction to a baroreceptor (e.g. a means of baroreceptor unloading), application of energy to a carotid and/or cardiopulmonary baroreceptor (e.g. impulses inhibit RNA and suppress renin secretion rates), sectioning, suction, extension, and/or cold blocking of a receptor, blocking/stimulation of an atrial receptor (e.g. unloading of cardiopulmonary baroreceptors by passive head-up tilt may increase renin secretion rate in humans with sensitivity and response being indicative of procedure suitability, procedure completion, etc.), application of non-hypotensive hemorrhage (e.g. may result in increased renin secretion rate), renal baroreceptor stimulation (e.g. may increase sensitivity of renin release via other renal nerve activity based mechanisms), venous reflex response (e.g. sympathetically mediated reflex venoconstriction that occurs after deep breath, Valsalva, mental arithmetic, or cold pressor tests on a limb of a subject), common carotid artery occlusion (e.g. may increase efferent renal nerve traffic), grooming, massage, air jet stress application (e.g. may increase efferent renal traffic and induce systemic and regional hemodynamic responses along with renal vasoconstriction), or the like.

In aspects, a plurality of tests may be applied to the subject to assess substantially orthogonal reflex responses thereto. In one non-limiting example, a carotid baroreceptor reflex-mediated test may have little effect on renal blood flow, while an air jet stress test may have a massive influence on renal blood flow, yet both tests may significantly affect the blood pressure of a subject. In aspects, the difference in renal function measured during the two tests may be used to determine the sensitivity of a subject to changes in renal nerve traffic that occur differently during the tests.

Some non-limiting examples of stress tests that may result in an overall increase in renal nerve traffic and produce antidiuresis and antinaturesis without substantially changing GFR or RBF, and reflexes of which are abolished by a procedure such as renal denervation include carotid baroreceptor unloading, non-hypotensive hemorrhage, somatic afferent simulation, head-up tilt, chemoreceptor stimulation (e.g. via hypoxia, hypercapnia, etc.), C1 spinal cord block, cardiac tamponade, positive pressure breathing, or the like.

Some non-limiting examples of stress tests that may result in an overall decrease in efferent renal nerve traffic and produce diuresis and naturesis without substantially changing GFR or RBF, and the reflexes of which are abolished by a procedure such as renal denervation include stellate ganglion stimulation, left atrial receptor stimulation, left atrial distension, cooling of cervical vagi, head out of water immersion, intravascular volume expansion, negative-pressure breathing, hypoxic stimulation of peripheral arterial chemoreceptors, or the like.

Some non-limiting examples of stress tests in accordance with the present disclosure include baroreceptor specific tests (e.g. direct stimulation, focused ultrasound stimulation of baroreceptors, tilt table, breath hold, Valsalva, head out of water tests, etc.), thermal reflex tests (e.g. cold and/or warm cold pressor tests, at one or more sites, etc.), blood volume tests (e.g. water, saline addition, diuretic/antidiuretic, blood thickening, etc.), changes in blood analytes (e.g. blood pH, Pco2, Po2, etc.), administration of an anesthetic, direct PNS/SNS stimulation (e.g. via energy delivery, chemical delivery, tactile, visual, audible stimulus, etc.), organ specific direct stimulation (e.g. via energy delivery, focused ultrasound, focused radiofrequency energy delivery, magnetic field stimulation, intra-arterial bolus of a chemical agent, etc.), inducing and watching viscerorenal reflexes (e.g. hepatorenal reflex, renorenal reflex, etc.), administration of a drug in accordance with the present disclosure (e.g. receptor agonists, antagonists, volume changing agents, diuretics, antidiuretics, adrenoceptor agonists/antagonists, guanethidine, etc.), salt load tests, food consumption tests, fasting tests (may decrease sympathetic neural outflow), carbohydrate feeding (may increase sympathetic neural outflow), smoking (e.g. administration of nicotine may increase sympathetic neural outflow, particularly renal neural traffic), combinations thereof, or the like.

Some non-limiting examples of physiologic parameters that may be measured during the stress test may include one or more ocular parameters (e.g. pupillary response, iris feature response, movements, blink rate, tear formation, local tissue blood perfusion, etc.), skin response (e.g. neural outflow to the skin, temperature change, perfusion change, piloerection, sweating, shiver, color change, etc.), cardiopulmonary parameters (e.g. heart-rate, blood pressure, changes in parameters of the ECG, breathing rate, breathing depth, variations thereof, temporal changes in, and transforms thereof, etc.), renal functional parameters (e.g. renal blood flow (e.g. via renal artery Doppler ultrasound), urinary flow and/or bladder filling rate/volume (e.g. via bladder volume ultrasound), changes in sodium excretion, etc.), peripheral vasculature changes (e.g. changes in vasculature stiffness, volume, peripheral resistance, changes in venous capacity, etc.), changes in the gastrointestinal function (e.g. peristaltic function, blood perfusion, etc.), blood analytes, combinations thereof, or the like.

In aspects, one or patch/modules may include a vibrating actuator (e.g. an eccentric motor, an electroactive material actuator, etc.) configured so as to provide a local tactile sensation to the subject. The tactile sensation may be driven by one or more of the physiologic and/or physical signals, by an input from a coach, a caregiver, or the like. In aspects, a system in accordance with the present disclosure may be used to transfer touch sensation from a site without adequate feedback (e.g. a foot, a shin, a knee, a site of neuropathy, an injured region of the body, etc.), to an alternative site on the body, which still has functioning touch feedback. In aspects, a system in accordance with the present disclosure may be used to convey touch sensation between remotely located subjects, to convey haptic touch information from an object (e.g. a portion of a wheelchair, a bumper, etc.) to a site on the body of the subject. Such stimulation may be advantageous to controllably fire one or more types of somatosensory nerves in the tissue region (e.g. such as excitation of Pacinian corpuscles in the tissue, Merkel cell excitation, etc.). In aspects, the stimulatory component may be arranged to provide one or more tactile forms of stimulation to the tissues (e.g. indentation like tactile stimulus, stretch like stimulus, hair follicle deflection, skin shear, vibration, or pain (noxious mechanical stimulation)). Such tactile inputs may be coordinated so as to selectively stimulate one or more neural structures in the skin including Merkel cells, Ruffini cells, Meissner corpuscles, longitudinal lanceolate endings, Pacinian corpuscles, free nerve endings, combinations thereof, or the like.

In aspects, an application linking two or more partners is envisaged, the emotional state of the first partner being conveyed through touch, tactile input, electrical stimulation, etc. to the second partner. In aspects, one or more partners may be fashioned with one or more patch/modules in accordance with the present disclosure and one or more feedback devices in accordance with the present disclosure. In aspects, the exchange of physiologic data from patch/module to feedback device may be used to enhance interactions between the partners, remotely link the partners (perhaps in real-time, pseudo real-time, etc.).

In aspects, one or more of the patches, patch/module pairs, or a HMD in accordance with the present disclosure may include one or more sensors configured to monitor one or more physiologic, environmental, and/or physical parameters locally on the subject. Some non-limiting examples of such sensors include electrophysiologic sensors (e.g. EKG, EMG, EEG, ERG, EOG, respiration, bioimpedance, activity, etc.), temperature sensor (e.g. near to the skin, within a module, ambient (environmental), etc.), thermal gradient sensor (i.e. so as to calculate a heat transfer vector locally on the body of the subject, to estimate a core temperature), barometer, altimeter, accelerometer, gyroscope, humidity sensor, magnetometer, inclinometer, oximeter, colorimetric monitor (e.g. color change analysis of underlying tissue, for respiration, blood flow, pulse, etc.), sweat analyte sensor (e.g. so as to measure sweat constituents, salt content, etc.), galvanic skin response, neural activity (e.g. skin sympathethic activity), interfacial pressure sensors (e.g. for contact assessment, compliance measurement, blood pressure, etc.), flow sensor (e.g. airflow over a module, or the like), surface strain sensor (e.g. via integration of stretch sensors into the patch, evaluation of stretch along one or more electrical interconnect within the patch, integrated capacitive stretch sensors, etc.), a microphone, combinations thereof, and the like.

In aspects, the physiologic measurements may be used to determine an effort related to a given task, to map a particular movement, to a task space, etc. Such information may be useful for use in a training program (e.g. a running program to assist with training a student the biomechanics of the sport, etc.). In aspects, strategically placed patches may be used to capture electromyographic information from muscle groups during movement. In aspects, such information may be coupled to a biofeedback system to assist with the correction of movements made by the subject.

The system may include an algorithm (e.g. either incorporated into a processor on a patch/module pair, the HMD, in a processor coupled thereto, on a server, a virtual server, etc.), configured to analyze one or more images, ocular images, retinal images, facial images, physiologic signals, temperature, heat transfer, hydration level, or the like from the subject.

In aspects, such information may be combined to form a metric relating to dehydration, an elevated body temperature alert, and/or exhaustion state of the subject from which further action may be taken (e.g. generate an alert, an alarm, a report, feedback to the subject, to a coach, to a parent, etc.).

In aspects, an HMD in accordance with the present disclosure may include an embedded hydration sensor, the hydration sensor including a visible, near infrared, and/or infrared emitter such that, upon coupling of the sensor with the tissue of the subject, the emitter is arranged such that radiation emitted therefrom is directed into the tissues of the subject, the sensor including a photodetector (e.g. a narrow band detector, centered generally about 510 nm, 578 nm, 630 nm, 750 nm, 1000 nm, 1180 nm, 1040 nm, 1210 nm, 1300 nm, 1500 nm, a multi-band detector (combinations thereof), a broad band detector, multiple detectors, etc.) to capture reflected or back scattered radiation from the skin from the emitter. In aspects, the corresponding sensor may be configured with a window transparent to, or polarized so as to exclude light, the emitted and/or detected light pass through the window. In aspects, the module may include a corresponding cross polarized window, such that the two windows may be used in unison to exclude light from the surroundings, eliminate incident light from the emitter reaching the detector, etc. Such a configuration may be advantageous to improve signal to noise ratio in such readings, monitor a tissue state of the subject, a tissue hydration state of the subject, a PPG signal, an analyte concentration (e.g. oxygen, water, lipid, melanin, myoglobin, collagen, elastin, etc.), and/or composition of a fluid and/or tissue adjacent the sensor.

In aspects, one or more of the modules, a host, or a system coupled thereto may be programmed with a function to determine the effectiveness of the capture of the intended data by one or more of the patch/module pairs (i.e. the quality of the collected data) and to determine whether such data should be trusted in the collected data stream or not. In aspects, the data may be analyzed to determine if a particular data stream has been corrupted by movement (e.g. due to EMG interference, relative movement at the site of the patch, stretch based artifacts, etc.), by water ingress (e.g. due to moisture entrainment into the module, interface, etc.), poor connection to the subject (e.g. via determination of high electrode impedance, etc.), or the like. Upon detection of an issue, the algorithm may be configured to dismiss data collected from that patch/module pair, de-emphasize such data, etc. until the issue is resolved. The algorithm may be configured to assess whether the data collected from the remaining patches is sufficient to capture the sought after information (e.g. sufficient data to rule out a heart attack, to assess atrial fibrillation, to assess syncope, to determine if a syncope event is cardiogenic, reflex, and/or orthostatic hypertension, etc.), and continuing with monitoring if this is the case, while raising an alarm, alert, etc. if the quality of recording cannot be maintained in light of the issue. Such algorithms may be advantageously implemented to assist with managing a system in accordance with the present disclosure.

In aspects, one or more systems in accordance with the present disclosure may be coupled to a control console (e.g. a computer terminal, a system management software front end, a server, a virtual server, a cloud based service, etc.) whereby aspects of the system(s) may be assessed and altered rapidly to improve workflow therewith, or the like.

In aspects, a system in accordance with the present disclosure may be adapted for use within a home care setting. In such settings, data collected by the host (e.g. a smartphone, a WiFi® hub, a Bluetooth low Energy® hub, etc.) may be sent on to a data center for further analysis. Such information may be collected efficiently without interfering with the subject's daily routine, etc.

In aspects, a system in accordance with the present disclosure may be configured for entertainment purposes. Such a system may include one or more functions to report (e.g. notify, Tweet™, m2m text message, post, communicate, etc.) one or more aspects of a subject's physiologic and/or physical response to a peer group. In aspects, such a system may include connections to a theme park customer management system, a product evaluation feedback system, etc. In one non-limiting example, a system in accordance with the present disclosure may be configured to monitor and report the heart-rate of a subject during an amusement park ride (e.g. during a roller coaster, haunted house, etc.), during an extreme sport (e.g. sky diving, water skiing, hang gliding, etc.), or the like, and to report such metrics to a peer group associated with the subject, optionally along with one or more contextual data points (e.g. roller coaster name, subject location, etc.). Such information may be reported during peak physiologic events (e.g. during peak heart rate, during peak respiratory rate, etc.). Such information may be used to quantitatively track customer response to a product, process, to track subject "activities", or the like.

In aspects, a system in accordance with the present disclosure may be configured to communicate one or more aspects of the collected data, or signals/metrics derived therefrom, goals achieved, or the like to a social forum associated with the subject (e.g. a social network, Facebook™, Instagram™, Google+™ Patient's Like Mc™, or the like). Such information may be included in a feedback loop (e.g. so as to encourage a patient, congratulate a subject on an outcome, etc.). In aspects, one or more processors integrated with the social forum may be configured to automatically analyze the collected data and produce one or more metrics relating to disease progression, health state, performance, events (e.g. excitement, amusement park reporting, product usage feedback, intimacy assessment, stroke, physiotherapy progress, etc.).

In aspects, an HMD in accordance with the present disclosure may include an optical sensor arranged thereupon so as to interface with a facial tissue of a subject when coupled thereto, the optical sensor may be arranged so as to capture blood flow readings off of the septum, the bridge of the nose, tissue near the nose (philtrum, at the anterior nares), or along an intranasal wall (vestibule, alar of the nose, alar lobule, etc.), near an eye of the subject, etc. The optical sensor may be coupled with a microcircuit in accordance with the present disclosure into a septum clip, an alar clip (e.g. for placement along the outside or inside of the nose, etc.) configured to fix the HMD to the face of the subject, etc. In aspects, an optical sensor may be tailored to monitor a blood flow parameter. In aspects, the optical sensor may be used to monitor a real-time blood perfusion parameter in a tissue of the subject, in the immediate vicinity of the optical sensor. The blood pressure measurement device may include a plurality of such sensors, each sensor configured to monitor a local blood perfusion parameter in the tissue of the subject. Such information may be collected from each sensor in real-time. Correlation of delays, waveform changes, and the like over the body of the subject may be used to generate a correlated signal. In aspects, the correlated signal may be used to create a diagnostic signal (e.g. blood flow volume, blood ejection rate, peripheral vascular parameter, blood oxygen saturation, blood oxygen partial pressure, blood carbon dioxide partial pressure, blood pressure, etc.).

In aspects, the optical sensor may be configured to measure sPO2, or a signal related thereto near to a line of contact between the nose and the cheek or alternatively at the root of the nose (near the bridge of the nose).

In aspects, an HMD may include a power source, a housing, one or more interconnects, signal conditioning circuitry, communication circuitry, a processor, a transceiver, a transducer, one or more sensors, an antenna, a buzzer, a button, a light source, and/or the like, configured to generate one or more signals (e.g. physiologic, electrophysiologic, and/or physical signals) or a feedback signal in accordance with the present disclosure. The signal conditioning circuitry may be configured to amplify, de-noise, pre-filter, generate a trigger, analyze aspects, extract a metric, etc. from one or more physiologic and/or physical signals during a monitoring session, a calibration session, an attachment event, etc.

In aspects, a microcircuit in accordance with the present disclosure may include one or more of signal conditioning circuitry, a system on chip, a processor, a radio, a power management system, an energy harvesting system, a memory module, etc.

In aspects, the processor may be programmed to operate in a range of power states (e.g. a low power state, a diagnostic state, a monitoring state, a subject detected state, a synchronization state, a calibration state, a communicating state, a recharging state, an alert state, a troubleshooting state, etc.). The processor may operably remain in a low power state so as to improve the lifetime of the power source. The processor may switch between states based on conditions determined via the sensors, a recharge unit, a calibration unit, a host device, etc.

The HMD and/or an associated patch, patch/module pair, etc. may be configured to communicate with one or more patches, additional modules, an analysis device, and/or a host device, etc. Such communication may be performed wirelessly (e.g. acoustically, via infrared, via radio frequency communication, etc.) through the environment surrounding the subject, through the body of the subject (e.g. acoustically, optically, capacitively, resistively, and/or inductively coupled signal transmission, etc.). In aspects, one or more patches may relay a combination of an energy signal (e.g. to determine a physiologic parameter) as well as to communicate an information signal to one or more patches, modules, a host device, etc.

The processor may be programmed and configured via connection with one or more sensors to determine when an HMD, module and/or patch/module pair has been placed onto a subject. After attachment, one or more physiologic signals and/or biometrics may be monitored on the subject so as to determine the identity of the subject, one or more calibration parameters being set based upon the identity of the subject.

The processor via data collected from one or more sensors may be configured to determine the quality of the interface with the subject. In aspects, the HMD may include two or more electrode elements to be placed into electrical contact with the subject during a monitoring session. The processor may, via the electrode elements and/or signal conditioning or test electronics attached thereto, estimate the impedance between the electrodes and the body of the subject. If the impedance levels are within acceptable ranges, the processor may initiate collection of bioelectrical information from the subject during a monitoring session (e.g. ERG, EOG, facial EMG, EEG, etc.). If impedance levels are deemed outside acceptable ranges, the processor may opt not to monitor the subject during the monitoring session. In this case, the HMD may communicate a "bad connection" signal to one or more associated modules, patches, an analysis device, and/or a host device during a monitoring session. The HMD may alternatively or in combination send a compromised signal, and one or more modules, patches, an analysis device and/or a host device may be used to determine as much information as possible from the signal (e.g. in relation to an EKG example, the signal measured may not be of diagnostic quality, yet detection of the QRS pulse may be adequate for timing blood flow events between patches, determining heart-rate, etc.). As such, analysis of degraded signals may be advantageous for completing a monitoring session with at least a minimum quantity of viable signal information.

One or more of a microcircuit, an associated processor, and/or software algorithms for detecting one or more fault conditions related to contact with the body of the subject. In aspects, the microcircuit may be configured to detect when the impedance between an electrode and the subject is within an acceptable range for measurements (e.g. less than 2Mohm, less than 200 kohm, less than 20 kohm, less than 2 kohm, or the like). In aspects, the electronics may be configured to glean such information by measuring or estimating the impedance between two or more electrode pickups on a coupled patch. In aspects, an impedance estimate may be determined by applying a brief voltage or current pulse to a first electrode, applying a load to a second electrode, and monitoring the temporal response of the second electrode against the first. The rise time of the temporal response compared against the load may be used to indicate the collective impedance of the electrodes and tissues there between.

In aspects, one or more system components, the HMD, one or more patches, patch/module pairs, or a stimulatory device may be configured to interface with the subject with a stimulation component. The stimulation component may include a signal source for imparting an energy signal (e.g. electrostatic, electromagnetic, magnetic, vibrational, thermal, optical, sonic, ultrasonic, etc.) into the body of the subject. The energy signal may be used to communicate to the user, as a form of alert, for diagnostic purposes, to determine a physiologic and/or physical parameter, to excite a nerve within a volume of tissue within the body, to generate a coordination signal to configure an array of patches, provide sensation to the subject, etc.

In aspects, the HMD may include an optical sensor for measuring colorimetric changes in the adjacent tissues during the monitoring process. Such information may be used, optionally in combination with an energy signal to determine one or more optically variable physical parameters and/or one or more optically variable physiologic parameters of the subject, local to the associated tissues. In aspects, the optical sensor may be used in combination with one or more optical emitters (e.g. light emitting diodes, laser diodes, bulbs, etc.) to monitor a physiologic signal related to local blood perfusion on the body of the subject. A plurality of such sensors may simultaneously monitor such physiologic signals at discrete locations on the face, head, ear, and/or neck of the subject and relay such information to one or more patches, modules, a host device, a signal processing microcircuit, a processor, and/or an analysis device. The combination of information from such sensors may be used to determine blood flow dynamics throughout one or more regions of the face, head, ear, and/or neck, of the subject, to characterize the underlying vasculature in one or more such regions of subject, etc. In aspects, blood perfusion related signals may be simultaneously measured at multiple locations on the body of the subject (e.g. the chest, arm(s), leg(s), face, neck, eyes, ears, etc.) and the phase and/or time delays between such signals, as well as the shapes and characteristics of the signals may be used to determine an arterial brachial index of the subject. Such techniques may also be used to determine one or more regions of the subject that may suffer from arterial or venous insufficiency, to determine the blood pressure of the subject, to determine changes in vascular load of an extremity, and/or to determine vessel elasticity changes in the body of the subject during use. In aspects, such techniques may be used to estimate the location and/or presence of a blood clot in an extremity of the subject.

In aspects, the HMD, one or more modules, or the like may include a barometer and/or an altimeter to measure a local environmental parameter (e.g. local pressure, temperature, etc.) during a monitoring session. In aspects, such information may be used to determine the posture of the subject, determine if the subject has fallen, etc. In aspects, the posture of the subject may be used to determine and/or improve such physiologic measurements as those relating to blood pressure of the subject, correcting EKG data, determining positional relationships between a plurality of patches positioned on the body of the subject, etc.

In aspects, the HMD, one or more modules, or the like may include an activity sensor (e.g. an accelerometer, a gyroscope, a pedometer, etc.) to measure one or more inertial parameter (e.g. local acceleration, rotation, vibration, etc.) at a location on the body of the subject during a monitoring session. In aspects, information obtained from one or more activity sensors may be used to remove movement artifacts from a physiologic signal, calculate a trajectory, determine a gravitational reference frame, orientation of the module and/or accompanying patch, etc. In aspects, one or more modules may include a tri-axis accelerometer for characterizing the local inertial vector of the body of the subject to which the module is attached. In aspects, one or more modules may include a tri-axis accelerometer, a gyroscope, and optionally a magnetometer. Information from one or more such sensors may be used to calculate an improved local trajectory of the body part of the subject during a monitoring session.

According to aspects there is provided, a method for monitoring one or more physiologic and/or physical signals from the body of a subject in accordance with the present disclosure including applying one or more patches, and/or an HMD each in accordance with the present disclosure to the body of the subject, and attaching a corresponding number of modules (e.g. in the cases of patches) each in accordance with the present disclosure to the patches (i.e. so as to form one or more patch/module pairs in accordance with the present disclosure), establishing a body area network among the modules, and collecting physiologic and/or physical signals from the subject using the HMD, patches, and modules during a monitoring session (i.e. for a period of time suitable for the desired purpose of the method, e.g. 10 seconds, 1 min, 1 hr, 8 hrs, 24 hrs, 1 week, 1 month, 3 months, chronically, etc.).

In aspects, the method may include storing the collected signals on a memory device (e.g. a memory location on the patches, the modules, a host device, a user device, a datacenter, etc.). In aspects, the body area network may be extended to include a host device in accordance with the present disclosure. The method may include transferring the signals and/or one or more signals and/or metrics derived therefrom from the patches and/or modules to the host device, in real-time, intermittently, in a time synchronous fashion, or the like, during and/or after the monitoring session. In a range of applications, the system may be configured to monitor for an event (e.g. a change in heart function, a change in EMG, a change in posture, an impact, a change in breathing rate, etc.).

In aspects, there may be applications where real-time or even pseudo real-time data collection is not necessary (i.e. during aspects of a home sleep study, health report generation, diagnostic assessments, etc.). In such scenarios, an HMD, and/or module in accordance with the present disclosure may be configured to store the collected data locally on a memory device. The module may be configured to download the data to a recharging bay in accordance with the present disclosure at the conclusion of the monitoring session, periodically throughout the monitoring session, or the like in order to transfer the data to a processor for analysis, review, etc.

In aspects, a method for interacting with a subject with an HMD, and/or one or more patch/module pairs in accordance with the present disclosure may include measuring one or more physiologic signals therefrom. The method may include deriving a feedback signal, a command, an alert, a metric, a diagnostic value, a schedule, an augmented reality overlay, an emotional state, a physiologic response to a stress test, etc. from one or more of the signals. The method may include identifying when one of the modules, and/or HMD requires attention (e.g. the battery is low, a poor interconnection has been made with a corresponding patch, or between a corresponding patch and the subject, a malfunction has occurred, a poor signal quality is being obtained therefrom, etc.). Attention may include swapping the module with a new module, swapping the module out without interrupting the monitoring procedure, removing the module and corresponding patch from the subject, etc.

In aspects, the method may include providing feedback to a user (e.g. the subject, a physician, a therapist, an officer, a soldier, a group leader, a teacher, a student, an EMT, a coach, a trainer, a partner, etc.) relating to the physiologic and/or physical signals. The method may include representing a signal, value, metric, graphic, etc. related to the signals on a feedback component in accordance with the present disclosure (e.g. on a display, a HUD, a wristwatch, an earpiece, a loudspeaker, a tactile display, etc.).

In aspects, the method may include coordinating the monitoring session across multiple subjects, and optionally synchronizing data collection across the subjects for purposes of calibration, comparative analysis, etc.

In aspects, a modular physiologic monitoring system in accordance with the present disclosure may include a plurality of patches (e.g. patches, patch/module pairs, etc.), and an HMD. In a method of monitoring a subject with such a system, the positioning of the patch/module pairs onto a subject may be visually assessed during placement. One or more patches, modules, or both may include an orientation marker and/or an identifying marker that may be visually assessed from a local observer after placement on the body of the subject. In aspects, the precise placement of the patch/module pairs on the subject may be calculated post attachment by taking an image of the subject after the patches have been placed on the subject. The image may be taken with a coordination device (e.g. a smartphone, a camera, a Kinect™ camera, a HUD ready pair of glasses, Google Glass™, etc.), a host device, etc. In aspects, the orientation markers may be segmented, identified, and extracted from the images to calculate one or more calibration parameters from the orientation of the patches over the body of the subject. In aspects, one or more features associated with the subject (e.g. neck, shoulders, arms, legs, torso, etc.) may be detected and categorized, so as to be incorporated into a patch placement calculation or assessment algorithm.

In aspects, the coordination device may be used by a user (e.g. the subject, a practitioner, a clinician, a trainer, a coach, a friend, etc.) to take an image of the subject or a portion thereof after placement of the patches. Patch locations and orientations on the subject (e.g. position vectors, positions with respect to anatomical features on the subject, etc.) may be calculated from the image and used to produce a corrected or standard EKG output, calibrate an EMG based physiotherapy assessment system, automatically assign muscular group behavior to corresponding patches, etc. The system, the host device, the coordination device, etc. may alert a user as to the adverse placement of a patch, the need for more patches, etc. in order to determine a particular cardiovascular function. In aspects, the user may be directed to place one or more additional patches and/or adjust the position of an already placed patch in order to favorably adjust the physiologic data obtained therefrom.

In aspects, the coordination device may also be used to direct the user to properly place one or more patches on the subject dependent upon the goal of the particular monitoring session. In aspects, an augmented reality display may be employed to direct a clinician to properly place electrodes on the body given the goal of the particular monitoring session (e.g. to assist with placement for EKG, EMG, to match placements from previous sessions, etc.). The augmented reality display may overlay orientation markings onto a camera generated display, highlighting where on the subject the user should place one or more patches in order to better achieve the goals of the indicated monitoring session.

In aspects, a module in accordance with the present disclosure may include one or more algorithms (e.g. implemented on a processor, SoC, etc.) configured to analyze the signals obtained from the subject. In aspects, an algorithm in accordance with the present disclosure may be configured to extract a metric from the signal including a heart-beat, time-stamping of a QRS complex, etc. (or other metrics as described herein). In aspects, to save on wireless bandwidth and associated power consumption, an HMD, and/or a module may include an algorithm to efficiently extract such metrics from the raw data and send the metrics rather than the raw data. In aspects, the HMD, and/or modules may include multiple modes of operation (e.g. a low priority mode, a high priority mode). Some modes may be configured so as to send small amounts of data (i.e. such as when a heart-rate or monitored function of a subject is within a 'normal' range), or metrics extracted from the raw data (e.g. a simple heart-rate, etc.) so as to maintain a low wireless bandwidth. Some modes may be configured so as to send all available data (i.e. such as when an 'event' is occurring, when a previously 'normal' signal changes) so as to provide a user with as much information as possible during the 'event'. Such a configuration may be advantageous to balance power consumption of hardware within the modules with the depth of the monitored signal.

In aspects, a method in accordance with the present disclosure may include determining a priority metric for one or more signals captured by a module in the system (e.g. via assigning a priority level, determining a degree of redundancy, etc.). Such a priority metric may be used in an algorithm to determine the type and urgency of an "alert" generated by a failure on one or more modules in the system. In one non-limiting example, a system including 5 modules is deployed onto a subject to monitor a 3 lead equivalent EKG in accordance with the present disclosure. A priority metric for the system is determined based on the number of modules that would have to fail in order to risk obtaining a low quality EKG from the subject. In aspects, the priority may be more or less affected by the removal of one or more modules in the system (i.e. based upon the location of the module on the subject), etc. If a module on the subject fails or indicates that it is about to fail (i.e. a battery low alert). The system may be configured to assess how such a failure will affect the priority metric, thus adjusting a potential alert accordingly (i.e. from "do nothing" through to "needs immediate attention"). Such a configuration may be advantageous for reducing false alarms within a hospital setting, thus reducing alarm fatigue, or the like while providing more robust monitoring of EKG.

A system in accordance with the present disclosure may be provided as part of a monitoring kit. In aspects, a monitoring kit in accordance with the present disclosure may include an HMD, one or more modules, a recharging bay, one or more patches, or set of patches (i.e. a series of patches configured and dimensioned to perform a particular type of monitoring on a subject), and (optionally) one or more accessories such as an adhesive removal wipe/spray, skin preparation tools, instructions, software access, etc.

In aspects, the recharging bay may be configured to hold one or more modules each in accordance with the present disclosure. The recharging bay may be configured so as to act as a host device (e.g. as a wireless hub, etc.) so as to provide multiple functions for a user. Additionally, alternatively, or in combination the HMD may be configured to act as a host device for the system.

In aspects, the host device may be operably worn/held by the subject, provided by the HMD, located near to the subject, integrated into a bedside alarm clock, or housed in an accessory (e.g. a purse, a backpack, a wallet, etc.). In aspects, the host device may be a mobile computing device (e.g. a smartphone, a tablet computer, a pager, etc.). In aspects, the host device may be a local router, a data recorder, a network hub, a server, a secondary mobile computing device, a router, a repeater, etc.

In aspects, the host device may be a dongle or accessory for a mobile computing device. In such aspects, the host device may be configured to coordinate communication with one or more patches/modules, analyze incoming patch data, fuse sensor information from one or more patches, condition and/or de-noise information signals obtained from one or more patches, correlate connectivity of one or more patches, to reconstruct signals from parameters sent by one or more patches/modules, or the like. In aspects, the host device may be configured to generate one or more physiologic signals, alerts, etc. therefrom.

In aspects, one or more patches, modules, a host device, user device, and/or an analysis device may fuse sensory information from the HMD, and/or one or more patches during a monitoring session. If sensory information is missing from a particular patch, module, etc. or if it is in some way compromised, etc. the one or more patches, modules, the host device and/or the analysis device may ignore, remove, de-emphasize, etc. the information. As such, the system may be advantageous for providing a robust, fault tolerant means for monitoring one or more physiologic parameters of a subject.

In aspects, the HMD, one or more patches, modules, a host device, a user device, and/or an analysis device may generate various levels of alerts for maintaining the monitoring session during a long-term monitoring session on a subject. Such alerts may be related to a subject emergency (e.g. a fall, a heart arrhythmia, a neurological arrhythmia (e.g. due to a seizure), an elevated heart-rate, syncope, an accident, an impact, a sleep apnea event, respiratory arrhythmia, choking, a drop in arterial $CO_2$, hypercapnia, a missing heart-rate, etc.), a moderate priority maintenance need (e.g. a high number of compromised signals, a high number of low or depleted power sources, etc.), a low priority maintenance need (e.g. a limited number of compromised signals, one or more low battery indications, etc.).

In aspects, the HMD, one or more patches, modules, a host device and/or an analysis device may generate an "information quality" signal related to the overall quality of one or more signals (e.g. individual information signals, a collective signal, a physiologic parameter, etc.) related to one or more patches on the subject, and/or the overall system. Such an "information quality" signal may be used to determine and/or convey the degree of confidence that the system has in the physiologic parameters of a subject being measured during a monitoring session. The signal may be good, average, compromised, poor, unacceptable and/or the like. An alert may be advantageously constructed from the information quality signal so as to optimally compromise between functionality (e.g. basic quality of the monitoring session) and productivity (e.g. number of alerts requiring attention) during a monitoring session.

In aspects, a system, device, method, and/or component in accordance with the present disclosure may be used for assessing the neural tone of a subject (e.g. neural tone associated with a region of skin of a subject, tone associated with an organ of a subject, tone associated with neuroendocrine function in a body, signals, traffic, etc. associated with central and/or peripheral neural traffic between a brain, ganglion, neural structure, and an organ, etc.). The discussion now turns to discussion of non-invasive systems and methods for determining a state of one or more aspects of an autonomic neural system (ANS) of a subject, determining a relationship between the state of one or more aspects of an ANS and a stress test, determining the outcome of a neural traffic modifying procedure, determining if a subject is a suitable candidate for a procedure, medical treatment, combinations thereof, and the like.

Signals traveling through the autonomic nervous system of a subject include bidirectional signals: afferent, efferent traffic. Efferent traffic can trigger changes in different parts of the body simultaneously. Relating to some non-limiting examples, the sympathetic nervous system can accelerate heart rate, widen bronchial passages, decrease motility (movement) of the large intestine, constrict blood vessels, increase peristalsis in the esophagus, cause pupillary dilation, iris muscle movement, iris sphincter movement, iris dilator movement, piloerection (goose bumps) and perspiration (sweating), raise blood pressure, etc. The parasympathetic system can affect various systems and bodily functions as well, generally in an approach opposing the action of the sympathetic system. The differential traffic between the SNS and PNS innervating a particular organ may be as important to the overall function of that organ, as the individual afferent/efferent traffic of each neural network.

Relating to aspects, one or more synapses in the skin (preganglionic neuron to postganglionic neuron) may be mediated by nicotinic receptors activated by acetylcholine (a neurotransmitter), one or more synapses of the postganglionic neuron may be mediated by adrenergic receptors and may be activated by either noradrenaline (norepinephrine) or adrenaline (epinephrine). Sweat glands receive sympathetic innervation but include muscarinic acetylcholine receptors, which are normally characteristic of the parasympathetic nervous system. Other exceptions exist, such as with certain deep muscle blood vessels, which dilate (rather than constrict) with an increase in sympathetic tone. This is because of the presence of more beta2 receptors, rather than alpha 1, which are more frequently found on other vessels of the body. Traffic associated with such nerves may be monitored, blocked, stimulated, and or assessed with a system, device, patch, patch/module pair, and/or method each in accordance with the present disclosure.

Such systems may be advantageous for assessing a disease state of a subject, an autonomic neural disorder, a peripheral neuropathy, the extent of a neural block (e.g. such as via a local analgesic, application of a neuro-blocker, a neurotoxin, etc.), the state of a neural block, a neuroendocrine relationship, a state of a sympathetic neural branch, a state of parasympathetic neural branch, etc.

In aspects, a patch and/or module in accordance with the present disclosure may include a plurality of electrodes, microelectrodes, or the like for assessing a skin neural activity, skin sympathetic neural activity, skin somatosensory neural activity, skin parasympathetic neural activity, combinations thereof, or the like. Additionally, alternatively, or in combination a patch and/or module may include a sensor for assessing local hydration, galvanic skin response, or the like in accordance with the present disclosure, an optical sensor for assessing a blood perfusion and/or oxygenation, etc., combinations thereof, or the like. Such combinations may be advantageous to assess differing aspects of a local neural response to a stimulus, a stressor, a procedure, etc.

In aspects, a patch and/or module may be configured to assess skin neural tone (autonomic, somatosensory, sympathetic, parasympathetic, follicular erection, smooth muscle neural activity, vascular contraction/dilation, etc.), in combination with blood perfusion, and/or local hydration (e.g. due to sweating, exudate migration, etc.), or the like. In aspects, a system in accordance with the present disclosure may include one or more patch module pairs configured to monitor skin neural tone at one or more sites on a body, in combination with one or more patch module pairs configured to monitor EKG, heart rate, heart rate variability, breathing rate, breathing effort, muscle tone, tissue hydration, sweating, blood perfusion to tissues, combinations thereof, or the like.

Additionally, alternatively, or in combination a neural tone may be extracted from an EKG, an EMG, an ERG recording, or the like (such as separated from the noise floor thereof), so as to further assess an autonomic neural state from a subject.

Such systems may be used to determine the autonomic neural state of a subject (i.e. a state of the autonomic nervous system (ANS)), to determine the sympathetic and/or parasympathetic component of the autonomic state of a subject, to determine the state of a branch of the ANS, to determine the relationship between the ANS state, a branch thereof, and/or a change in state thereof and a change in organ function, to determine a contribution of afferent traffic from an organ in a subject to the autonomic neural state of the subject or to changes thereof, to determine a relationship (e.g. a qualitative relationship, a causal relationship, a quantitative relationship, a transfer function, etc.) between an ANS state of a subject and an input parameter, a stress test, a medical procedure, delivery of a medication, a change in state of an organ in the body, the outcome of an interventional procedure, a neural ablation, a combination thereof, or the like.

In aspects, such systems may be configured to assess changes in an overall autonomic neural state of a subject as influenced by a subsystem of the body, a change in neural traffic along a nerve, nerve plexus, ganglion, receptors, efferent/afferent traffic, and/or sensory traffic from one or more sites in a subject (i.e. so as to establish a cause—effect relationship between the target and the overall ANS state). Alternatively, additionally, or in combination, such systems may be configured to actively influence the autonomic neural state of a subject while monitoring changes in one or more organ states, organ functions, or the like (i.e. so as to establish an ANS—organ functional influence). In aspects, a patch module pair in accordance with the present disclosure may be configured to apply a stress state to a first tissue site, one or more additional patch module pairs configured to monitor one or more forms of neural traffic, and/or surrogates thereof at one or more additional sites on the body of the subject.

Alternatively, additionally, or in combination a system in accordance with the present disclosure may include and/or may be configured to work in conjunction with a therapeutic system in accordance with the present disclosure. Such a therapeutic system may include an ablation system, a neuromodulation device/implant, an ablation catheter, a focused energy delivery device, a radio frequency ablation system or catheter, a microwave ablation system or catheter, an ultrasound energy delivery system (e.g. a high intensity focused ultrasound (HIFU) system, catheter, or the like) or catheter, a cryoablation system or catheter, a chemical ablation system or catheter, a radiosurgical system, an optical ablation system (e.g. an infrared ablation system, a laser ablation system, etc.), a MR guided HIFU system, a combination thereof or the like. In aspects, the system may be configured to temporarily and/or substantially permanently alter the neurological state of one or more nerves in a subject through a procedure (e.g. delivery of energy, delivery of a chemical, stimulation, etc.), the system configured to monitor one or more aspects of a neural state in the subject to determine the completion of such a procedure. Such monitoring may be performed so as to measure activity of a related branch of the ANS, a surrogate physiologic parameter associated therewith, tone associated with at least a portion of the sympathetic or parasympathetic nervous system, a relationship between a cursory stress test and the ANS (e.g. a change in the results of a stress test applied to a subject pre and post procedure), or the like.

In aspects, a system in accordance with the present disclosure may be used to determine if a subject is a suitable candidate for a procedure, such as a neuromodulation procedure, a neural ablation procedure, a sympathectomy, a peripheral neural block, or the like. Such an assessment may be determined by comparing the functional relationship between the ANS or an aspect thereof, with one or more stress states, over a range of stress stimulating inputs, as assessed during a stress test, combinations thereof, or the like. Subject inclusion/exclusion criteria may be developed around one or more metrics generated from one or more stress tests completed on the subject in accordance with the present disclosure, a baseline autonomic, sympathetic, and/or parasympathetic tone of a subject as measured with a system, device, or method in accordance with the present disclosure, etc.

Some non-limiting examples of uses for such a system include, assessment of autonomic function of a subject, CNS disorders, assessing impact of a medication on the ANS of a subject, assessing medication dosage parameters (e.g. personalizing medication for a subject, personalizing dosage for a subject, timing dosage delivery for a subject, assessing periods of activity for a medication on a subject, assessing pharmacokinetics of a substance on a subject, assessing differences between bioavailability of substances, assessing effectiveness of a generic medication on a subject, assessing a difference in delivery rate between medications, etc.), hypohidrosis, hyperhidrosis, neuroendocrine function, suitability for a denervation procedure, suitability for a renal or carotid body denervation procedure, diabetic neuropathy assessment, peripheral neuropathy, analgesic feedback, neural block feedback, in-procedure feedback, procedural follow up, cardiac conditions, lie detection, assessment of sexual dysfunction, psychiatric assessment, urinary/fecal incontinence, combinations thereof, and the like.

In aspects, a system in accordance with the present disclosure may include one or more components, sensors, and/or subsystems for assessing a change in a state of the autonomic neural system (ANS) and/or a relationship between a component of the ANS and a stress test at a site that is non-invasively accessible (inter aural, intra nasally, salivary, skin sites (groin, armpit, neck, anal-rectal region, palm of hand, sole of foot), eye, corneal surface, pupil, iris, iris EMG, iris feature movement, iris sphincter muscle movement, iris dilator muscle movement, EOG, ERG, etc.). In aspects, one or more neural activity sensing elements may be configured and arranged near the trachea of a subject so as to assess the larynx tone during application of a stress test there upon. Such an assessment may be a suitable surrogate for PNS activity along the nearby vagus nerve plexus. In aspects, such activity may be monitored with one or more multi-sensor patches in accordance with the present disclosure.

In aspects, the system may include one or more devices to monitor one or more of ocular neural tone, facial muscular tone, electroretinography, nasalis muscular tone, temporalis tone, zygonaticus tone, orbicularis tone, occipitofrontalis tone, etc. Such tone may be assessed and change as the relationship between the overall SNS and PNS of a subject change, during the stress state, during a procedure, after completion of a procedure, etc.

In aspects, the system may include one or more devices configured to monitor one or more physiologic signals including but not limited to heart rate, heart rate variability, heart murmur, electrophysiologic signals associated with low level autonomic activity (e.g. as extractable from an EKG signal, etc.), perfusion, sweating, hydration, or the like. The physiologic signals may be compared, analyzed, etc. before, during, and/or after one or more stress tests, procedures, etc. to determine the extent thereof, the body response thereto, etc.

In aspects, a device in accordance with the present disclosure may be configured to monitor one or more aspects of neural traffic, and/or surrogates thereof within one or more regions of the skin of a subject. Such neural traffic may include somatosensory traffic, receptor response, sympathetic outflow, parasympathetic outflow, muscular response (i.e. to SNS, PNS, etc.), smooth muscle electrophysiological response, etc. In aspects, such neural traffic may be monitored by a plurality of microelectrodes, one or more of the microelectrodes electrically isolated from the others such that the local electrophysiological signals can be teased out from the overall macro electrophysiological traffic in the vicinity of the region.

According to aspects there is provided a method for assessing the sympathetic neural state of a subject including, interfacing a system in accordance with the present disclosure with a subject, and monitoring one or more of neural traffic, a physiologic parameter, or a surrogate of neural traffic at one or more sites on the body of the subject.

The method may include monitoring neural traffic at two or more locations (e.g. such as a PNS innervated site, a primarily SNS innervated site, a sweat gland heavy site, a somatosensory dense site, etc.). Such monitoring at morphologically different skin regions on a body may be advantageous to extract different sub system responses from the overall traffic.

The method may include, assessing one or more changes in traffic associated with a neural state, parasympathetic neural state, sympathetic neural state, or the like, and determining the response of the sympathetic system of the subject to the stress test.

The method may include, performing a procedure in accordance with the present disclosure on the subject and monitoring the response, monitoring completion thereof, monitoring follow up thereof, etc. in accordance with the present disclosure.

According to aspects there is provided, a method for quantifying the contribution of a neurological state to a disease state of a subject including, non-invasively monitoring the neural state or a surrogate of the neural state of the subject to generate data, performing a stress test on the subject while monitoring, and analyzing the data to determine the change in neurological state of the subject, and/or to determine the relationship between the stress test and the neurological state of the subject, the analysis relating to the contribution.

According to aspects there is provided, a system for assessing the autonomic neural state of a subject and/or the relationship between sympathetic and parasympathetic autonomic neural state of a subject including a sensor (such as but not limited to an EMG, micro electrode array on a contact, ERG, etc.) for monitoring a physiologic state of an ocular element of a subject (e.g. state of a pupil, iris, iris feature, tear gland activity, ocular muscle, retinal state, retinal traffic, the tone of an ocular muscle, etc.), and a light source and/or display for providing one or more visual cues, optical stresses, incident light profiles, light scans, optical stress tests, etc. into the eye or eyes of the subject.

In aspects, an HMD in accordance with the present disclosure may include an array of microelectrodes, signal conditioning circuitry coupled with the microelectrodes, and a processor programmed with machine readable instructions coupled to the signal conditioning circuitry, the signal conditioning circuitry and/or the processor configured to extract one or more neural signals from one or more of the microelectrodes.

In aspects, one or more of the microelectrodes may include a microneedle, the microneedle configured so as to penetrate a structure nearby the patch upon engagement therewith. In aspects, the microneedle may be sized with a predetermined length, the length thereof arranged so as to position an electrode arranged thereupon near to a characteristic depth of a nerve structure of interest within a region of skin on a body (e.g. a hairy skin surface, a glabrous skin surface, a mucosal surface, near a sweat gland, near a bulb of a hair follicle, near an arrector pili follicular muscle, near a sebaceous gland, near an erogenous zone, etc.).

In aspects, the processor and/or signal conditioning circuitry may be configured to extract the neural signal amid one or more electromyographic signals associated with a nearby striated or smooth muscle structure, stretch based surface potential changes, movement, combinations thereof, or the like. In aspects, EMG artifacts may be algorithmically removed from microelectrode signals, stretch based surface potential changes may be removed by subtracting a stretch surrogate signal (e.g. as obtained from a stretch sensor, a perfusion sensor, etc. in accordance with the present disclosure), movement may be removed by subtracting a movement signal (e.g. as measured by kinematic or kinetic sensor in accordance with the present disclosure), or the like.

In aspects, the signal conditioning circuitry and/or processor may be configured to assess the bioimpedance between two or more microelectrodes upon engagement with the skin so as to determine a hydration state thereof, to determine a fluid content thereof, or the like.

In aspects, the patch may include a plurality of macroelectrodes (2, 3, 4, greater than 4, etc.), each macroelectrode configured to interface with the skin upon placement thereupon, the signal conditioning circuitry and/or processor configured to assess the bioimpedance between the macroelectrodes (e.g. in a two point measurement configuration, 3 point, 4 point measurement configuration, etc.), upon engagement with the skin so as to determine a hydration state thereof, to determine a fluid content thereof, or the like.

In aspects, the HMD may include one or more temperature sensors, arranged so as to bias against a tissue site on the subject when coupled thereto, the temperature sensor(s) configured to assess a thermal state of an adjacent tissue upon engagement therewith.

In aspects, the system may include a device with a diagnostic and/or therapeutic sonography component, configured to provide an ultrasonic signal to and/or receive a sonographic signal from an adjacent tissue upon engagement with the skin. The sonography component may be configured so as to image, and/or capture a metric from an adjacent tissue upon engagement with the skin. In aspects, the metric may include a perfusion parameter, a tissue stiffness parameter, a hydration level, a temperature rise, a vessel diameter, a combination thereof, or the like. In aspects, the sonography component may be configured to stimulate and/or ablate a tissue site within the subject.

In aspects, the system may be arranged to measure one or more of, but not limited to, respiration (breathing rate, breathing volume, lung stress or load, or the like), blood pressure, blood oxygen level, heart rate variability, heat flux, galvanic skin response, core body temperature, skin temperature, sympathetic or parasympathetic response, combinations thereof, or the like in order to assess the function of the ANS or changes therein during an assessment, before, during, and/or after a stress test, before, during, and/or after a procedure, etc.

In aspects, the system may be configured to capture a plurality of signals, signals from multiple sites on the body, signals from multiple skin types, etc. in order to establish relationships between aspects of a neural system and the stress test, between aspects of the neural system of the subject in general, etc.

Discussion related specifically to the Figures follows, the discussion above may be applied where ever applicable to a particular Figure reference.

Figure 1B:
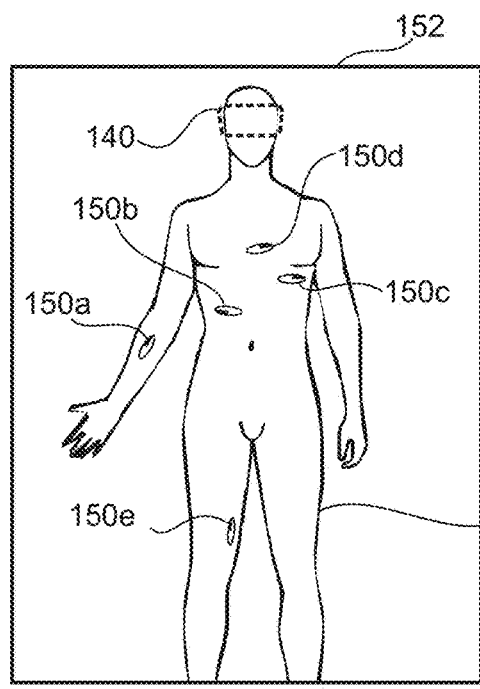
Figure 1C:
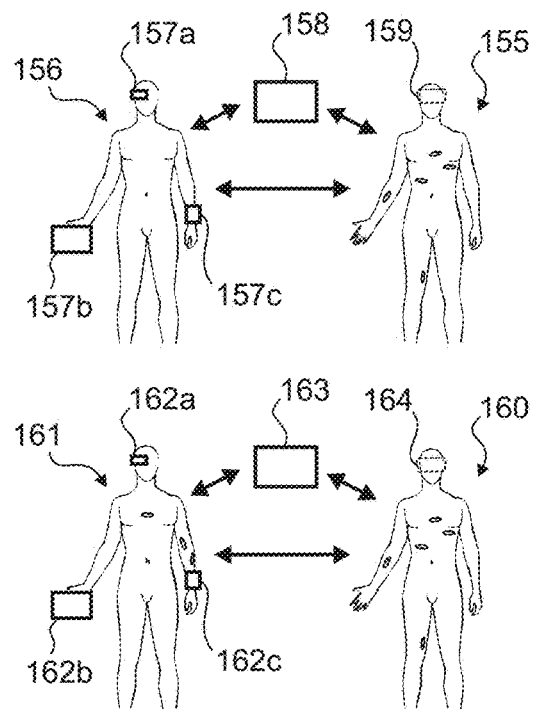

FIGS. 1a-1c show aspects of modular physiologic monitoring systems in accordance with the present disclosure. FIG. 1a shows a subject 1 with a series of patches and/or patch/module pairs 5-137 each in accordance with the present disclosure, a host device 145 in accordance with the present disclosure, a feedback/user device 147 in accordance with the present disclosure displaying some data 148 based upon signals obtained from the subject 1, and one or more feedback devices 135, 140 in accordance with the present disclosure configured to convey to the subject one or more aspects of the signals or information gleaned therefrom. The host device 145, the user device 147 the patches and/or patch module pairs 5-137, and/or the feedback devices 135, 140 may be configured for wireless communication 146, 149 during a monitoring session.

The system may include a head mounted display (HMD) 140 in accordance with the present disclosure. The HMD 140 may include one or more physiologic sensors, ocular assessment cameras, so as to interface with the subject in accordance with the present disclosure. The HMD 140 may include one or more LEDs arranged there about for establishing a light field within the visual field of the subject 1. The LEDs may be configured so as to generate light fields with varying intensity, spectral content, spatial intensity/color gradients, etc. The HMD 140 may include one or more back facing cameras (e.g. visible light, near infrared, short wavelength infrared, medium wavelength infrared, coherence tomography scanners, imaging sensors, CMOS sensor arrays, laser speckle imaging sensors, combinations thereof, etc.), so as to image one or more of an ocular parameter, an eye, a pupil, an iris, a feature, discoloration, muscle movement thereof, a skin site, a facial patch of skin, features thereof, or the like of the subject 1.

In aspects, a patch/module pair may be adapted for placement almost anywhere on the body of a subject 1. As shown in FIG. 1a, some sites may include attachment to the cranium or forehead 131, the temple, the ear or behind the ear 50, the neck, the front, side, or back of the neck 137, a shoulder 105, a chest region with minimal muscle mass 100, integrated into a piece of ornamental jewelry 55 (may be a host, a hub, a feedback device, etc.), arrangement on the torso 110a-c, arrangement on the abdomen 80 for monitoring movement or breathing, below the rib cage 90 for monitoring respiration (generally on the right side of the body to substantially reduce EKG influences on the measurements), on a muscle such as a bicep 85, on a wrist 135 or in combination with a wearable computing device 60 on the wrist (e.g. a smart watch, a fitness band, etc.), on a buttocks 25, on a thigh 75, on a calf muscle 70, on a knee 35 particularly for proprioception based studies and impact studies, on a shin 30 primarily for impact studies, on an ankle 65, over an Achilles tendon 20, on the front or top of the foot 15, on a heel 5, or around the bottom of a foot or toes 10. Other sites for placement of such devices are envisioned. Selection of the monitoring sites is generally determined based upon the intended application of the patch/module pairs described herein.

Additional placement sites on the abdomen, perineal region 142*a-c*, genitals, urogenital triangle, anal triangle, sacral region, inner thigh 143, or the like may be advantageous in the assessment of autonomic neural function of a subject. Such placements regions may be advantageous for assessment of PNS activity, somatosensory function, assessment of SNS functionality, etc.

Placement sites on the wrist 144*a*, hand 144*b* or the like may advantageous for interacting with a subject, such as via performing a stress test, performing a thermal stress test, performing a tactile stress test, monitoring outflow, afferent traffic, efferent traffic, etc.

Placement sites on the nipples, areola, lips, labia, clitoris, penis, the anal sphincter, levator ani muscle, over the ischiocavernous muscle, deep transverse perineal muscle, labium minus, labium majus, one or more nerves near the surface thereof, posterior scrotal nerves, perineal membrane, perineal nerves, superficial transverse perineal nerves, dorsal nerves, inferior rectal nerves, etc. Such placement may be advantageous for assessment of autonomic neural ablation procedures, autonomic neural modulation procedures, assessment of the PNS of a subject, assessment of sexual dysfunction of a subject, etc.

Placement sites on the face 141, over ocular muscles, near the eye, over a facial muscle (e.g. a nasalis, temporalis, zygomaticus minor/major, orbicularis oculi, occipitofrontalis), near a nasal canal, over a facial bone (e.g. frontal process, zygomatic bone/surface, zygomaticofacial foreman, malar bone, nasal bone, frontal bone, maxilla, temporal bone, occipital bone, etc.), may be advantageous to assess ocular function, salivary function, sinus function, interaction with the lips, interaction with one or more nerves of the PNS (e.g. interacting with the vagus nerve within, on, and/or near the ear of the subject), etc. In aspects, one or more facial interactions may be provided by an HMD 140 in accordance with the present disclosure.

In aspects, a system in accordance with the present disclosure may be configured to monitor one or more physiologic parameters of the subject 1 before, during, and/or after one or more of, a stress test, consumption of a medication, exercise, a rehabilitation session, a massage, driving, a movie, an amusement park ride, sleep, intercourse, a surgical, interventional, or non-invasive procedure, a neural remodeling procedure, a denervation procedure, a sympathectomy, a neural ablation, a peripheral nerve ablation, a radio-surgical procedure, an interventional procedure, a cardiac repair, administration of an analgesic, a combination thereof, or the like. In aspects, a system in accordance with the present disclosure may be configured to monitor one or more aspects of an autonomic neural response to a procedure, confirm completion of the procedure, select candidates for a procedure, follow up on a subject after having received the procedure, assess the durability of a procedure, or the like (e.g. such as wherein the procedure is a renal denervation procedure, a carotid body denervation procedure, a hepatic artery denervation procedure, a LUTs treatment, a bladder denervation procedure, a urethral treatment, a prostate ablation, a prostate nerve denervation procedure, a cancer treatment, a pain block, a neural block, a bronchial denervation procedure, a carotid sinus neuromodulation procedure, implantation of a neuromodulation device, tuning of a neuromodulation device, etc.).

FIG. 1*b* shows a series of patch/module pairs 150*a-e* each in accordance with the present disclosure placed upon a subject 2 as part of a monitoring session in accordance with the present disclosure, in this case an EKG monitoring session. An image 152 of the subject 2 has been taken and may be analyzed in accordance with the present disclosure to calculate one or more standard lead configurations from the arrangement of patch/modules 150*a-e* shown. The subject 2 may interface with an HMD 140 in accordance with the present disclosure, the HMD 140 configured so as to provide audio, visual, and optionally olfactory stimuli to the subject, the HMD 140 configured to monitor one or more physiologic parameters, ocular parameters, etc. from the subject 2 during use.

FIG. 1*c* shows aspects of communication between subjects 155, 160 and non-subject users 156, 161 partaking in a monitoring session in accordance with the present disclosure. In a first aspect, the subject 155 is wearing a head mounted display 159, and/or a series of patches and modules each in accordance with the present disclosure configured to communicate with one or more of a host device 158, a display 157*b*, a display to provide one or more functions of a HUD, a pair of virtual reality goggles, a Google Glasses™ based feedback device 157*a* (i.e. potentially via a smartphone hub), or the like. The user 156 is also shown wearing a wristwatch 157*c* configured for communicating one or more feedback signals in accordance with the present disclosure to the user 156.

In aspects, the subject 160 may wear a head mounted display 164 in accordance with the present disclosure, and/or a series of patches and modules each in accordance with the present disclosure configured to communicate with one or more of a host device 163, a display 162*b*, a virtual reality headset, a HUD, a Google Glasses™ based feedback device 162*a* (i.e. via a smartphone hub), a wristwatch 162*c*, and/or one or more patches and/or modules configured upon the body of the user 161 to communicate one or more feedback signals in accordance with the present disclosure to the user 161 or to convey one or more sensations to the body of the user 161 (i.e. via the attached patches). In aspects, the ocular feedback device 164, may be used to perform a visual and/or audible stress test on the subject, one or more aspects of the feedback device 164, or an associated patch configured to monitor the response of one or more aspects of the ANS to the stress test.

In aspects, the communication between the subject 155, 160 and the user 156, 161 may be bidirectional (i.e. the subject 155, 160 may also receive information corresponding to physiologic and/or physical information obtained from the user 156, 161).

Figure 2:
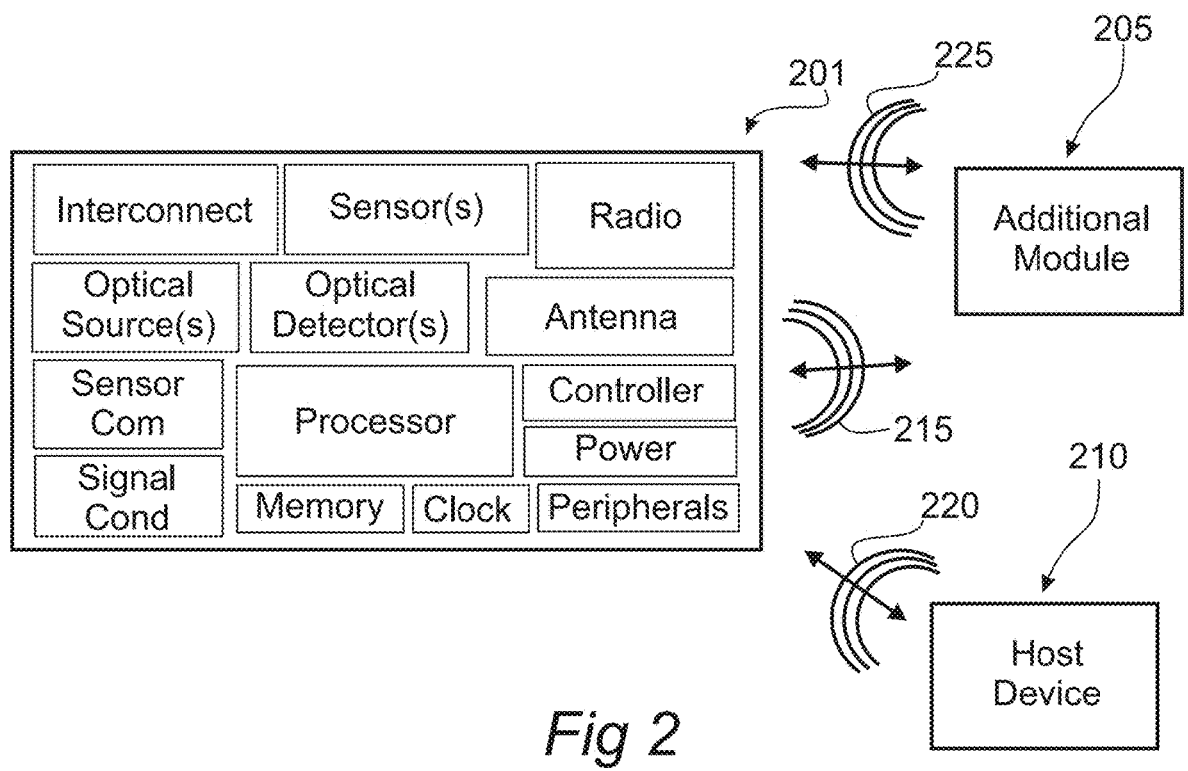
FIG. 2 shows a schematic of aspects of a module in accordance with the present disclosure.

FIG. 2 shows a schematic of aspects of a module 201 in accordance with the present disclosure. The module 201 includes one or more of interconnects, sensors, optical source(s), optical detector(s), a radio, an antenna, a sensor communication circuit, a signal conditioning circuit, a processor, a memory device, a controller, a power supply, power management circuit, and/or energy harvesting circuit, and one or more peripherals each in accordance with the present disclosure. The module 201 is shown in wireless communication 215, 225, 220 with an additional module 205 (e.g.

perhaps situated in the same monitoring system, on the same subject, etc.), and a host device 210. Further aspects of the module 201 are discussed throughout this disclosure. The module 201 may include a stimulator (e.g. a thermal regulating unit, a Peltier device, an electrical stimulator, a tactile stimulator, a vibrating motor, or the like), to interface with the tissue site of the subject. Such a stimulator may be advantageous for providing a stimulus to a site on the body of the subject, as part of a stress test in accordance with the present disclosure, for a haptic interfacing application, for communicating touch between remotely situated subject, for conveying an emotional state of a first user to a tissue site on the subject, etc.

FIGS. 3a-3c show aspects of multi-site monitoring, stimulation, stress application, and/or treatments applied to a subject each in accordance with the present disclosure. FIG. 3a illustrates a subject 25 adorned with a plurality of patches 301, 303, 305, 307, 309, 311, 313, each patch configured to interface with the subject, measure one or more physiologic parameters from the subject, apply one or more stimulatory inputs to the subject, or the like. The subject 25 is shown wearing an HMD 302, in accordance with the present disclosure, the HMD 302 configured so as to monitor one or more facial physiologic parameters of the subject 25. In aspects, the subject 25 may be wearing a temporally applied patch 301, arranged near to the eye of the subject 25. A temporally applied patch 301 may be configured to monitor one or more ocular inputs, facial muscle tone, ocular muscle tone, neural traffic associated with the eye, the retina, pupil dilation, iris function, iris feature movement, blink rate, lacrimal gland function, a neural ganglion (e.g. such as may be related to the onset of cluster migraine headaches, etc.), or the like via inclusion of one or more sensors each in accordance with the present disclosure. In aspects, the temporally applied patch 301 may include one or more energy or stimulus delivery elements, a thermal regulating unit, an electrical stimulator, a light source, a tactile stimulator, etc. in order to stress the subject near to the ocular circuits. A neck applied patch 303 has been applied to the subject 25. The neck applied patch 303 may be configured so as to monitor one or more muscular activities, thyroid and/or parathyroid activities, neural traffic along the carotid artery, activity around the carotid sinus, near the carotid body, muscular tone along the larynx, trachea, swallowing activity, choking, occlusion, etc. In aspects, the neck applied patch 303 may include one or more energy or stimulus delivery elements, a vibratory stimulating element, a tactile stimulating element, an electrical stimulator, a thermal regulating unit, etc. in order to stimulate one or more neural structures in the neck of the subject 25. Such stimulation may be advantageous to interact and/or stimulate one or more neural structures, nerves, and/or receptors such as near to or within a carotid sinus, a carotid body, a vagus nerve plexus, a baroreceptor, a chemoreceptor, a cutaneously innervated region of tissue, or the like located in the neck of the subject 25.

A groin applied patch 305 has been applied to the subject 25. The groin applied patch 305 may be configured to monitor one or more of an autonomic nerve activity, a peroneal nerve activity, a pudendal nerve activity, a lumbar sympathetic nerve activity, a dorsal nerve activity, a splanchnic nerve activity, a hypogastric plexus activity, a femoral nerve activity, a popliteal nerve activity, a scrotal nerve activity, activity in a cutaneously innervated volume of tissue, SNS activity, PNS activity, somatosensory activity, local tissue perfusion, local sweating, local EMG, local smooth muscle EMG, etc. In aspects, the groin applied patch 305 may include one or more energy or stimulus delivery elements, a vibratory stimulating element, a tactile stimulating element, an electrical stimulator, a thermal regulating unit, etc. in order to stimulate one or more neural structures in the groin of the subject 25.

A thigh applied patch 307 has been applied to the subject 25. The thigh applied patch 307 may be positioned so as to record cutaneous innervation related to an obturator plexus, an anterior femoral plexus, a lateral femoral plexus, a branch thereof, of the like. In aspects, the thigh applied patch 307 may include one or more energy or stimulus delivery elements, a vibratory stimulating element, a tactile stimulating element, an electrical stimulator, a thermal regulating unit, etc. in order to stimulate one or more neural structures in the neck of the subject 25. In aspects, the thigh applied patch 307 may be arranged such that physiologic signals associated with substantially different neural plexuses may be simultaneously recorded on the subject 25, the differential response measured between the different plexuses may be used to characterize the state, the stress-state response, the health of the ANS of the subject, to assess a local neural block (e.g. to one of the two plexuses, etc.), assess a state or progression of peripheral neuropathy, etc.

In aspects, one or more patches 315 (not explicitly shown) in accordance with the present disclosure, may be applied to the ankle, lower limb, foot, or hand of the subject 25.

A torso applied patch 309 is shown applied to the subject 25. The torso applied patch 309 may be configured to monitor one or more physiologic parameters, EKG, heart rate, heart rate variability, cutaneous nerve activity, nipple, areola, near a sebaceous gland, traffic associated with a branch or receptor coupled to the thoraco-dorsal nerve, the thoracic nerve, branches from the second, third, fourth, fifth, and/or sixth intercostal nerves, tissue within the superficial fascia, the subdermal tissue of the areola, the intercostal brachial nerve, neural structures coupled thereto, innervation near the axilla, nerve traffic near the axilla, the axillary nerve, ulnar nerve, intercostalis nerve, or the like.

In aspects, one or more patches in accordance with the present disclosure may be used to plan a plastic surgical procedure. In one non-limiting example, the innervation to the breast of a subject varies widely from person to person. Assessment of somatosensory innervation of breast tissues with one or more patches in accordance with the present disclosure may be used to develop a personalized nerve map, to determine which nerves are critical to preserving sensory function of the nipple, areola, etc. of a subject, or the like. Based upon the neural activity mapped around the breast, the surgical approach may be planned so as to avoid key nerve plexuses associated with the sensory function to be preserved. Such a process may be advantageous for performing nerve sparing plastic surgeries, restoration of sensation to a tissue volume in a region of a subject, nerve sparing tumor excision surgeries, etc.

An abdominally applied patch 311 has been attached to the subject 25. The abdominally applied patch 311 may be configured to monitor respiration, posture, movement, to generate a feedback signal associated with the respiration to help guide the subject in breathing (e.g. to help control the breathing rate, breathing depth, diaphragmatic breathing of the subject, etc.), skin neural activity, autonomic neural activity, etc. In aspects, the abdominally applied patch 311 may include one or more energy or stimulus delivery elements, a vibratory stimulating element, a tactile stimulating element, an electrical stimulator, a thermal regulating unit, etc. in order to stimulate one or more neural structures in the abdominal region of the subject 25.

A hand applied patch 313 has been attached to the subject 25. The hand applied patch 313 may include one or more sensors each in accordance with the present disclosure, arranged so as to interface with one or more regions of the hand (e.g. palm, wrist, fingers, median nerve branches, radial nerve branches, ulnar nerve branches, and the like). In aspects, the hand applied patch 313 may be integrated into a glove, a wrist band, etc. so as to be worn by the subject 25. In aspects, the hand applied patch 313 may include one or more energy or stimulus delivery elements, a vibratory stimulating element, a tactile stimulating element, an electrical stimulator, a thermal regulating unit, etc. in order to stimulate one or more neural structures in the hand or wrist of the subject 25. In aspects, the patch 313 or patch/module pair may include a thermoelectric thermoregulating device, the thermoelectric device configured so as to heat, cool, and/or maintain a temperature of one or more skin surfaces on the hand or wrist. In aspects, the thermoelectric device includes a Peltier element, a power supply, and a controller, the thermoelectric device configured so as to cool the tissues of the hand, warm the tissues of the hand, etc.

In aspects, a stimulus applied to one or more regions of the body of the subject 25 and the resulting physiologic changes thereof may be monitored by one or more of the patches 301, 303, 305, 307, 309, 311, 313, etc. The HMD 302 may be configured to provide one or more stimulating inputs to the subject 25 such as a visual field, audio field, an eye selective visual field, an ear selective audio field, light input, a visual cue, an audio visual presentation, a light show, a varying ambient light input, etc. Such stimulations may be coordinated, applied sequentially, in parallel, isolated, provided as part of a stress test in accordance with the present disclosure, etc. Such a multi-site monitoring and/or stimulating configuration may be advantageous to assess the functional relationship between a stress input at one site on the body, to an afferent response to the stress at the site, to an efferent response at one or more sites on the body (i.e. sites innervated to varying degrees by one or more autonomic and/or somatosensory branches), etc.

In aspects, a stimulus may be applied to the subject via a neck applied patch 303, the stimulus of sufficient amplitude so as to elicit a response from a baroreceptor in the carotid sinus, and/or to interface with one or more neural circuit in the carotid body of the subject 25. The patches 301, 303, 305, 307, 309, 311, 313 configured so as to monitor local responses to the stimulus, signals generated from one or more of the patches 301, 303, 305, 307, 309, 311, 313 to be communicated to a processor in accordance with the present disclosure. The processor may be programmed with machine readable code so as to accept the signals, condition the signals, analyze the signals, generate one or more metrics therefrom, compare the metrics against a patient history, a patient population, a database of disease state responses, etc. so as to perform an assessment on the subject 25. In aspects, such a procedure may be advantageous to assess the cardiac baroreflex sensitivity (BRS) of the subject (e.g. such a procedure may be a predictor of the response of a subject to a renal denervation procedure (RDN), etc.).

FIG. 3b shows a multi-site system for assessing the response of a subject 27 to a stress test, assessment of the ANS of the subject 27, response of the subject 27 to an interventional procedure, state of completion of an ANS affecting interventional procedure, etc. The subject 27 is adorned with a plurality of patches in accordance with the present disclosure 301, 303, 305, 307, 309, 311, 313, 315, etc. The subject 27 is shown wearing an HMD 302, in accordance with the present disclosure, the HMD 302 con- figured so as to monitor one or more facial physiologic parameters of the subject 27. One or more delivery tools 321a,b may be subcutaneously, endovascularly, percutaneously, transcutanesouly, etc. interfaced with the subject 27 so as to perform a procedure, deliver a substance, perform a stress test, etc. upon the subject 27, the patches 301, 303, 305, 307, 309, 311, 313, 315, and/or the HMD 302 configured to monitor the response to the procedure, delivery, stress test, etc. on the subject 27 and, in aspects, to stimulate and/or apply one or more additional stress tests to the subject 27. The delivery tool(s) 321a,b may be used to deliver 323a,b a substance in accordance with the present disclosure, energy (e.g. as part of a neural blocking, neurostimulation, denervation, etc.), or the like as part of a stress test, procedure, etc. Although a first delivery tool 321a is illustrated on the wrist of the subject 27 interfacing with an artery or vein in the vicinity thereof, and a second delivery tool 321b is shown interfacing with the thigh of the subject 27 interfacing with an artery or vein in the vicinity thereof, a delivery tool 321a,b may interface with substantially any artery, vein, or vessel in the subject 27.

FIG. 3c shows a multi-site system for assessing the response of a subject 29 to a stress test, assessment of the ANS of the subject 29, response of the subject 29 to a procedure, state of completion of an ANS affecting procedure, etc. The subject 29 is adorned with a plurality of patches in accordance with the present disclosure 301, 303, 305, 307, 309, 315, etc. The subject 29 is shown wearing an HMD 302, in accordance with the present disclosure, the HMD 302 configured so as to monitor one or more facial physiologic parameters of the subject 29. The subject 29 is positioned near to one or more energy delivery transducers 325a,b (e.g. HIFU transducers, MR guided HIFU transducers, radiosurgical transducers, proton therapy, x-ray therapy, etc.). As shown in FIG. 3c, the subject 29 is interfaced with a pair of HIFU delivery transducers 325a,b (could be a single tranducer, a transducer array, multiple transducer arrays, etc.), and a focused delivery of energy 327a,b towards a target site 329 in the body of the subject 29. The patches 301, 303, 305, 307, 309, 315, and/or the HMD 302 may be configured to monitor one or more aspects of the energy delivery 327a,b (e.g. such as time of flight assistance for the HIFU delivery transducers 325a,b, assessment of reflections, assessment of energy delivery levels near critical tissue sites, etc.), and/or the response of the subject 29 to the procedure, assess the completion of the procedure 29 via a method in accordance with the present disclosure, etc. In aspects, the energy delivery 327a,b may be part of an ablation procedure, a tumor treatment, administration of a neural block, a sympathectomy, a local neural stimulation, a peripheral nerve treatment, a treatment for inflammation at a site in the subject, a neuromodulation procedure, combinations thereof, or the like. In aspects, such a system and/or method may be advantageous to confirm completion of, follow up on, partial completion of, a patient response to, etc. a denervation procedure, a renal denervation procedure, ablation of a renal nerve, ablation of renal artery, an accessory renal artery, a stress test, or the like.

According to aspects there is provided a method for treating one or more neural structures in the vicinity of an artery, a renal artery, an accessory renal artery, or the like, including monitoring autonomic neural activity and/or a closely tied surrogate thereof, at one or more sites on or in the body, applying a test bolus of energy (e.g. a substantially low dosage of ultrasound energy, radiation, thermal energy, etc. so as to affect but not substantially damage tissues), in the vicinity of a suspected treatment site (e.g. a site where a target vessel, neural structure, etc. is suspected but not entirely confirmed due to a lack of adequate imaging in the vicinity of the target vessel, lack of distinguishing features of the suspected target area, lack of confirmation of the destination for nerves traveling through the target area, etc.), and assessing the response to the test bolus to determine if the suspected treatment site includes the target neural structures (e.g. autonomic nerves, vessels innervated with such nerves, one or more ganglia, etc.), and if so, performing a substantially durable treatment at the now confirmed treatment site, if not testing another suspected treatment site, or finishing the procedure. In aspects, one or more steps included in a method in accordance with the present disclosure may be applied so as to test various aspects of the treatment, the subject response to the treatment, predict outcome of the treatment, select patients for suitability of performing a treatment, etc. In aspects, one or more of the steps of the method may be monitored and/or performed by a patch and/or an HMD in accordance with the present disclosure.

FIGS. 4a-4c illustrate aspects of methods for monitoring, stressing, and/or treating one or more regions of a subject each in accordance with the present disclosure. FIG. 4a illustrates aspects of a method for modulating or assessing neural traffic in accordance with the present disclosure. The method includes interfacing one or more systems, devices, patches, patch/module pairs, and/or an HMD each in accordance with the present disclosure to a subject, optionally accessing one or more target sites within a body, applying a stress test in accordance to the present disclosure to the subject, treating one or more tissues in accordance with the present disclosure, administering a medication to the subject, treating the optional target site, stimulating, sensing, or ablating one or more nerves in the subject, augmenting neural activity, treating the afferent nerves and/or receptors, and optionally evaluating one or more physiologic responses, nerve activity, specific nerve activity, a combination thereof, or the like, pre/post stress test, procedure, treatment, etc. to determine if the traffic has been modulated. In aspects, the evaluation may be performed by comparing a physiologic and/or nerve activity metric before and after treatment (e.g. a change in integrated activity level, a change in phasic response such as a shift from a biphasic polarity to a monophasic polarity, a change in action potential firing rate, a change in the spectral content of the firing, etc. associated with the local neural tissues), a differential response between metrics, combinations thereof, or the like. In aspects, the method may include performing a neural block, a temporary neural block, varying a pressure applied to one or more nerves in the subject, stimulating the nerves, and/or receptors, and monitoring afferent nerve activity during such changes in block, stimulus, applied pressure (i.e. monitoring activity during a variable pressure compression block), etc.

Additionally, alternatively, or in combination with the monitoring of physiologic response and/or electrophysiological activity, the method may include monitoring one or more additional physiologic parameters in accordance with the present disclosure and assessing changes in the parameters before, during, and/or for a period of time following application of a procedure to the target tissues. In aspects, the additional physiologic parameter may be monitored from a catheter, a pressure sensing catheter, an analyte sensing catheter, a plethysmograph, etc.

One or more of the steps may be completed with a guidewire or surgical tool in accordance with the present disclosure. One or more steps may be completed with a radiosurgical system, a HIFU system, a proton therapy device, an ablation catheter, an ablation system, a chemical delivery catheter, combinations thereof, and the like.

FIG. 4b illustrates a method for assessing the neural structures in the vicinity of a target organ. The method includes interfacing one or more systems, devices, patches, patch/module pairs, and/or an HMD each in accordance with the present disclosure to a subject, optionally accessing one or more target sites within a body, accessing/monitoring (such as communicating with, recording activity from, etc.) one or more neural structures in the body, the nerves associated with the target organ, a related ANS circuit, a skin sympathetic nerve, a skin parasympathetic nerve, a somatosensory nerve, a physiologic parameter, one or more sites related to the disease state to be treated, etc. The method may include monitoring an initial activity level, signal character, periodic element to a signal, afferent or efferent traffic proportion of the neural traffic, etc. The method may include monitoring such activity or metrics associated therewith during a stress test in accordance with the present disclosure as applied to the organ, or subject as a whole, a vessel, a skin surface, a tissue volume, etc. The method may include generating and/or analyzing a metric associated with the change in the monitored activity and determining a suitability of the subject for performing a surgical procedure, determining a proportion of nerve types amongst the captured responses, determining if the nerves require treatment, determining the influence of the stressor on the locally measured electrophysiological activity, or the like.

The method may include modulating a functionality of, neural activity from, afferent activity from, or the like of the target organ of a subject, the method may include selectively stimulating and/or stressing one or more regions of the target organ and monitoring the physiologic response at one or more sites nearby and/or systemically to the stimulus/stress. In aspects, the stimulus/stress response may be used to identify regions of the target organ that are suitable for neuromodulation to treat a particular condition. In aspects, the method may include selectively treating one or more sites within or in the vicinity of the target organ. In aspects, the method may include monitoring activity and/or local physiologic response to the treatment at one or more of the sites to determine the extent of the procedure, to evaluate when the procedure has been completed, to decide whether or not to continue with the procedure, etc. The method may include ablating a portion of the organ, or a neurological structure coupled thereto, in accordance with the present disclosure. In aspects, the method may include using a surgical system, an interventional device, a guidewire, a catheter, an ablation catheter, and/or a surgical device in accordance with the present disclosure to perform one or more of the above steps.

The method may include establishing a baseline state for the subject, such as by stimulating the subject, performing a stress test on the subject, establishing a controlled sensory environment around the subject, providing a controlled audio visual experience for the subject using an HMD in accordance with the present disclosure, and monitoring one or more baseline physiologic responses thereto, the monitored baseline physiologic responses being used for comparison with future test results, previous test results, a procedural outcome, a patient population, etc.

FIG. 4c shows aspects of a method for treating one or more neural structures in or at a site within a subject. The method including accessing the target site (e.g. with a catheter, a guidewire, via a focused energy delivery system, with a chemical substance, etc.), optionally monitoring activity in one or more regions around the target site, treating the nerves, and assessing based on a change in the activity if the treatment was successful. In aspects, the assessment may be determined based on a change in activity level (e.g. pulses per unit of time, drop out of pulses associated with a particular nerve type, changes in traffic associated with a neural circuit biorhythm, a change in subject pain levels, etc.), a shift in the polarity of the signals (i.e. a transition from a biphasic signal related to multi-directional traffic near the vessel, to a monophasic signal related to changes more representative of a uni-directional traffic near the vessel), a drop off in periodic behavior in the captured signals, or the like. In aspects, the, assessment may be determined by combining and/or comparing activity measured at multiple sites on or within the subject, associated vessels, or the like. Such comparison may include assessing a change in coherence between two signals collected from different nearby sites, from a change in one signal with respect to the other signal collected from nearby sites, a change in a representative transfer function representative of a correlation between the traffic at one site and the other site, etc.

If, after the first test, procedure, treatment dose, etc. a response was recognized, a subsequent test, procedure, treatment dose, may be performed to confirm completion of the first test, procedure, treatment dose, etc. If the response occurs again, if a substantial change is monitored after the subsequent test, procedure, treatment dose, etc. further tests, procedures, treatments, etc. may be required to complete the intended task (e.g. neural block, substantially durable neural block, neural remodeling, neuromodulation, stimulating neural block, or the like). If the response was not observed after the subsequent test, procedure, treatment dose, etc. then the second test, etc. substantially served as a confirmation of adequate dose, etc. applied to the target site(s) of the subject.

The assessment may include determining if a change in one or more homeostatic functions of the organ have changed in a desired direction, if the response of the neural traffic to a stress test has changed as desired by the therapy, assessing if the subject feels the same, increased, or decreased pain compared with an assessment made before the procedure. If the treatment has been finished, complete the procedure, pull out any system component in the subject, etc. otherwise, monitor activity, continue with treatment, and/or move to a new treatment site in the vicinity of the target site.

In aspects, an ablation may be performed so as to minimize damage to surrounding tissues. The ablation may include delivering energy to the local tissues in an amount just sufficient to induce irreversible damage to one or more adjacent nerves, but not in an amount sufficient to irreversibly damage other surrounding tissues.

In aspects, a method in accordance with the present disclosure may be used to assess the durability of a previously applied treatment to a subject. In aspects, a system, a device, a patch, a patch/module pair, an HMD, and/or a method in accordance with the present disclosure may be used for non-invasive sensing of neurological tone or closely coupled surrogates thereof as pertaining to diagnostics, patient selection, procedural feedback, and follow-up assessment of autonomic neural ablation procedures.

Figure 5A:
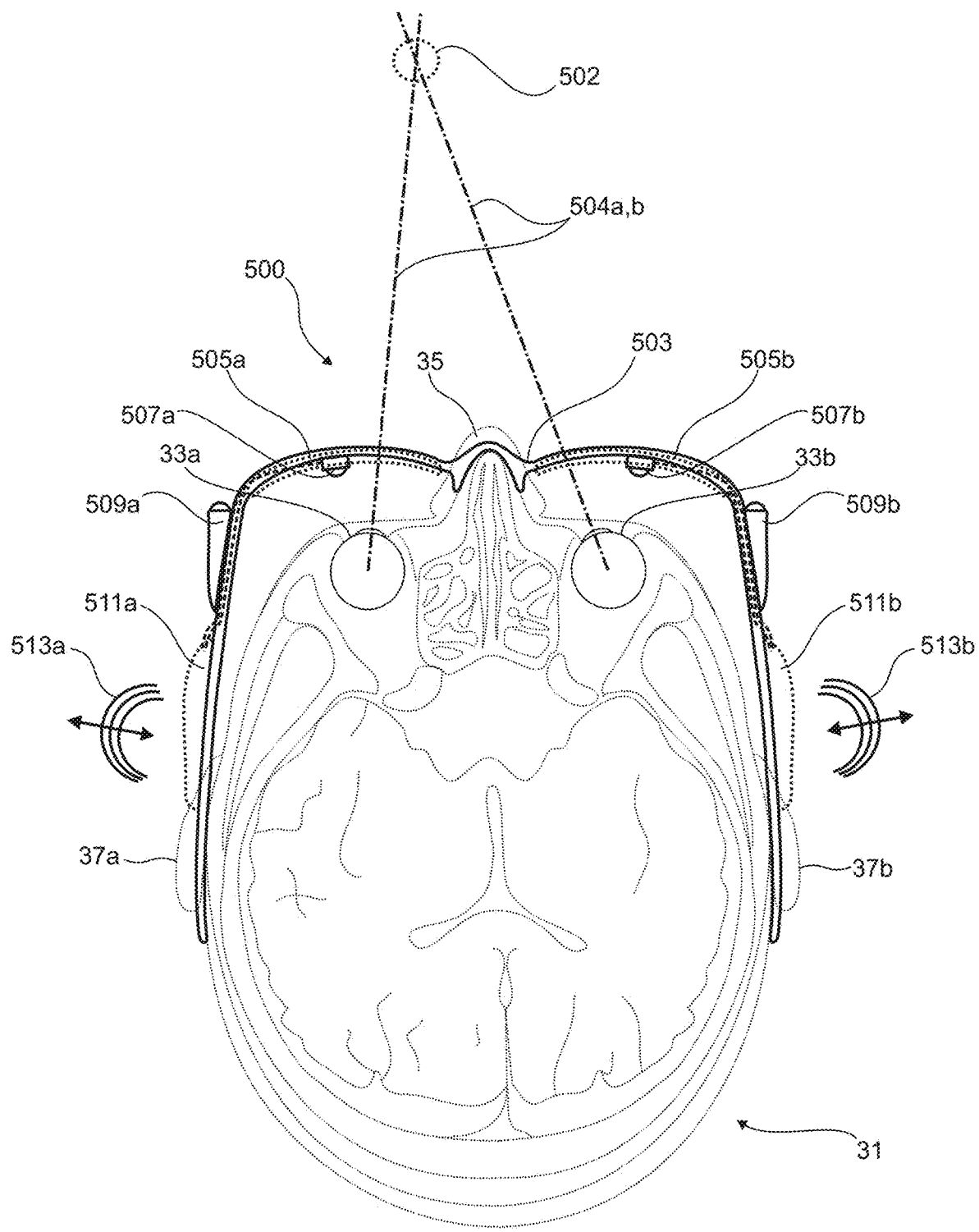

FIGS. 5a-5c illustrate aspects of head mounted displays (HMD) each in accordance with the present disclosure. FIG. 5a shows aspects of a head mounted display (HMD) 500 in accordance with the present disclosure. The HMD 500 is shown mounted on the head 31 of a subject, the HMD 500 including a frame 503 with features for optionally securing the HMD 500 to the head 31 of the subject along the nasal bridge 35 and the ears 37a,b of the subject. In aspects, the frame 503 may be shaped and formed so as to isolate the eyes 33a,b of the subject from the surroundings (i.e. so as to allow for control of the visual field seen by the subject while wearing the HMD 500). The HMD 500 may include one or more visual input devices 505a,b (e.g. including one or more of a display, an LED, a visible light LED, a broadband light source, one or more narrow band light sources, an IR light source, a UV light source, an IR LED, a light source array, a curved display, an AMOLED display, a flexible AMOLED display, a transparent display, a smart glass display, an electrochromatic film, etc.). The HMD 500 may include one or more back-facing imaging sensors 507a,b (e.g. including one or more of a camera, a visible light camera, a near infrared camera, an infrared camera, a CMOS imaging sensor, an IR imaging sensor, a laser speckle imaging sensor, a coherence tomographic imaging element, combinations thereof, or the like). The visual input devices 505a,b and the imaging sensors 507a,b are mounted on the frame 503 so as to be within the visual field of one or more eyes 33a,b of the subject. In aspects, one or more portions of a visual input device 505a,b may be used to provide illumination for one or more of the imaging sensors 507a,b. In aspects, one or more of the imaging sensors 507a,b may include an infrared or near infrared camera, and one or more of the visual input devices 505a,b may include a near infrared, and/or infrared LEDs for illuminating the ocular features of the subject.

In aspects, the visual input devices 505a,b may be configured so as to adjust, flicker, sequentially illuminate, etc. different regions of the ocular features of the subject, or adjust the light field around the ocular features of the subject such that one or more finer details (i.e. features of interest), may be highlighted for capture by one or more of the imaging sensors 507a,b. In aspects, the generated light field My be strong in and/or may pulse, alternate, and/or flicker in the near infrared, and/or infrared light band so as to illuminate the ocular features of the subject for one or more of the imaging sensors 507a,b without influencing the physiological processes of the subject. In aspects, the visual input devices 505a,b may include an array of infrared LEDs oriented such that a different quadrant of the eyes 33a,b of the subject may be highlighted during each frame captured by the imaging sensors 507a,b. Such an approach may be advantageous to capture finer details (e.g. such as by temporarily enhancing contrast in different regions of the eye, moving bright spots, etc.), in regions of the eye, iris, retina, etc. of the subject while altering the location of a glare, bright spots, etc. on the eye, which may interfere with the image capture.

The HMD 500 is also shown optionally including one or more front facing imaging sensors 509a,b (e.g. cameras, near infrared cameras, photodetectors, bolometers, etc.). The front facing imaging sensors 509a,b may be attached to the frame 503, such that an environment around the head 31 of the subject may be captured during use.

The HMD 500 may include one or more externally facing positioning markers (e.g. an near infrared light, a light, a fiducial marker, etc.).

The visual input device 505a,b, the back facing imaging sensors 507a,b, and the front facing imaging sensors 509a,b, are coupled to one or more processors 511a,b included in the HMD 500 (as shown), or coupled to the HMD 500 but not embedded therein. A coupled processor (not explicitly shown), may be configured to communicate 513a,b wirelessly with one or more microcircuits, processors, 511a,b, or the like included in the HMD 500. In aspects, the processors 511a,b may be embodied as HDL code, embedded into an ASIC, a FPGA, a DSP, and/or provided as part of a microcontroller, an embedded system, etc. The processors 511a,b may coordinate receipt of one or more images, video streams, etc. from the front-facing imaging sensors 509a,b, the back facing imaging sensors 507a,b, and may coordinate update of one or more aspects of the visual input device 505a,b (e.g. such as update a video thereto, a stereoscopic video, an image, a light field, an LED lighting sequence, a lighting intensity adjustment, etc.).

In aspects, the processors 511a,b may be configured to analyze one or more images captured by one or more of the imaging sensors 507a,b so as to analyze the eyes 33a,b of the subject to determine a gaze of the subject, the optical axis 504a,b of each eye 33a,b converging on a focal region 502, the optical axis 504a,b of each eye 33a,b being determined based upon the pupil positioning, iris feature, iris feature shapes, eye 33a,b positions, etc. with respect to the imaging sensors 507a,b. In aspects, the imaging sensors 507a,b may be configured to determine one or more biometrics associated with the eyes 33a,b of the subject. In aspects, the processors 511a,b may be configured so as to incorporate one or more biometrics into a display calibration algorithm (i.e. so as to customize the display to the subject), etc. The calibration algorithm may include a step wherein one or more visual fields are displayed to the subject, the subject questioned (such as visually in the display, audibly, etc.), and the subject can respond to the question so as to assess a lens function of an eye 33a,b of the subject, adjust for the eyes 33a,b of the subject, etc.

In aspects, the HMD 500 may be configured to provide one or more aspects of a visual presentation to the subject as part of a stress test in accordance with the present disclosure. The HMD 500 may be configured to monitor one or more physiologic parameters, facial parameters, ocular parameters, etc. in accordance with the present disclosure during use. Such information may be useful for determining the response of the subject to a stress test, a procedure, for patient selection purposes, as part of a gaming experience, to determine an emotional response of the subject to a suggestion, or the like.

FIG. 5b shows a schematic of aspects of an HMD 520 in accordance with the present disclosure mounted upon the head 31 of a subject, the HMD 520 including one or more visual input devices 525a,b, one or more back-facing imaging sensors 527a,b, each in accordance with the present disclosure and arranged along the frame 523 of the HMD 520 so as to interact with the visual field of one or more eyes 33a,b of the subject. The HMD 520 includes one or more audio input devices 535a,b (e.g. audio transducers, speakers, ear buds, etc.) arranged so as to interface with the ears 37a,b of the subject during use. The HMD 520 includes a facial interfacing member 537, coupled to the frame 523, the facial interfacing member 537 arranged so as to bias 541 against one or more regions of the head 31 of the subject when the HMD 520 is donned thereupon. The facial interfacing member 537 may include one or more flexible elements for providing the bias 541, one or more padded elements, a rubberized enclosure, etc. In aspects, the facial interfacing member 537 may be arranged so as to visually isolate the eyes 33a,b of the subject from the surrounding environment (e.g. so as to control the lighting reaching the eyes 33a,b of the subject, so as to provide a controlled lighting environment for assessing the ocular parameters of the subject, to keep sunlight away from one or more of the back-facing imaging sensors 527a,b, a shroud-like covering, a substantially opaque barrier, or the like). In aspects, the facial interfacing member 537 may be configured to interface with one or more of the forehead, eyebrow, temple region, ocular region, cheeks, jaw, nasal region, mouth, near an orbital bone, near a sinus, or the like of the subject when the HMD 520 is donned.

In aspects, the facial interfacing member 537 may be arranged so as to form one or more intimate regions of contact along the face of the subject when the HMD 520 is donned for use. The facial interfacing member 537 may include one or more physiologic sensors and/or electrodes 539a-j (illustrated in FIG. 5b as ellipses with dotted lines) arranged there along, so as to interface with tissues in the vicinity thereof. In aspects, the electrodes 539a-j in accordance with the present disclosure may be biased 541 towards the skin of the subject to form at least part of a circuit for measuring an electrophysiologic parameter, an electroretinogram (ERG), an electrooculogram (EOG), an electromyogram (EMG), an electroencephalogram (EEG), or the like.

The visual input devices 525a,b, the back-facing imaging sensors 527a,b, the audio input devices 535a,b, and the physiologic sensors and/or electrodes 539a-j are shown coupled to one or more processors 531a,b included in the HMD 520 (as shown), or coupled to the HMD 520 but not embedded therein. The physiologic sensors and/or electrodes 539a-j may be coupled to a microcircuit, the microcircuit coupled to the processors 531a,b, the microcircuit including one or more preamplifiers, switch banks, signal conditioning circuits, analog to digital converters, or the like, to transfer one or more signals obtained from the physiologic sensors and/or electrodes 539a-j and convey them to a machine readable form, suitable for analysis, recording, storage, etc. in conjunction with the processors 531a,b. The processors 531a,b may be in communication 533a,b (here shown as wireless communication but it may be wired or otherwise), with one or more host devices, additional processors, cloud services, databases, servers, wireless networks, etc. for conveying information, data streams, etc. there between.

Such a configuration may be advantageous for performing an ERG, EOG, eye tracking test, ocular muscle test, a retinogram, a multifocal retinogram, a combination thereof, or the like. In aspects, a visual field may be provided to the subject via the visual input devices 525a,b (e.g. providing a target to focus upon, providing illumination to the eye 33a,b, providing a visual presentation for the subject, providing one or more point lights for a multifocal retinogram, providing spatially distributed patterns, etc.).

In aspects, the HMD 520 may be configured to provide an audio/visual presentation to the subject during use and to measure one or more physiologic parameters, ocular parameters, pupil diameters, iris characteristics, iris conformal changes, iris sphincter muscle movement, iris dilator muscle movement, ERG, EOG, EMG, EEG, or the like, during the presentation so as to form a response dataset. The response dataset may be provided to an algorithm (e.g. such as programmed onto the processors 531a,b, on a separate processor in communication 533a,b with the HMD 520, etc.). The algorithm may be configured to analyze the response dataset to generate one or more emotional response metrics, one or more metrics associated with the autonomic state of the subject, metrics related to changes in the autonomic state of the subject during the stress test, during a procedure, during execution of a patient selection protocol, etc.

In aspects, the back-facing imaging sensors 527a,b may be configured to assess one or more tissue properties of the face of the subject. Some non-limiting examples of such properties include blood flow, texture, textural changes, piloerection, nasal flare, tissue perfusion, tissue color, tissue reflectance, tissue sheen, sweat response, flush, an analyte level, a hydration level, combinations thereof, or the like.

FIG. 5c shows a schematic of aspects of an HMD 550 in accordance with the present disclosure mounted upon the head 31 of a subject, the HMD 550 including one or more visual input devices 555a,b, one or more back-facing imaging sensors 557a,b, each in accordance with the present disclosure and arranged along the frame 553 of the HMD 550 so as to interact with the visual field of one or more eyes 33a,b of the subject. The HMD 550 includes one or more audio input devices 565a,b (e.g. audio transducers, speakers, ear buds, etc.) arranged so as to interface with the ears 37a,b of the subject during use. The HMD 550 includes a facial interfacing member 567, coupled to the frame 553, the facial interfacing member 567 arranged so as to bias 571 against one or more regions of the head 31 of the subject when the HMD 550 is donned thereupon. The facial interfacing member 567 may include one or more flexible elements for providing the bias 571, one or more padded elements, a rubberized enclosure, etc. In aspects, the facial interfacing member 567 may be arranged so as to visually isolate the eyes 33a,b of the subject from the surrounding environment (e.g. so as to control the lighting reaching the eyes 33a,b of the subject, so as to provide a controlled lighting environment for assessing the ocular parameters of the subject, to keep sunlight away from one or more of the back-facing imaging sensors 557a,b, a shroud-like covering, a substantially opaque barrier, or the like). In aspects, the facial interfacing member 567 may be configured to interface with one or more of the forehead, eyebrow, temple region, ocular region, cheeks, jaw, nasal region, mouth, near an orbital bone, near a sinus, or the like of the subject when the HMD 550 is donned.

In aspects, the facial interfacing member 567 may be arranged so as to form one or more intimate regions of contact along the face of the subject when the HMD 550 is donned for use. The facial interfacing member 567 may include one or more physiologic sensors and/or electrodes 569a-j (illustrated in FIG. 5c as ellipses with dotted lines) arranged there along, so as to interface with tissues in the vicinity thereof. In aspects, the electrodes 569a-j in accordance with the present disclosure may be biased 571 towards the skin of the subject to form at least part of a circuit for measuring an electrophysiologic parameter, an electroretinogram (ERG), an electrooculogram (EOG), an electromyogram (EMG), an electroencephalogram (EEG), or the like.

In aspects, the HMD 550 may include a headband 589 coupled to the frame 553 so as to secure the HMD 550 to the head 31 of the subject when donned. The headband 589 may include a fastener, a size adjustment, a stretchy region, etc. so as to accommodate different sized heads 31. The headband 589 may include one or more additional bands (not explicitly shown) arranged so as to interface with the head 31 out of plane with the image of FIG. 5c. In aspects, the headband 589 may include one or more electrodes 591a-n, each electrode arranged along the headband 589 so as to bias 593 towards a skin site on the head 31 when the HMD 550 is donned. In aspects, the electrodes 591a-n each in accordance with the present disclosure may be biased 593 towards the skin of the subject to form at least part of a circuit for measuring an electrophysiologic parameter, an electromyogram (EMG), an electroencephalogram (EEG), or the like.

In aspects, the HMD 550 may include one or more optical sensors 573a,b, 577a,b, 583 coupled with the frame 553, the audio input devices 565a,b (e.g. integrated into an ear bud, a headphone, etc.), the facial interfacing member 567, the headband 589, etc. The optical sensors 573a,b, 577a,b, 583 may be arranged along the tissues for measuring colorimetric changes in the adjacent tissues during use. One or more optical sensors 573a,b may be arranged along the bridge of the nose 35 of the subject, the optical sensors 573a,b, may be configured to emit/receive energy 575a,b, into/from the adjacent tissues so as to assess one or more physiologic parameters associated therewith. An optical sensor 583 may be arranged along the facial interfacing member 567, such as near a temple of the subject, the optical sensor 583 configured so as to emit/receive energy 585,587 to/from the tissues of the temple. Such an optical sensor 583 may be advantageous for assessing a plethysmograhic property of the tissues, establishing a surrogate recording to blood pressure changes in the subject, assessing local analytes, etc. One or more optical sensors 577a,b may be integrated into an audio input device 565a,b (e.g. an ear bud, a headphone, a hearing aid, an ear clip, etc.) so as to monitor one or more tissue physiologic parameters associated with the tissue of the ear, the ear lobe, the ear canal, etc. The optical sensors 577a,b may be configured to emit 579a,b and/or receive 581a,b energy into/from the adjacent tissues so as to assess one or more physiologic parameters associated therewith.

The visual input devices 555a,b, the back-facing imaging sensors 557a,b, the audio input devices 565a,b, the physiologic sensors and/or electrodes 569a-j, the electrodes 591a-n, and the optical sensors 573a,b, 577a,b, 583 are shown coupled to one or more processors 561a,b included in the HMD 550 (as shown), or coupled to the HMD 550 but not embedded therein. The physiologic sensors and/or electrodes 569a-j, the electrodes 591a-n, and/or the optical sensors 573a,b, 577a,b, 583 may be coupled to a microcircuit, the microcircuit coupled to the processors 561a,b, the microcircuit including one or more preamplifiers, switch banks, signal conditioning circuits, analog to digital converters, or the like, to transfer one or more signals obtained from the physiologic sensors and/or electrodes 569a-j and convey them to a machine readable form, suitable for analysis, recording, storage, etc. in conjunction with the processors 561a,b. The processors 561a,b may be in communication 563a,b (here shown as wireless communication but it may be wired or otherwise), with one or more host devices, additional processors, cloud services, databases, servers, wireless networks, etc. for conveying information, data streams, etc. there between.

Such a configuration may be advantageous for performing an EEG, ERG, EOG, eye tracking test, ocular muscle test, a retinogram, a multifocal retinogram, a combination thereof, or the like. In aspects, a visual field may be provided to the subject via the visual input devices 555a,b (e.g. providing a target to focus upon, providing illumination to the eyes 33a,b, providing a visual presentation for the subject, providing one or more point lights for a multifocal retinogram, providing spatially distributed patterns, etc.).

In aspects, the HMD 550 may be configured to provide an audio/visual presentation to the subject during use and to measure one or more physiologic parameters, ocular parameters, pupil diameters, iris characteristics, iris conformal changes, iris feature movement, iris sphincter movement, iris dilator movement, iris surface strain, ERG, EOG, EMG, EEG, or the like, during the presentation so as to form a response dataset. The response dataset may be provided to an algorithm (e.g. such as programmed onto the processors 561a,b, on a separate processor in communication 563a,b with the HMD 550, etc.). The algorithm may be configured to analyze the response dataset to generate one or more emotional response metrics, one or more metrics associated with the autonomic state of the subject, metrics related to changes in the autonomic state of the subject during the stress test, during a procedure, during execution of a patient selection protocol, etc.

In aspects, the back-facing imaging sensors 557*a,b* may be configured to assess one or more tissue properties of the face of the subject. Some non-limiting examples of such properties include blood flow, texture, textural changes, piloerection, nasal flare, tissue perfusion, tissue color, tissue reflectance, tissue sheen, sweat response, flush, an analyte level, a hydration level, combinations thereof, or the like.

The HMDs 500, 520, 550 may include one or more kinetic, environmental, and/or kinematic sensors (e.g. temperature, humidity, barometric pressure, tilt, accelerometers, gyroscopes, magnetometers, etc.), coupled to the processor, in order to provide information about the state of the head 31 of the subject, and/or the surrounding environment during use to the processors 511*a,b*, 531*a,b*, 561*a,b*, a processor coupled thereto, or an associated algorithm, etc.

FIGS. 6*a*-6*d* show aspects of an HMD in accordance with the present disclosure. FIG. 6*a* illustrates aspects of a HMD in accordance with the present disclosure including a frame 601 for supporting one or more structures of the HMD, providing a harness for cabling, support for a coupled nasal bridge 613, etc. The HMD includes one or more visual input devices 603 (e.g. here shown as a flat display, an AMOLED display, a transparent display, a smart glass display, an electrochromatic film, etc.) coupled to the frames and coupled electrically 607*a* to a processor or microcircuit in accordance with the present disclosure. The HMD includes a back-facing imaging sensor 605 oriented so as to interface with a facial feature of the subject, the eye 41 of the subject, etc. during use, the back-facing imaging sensor 605 electrically coupled 607*b* to a processor or microcircuit in accordance with the present disclosure. The HMD includes a lens 611 (e.g. a corrective lens, an aspheric lens, etc.) coupled to the frame 601, optionally via a lens mounting bracket 609. The back-facing imaging sensor 605 may be arranged so as to interact with the eye 41 via the lens 611, so as to bypass the lens, etc. The field of view of the back-facing imaging sensor 605 may be adjusted to compensate for the presence of the lens 611 when interfacing with the subject. In aspects, an associated processor may be programmed with an algorithm to compensate for the presence of the lens 611 in the recorded signal from the imaging sensor 605, or in the visual input device 603. The processor may be configured to display a calibration image on the visual input device 603, the back-facing imaging sensor 605 configured to assess a reflection of the image on the lens 611, or on the face of the subject to generate a received calibration image, the processor or an algorithm related thereto configured to generate an image transformation based upon the calibration image and the received calibration image.

FIG. 6*b* illustrates aspects of a HMD in accordance with the present disclosure including a frame 621 for supporting one or more structures of the HMD, providing a harness for cabling, support for a coupled nasal bridge 629, etc. The HMD includes one or more visual input devices 623 (e.g. here shown as a curved display, a double curved display, an elliptical display, a display printed onto an eyeglass lens, a curved AMOLED display, a flexible AMOLED display, a transparent curved display, a smart glass display, an electrochromatic film, etc.) coupled to the frames and coupled electrically 627*a* to a processor or microcircuit in accordance with the present disclosure. The HMD includes a back-facing imaging sensor 625 oriented so as to interface with a facial feature of the subject, the eye 43 of the subject, etc. during use, the back-facing imaging sensor 625 electrically coupled 627*b* to a processor or microcircuit in accordance with the present disclosure. In aspects, an associated processor may be programmed with an algorithm to compensate for the location of one or more facial features on the subject, the position of the eye 43 of the subject with respect to the visual input device 623, the back-facing imaging sensor 625, etc. The processor may be configured to display a calibration image on the visual input device 623, the back-facing imaging sensor 625 configured to assess an impression of the calibration image on the face of the subject to generate a received calibration image, the processor or an algorithm related thereto configured to generate an image transformation based upon the calibration image and the received calibration image.

FIG. 6*c* illustrates aspects of a HMD in accordance with the present disclosure including a frame 641 for supporting one or more structures of the HMD, providing a harness for cabling, support for a coupled nasal bridge 649, etc. The HMD includes one or more visual input devices 643 (e.g. here shown as LED, a visible light LED, a broadband light source, one or more narrow band light sources, an IR light source, a UV light source, an IR LED, a light source array, an array of LEDs, one or more multicolor LEDs, an array of visible LEDs along with one or more near infrared or infrared LEDs, etc.) coupled to the frames and coupled electrically 647*a* to a processor or microcircuit in accordance with the present disclosure. The visual input device 643 may be configured so as to generate a light field, a visual display, a chromatic display, one or more visual cues (e.g. such as may be generated by blinking a light at a particular coordinate on the frame 641, by creating a pattern with the LEDs, etc.). The HMD includes a back-facing imaging sensor 645 and optionally a colorimetric sensor, each oriented so as to interface with a facial feature of the subject, the eye 45 of the subject, etc. during use, the back-facing imaging sensor 645 and/or colorimetric sensor electrically coupled 647*b* to a processor or microcircuit in accordance with the present disclosure. In aspects, an associated processor may be programmed with an algorithm to compensate for the location of one or more facial features on the subject, the position of the eye 45 of the subject with respect to the frame 641, one or more LEDs in the visual input device 643, the back-facing imaging sensor 645, etc. The processor may be configured to display a pattern with one or more LEDs in the visual input device 643, the back-facing imaging sensor 645 configured to assess an impression of the calibration image on the face of the subject to generate a received calibration image, the processor or an algorithm related thereto configured to generate an image transformation based upon the pattern and the received calibration image.

FIG. 6*d* illustrates aspects of a HMD in accordance with the present disclosure including a frame 661 for supporting one or more structures of the HMD, providing a harness for cabling, support for a coupled nasal bridge 669, etc. The HMD includes a plurality of back-facing imaging sensors 663*a-c* and optionally a colorimetric sensor, each oriented so as to interface with a facial feature of the subject, the eye 47 of the subject, etc. during use, the back-facing imaging sensors 663*a-c*, and/or colorimetric sensor electrically coupled 667 to a processor or microcircuit in accordance with the present disclosure. In aspects, an associated processor may be programmed with an algorithm to compensate for the location of one or more facial features on the subject, the position of the eye 47 of the subject with respect to the frame 661, or one or more of the back-facing imaging sensors 663a-c, etc. The processor may be configured to capture one or more calibration images from each of the back-facing imaging sensors 663a-c, configured to assess one or more regions of the face of the subject, an eye 47, an ocular region, a skin site, etc. optionally in a range of colors, wavelengths, etc. dependent upon the properties and positioning of each of the imaging sensors 663a-c. The processor or an algorithm related thereto configured to generate an image transformation, a facial map, a biometric, a procedural adjustment, or the like based upon the received calibration images.

FIG. 7 shows aspects of an eye 49 interacting with a visual input device 713 in accordance with the present disclosure. The eye 49 is shown oriented along an optical axis 701, the optical axis interfacing with the visual input device 713 at a point of interest 715 (e.g. a point on the visual input device 713 where a subject is looking at, etc.). Two additional light sources 717a,b, (e.g. pixels, LEDs, etc.), are shown on the surface of the visual input device 713, and light rays traced from the light sources 717a,b to corresponding sites 719a,b, on the retina of the eye 49 are shown. The Fovea 711 of the eye 49 and cornea 703 are also shown for reference. Such a configuration may be advantageous for assessing the function of the retina, as part of a multifocal retinogram, a retinogram, assessing function of the retina near to the Fovea 711, etc. In aspects, an HMD in accordance with the present disclosure may be advantageous for assessing the retina of an athlete before/after a competition, assessing traumatic brain injury of the subject, assessing stroke, assessing macular degeneration of a subject, assessing motor function of the eyes 49 of the subject, assessing the eye 49 for retinal detachment, etc. In aspects, the system may be configured so as to assess the visual response of a subject to a presentation, to visual cues, to assess retinal function against cues, etc. so as to assess function of one or more ocular components of the subject, etc.

FIGS. 8a-8b show aspects of the pupil and the iris of interest for inspection with a system in accordance with the present disclosure. FIG. 8a shows non-limiting representative examples of population norms for pupil diameters of subjects in light fields 801 and dark fields 803, in accordance with a predetermined stress test performed with a system in accordance with the present disclosure. A subject response to a stress test may be compared against one or more aspects of such a population norm, to determine if the subject is healthy, exhibits a particular disease state, is experiencing a particular emotional state, etc.

FIG. 8b illustrates a schematic of iris 810, 820, 840 state and deformation thereof during basic illustration of muscle movement therein during contraction and dilation of the pupil 812, 822, 842. The iris 810, 820, 840 includes a sphincter muscle 816, 826, 846 (primarily innervated by parasympthetically mediated nerves), nearer to the pupil 812, 822, 842, and a dilator muscle 814, 824, 844, (primarily innervated by sympathetically mediated nerves) located nearer to the sclera (not specifically shown). For purposes of discussion, features 818, 828, 848 on the sphincter muscle 816, 826, 846, are shown (features on the dilator muscle 814, 824, 844 are not shown so as to maintain clarity of the image). The iris 810 is shown with the pupil 812 in a substantially neutral diameter, features 818 of the sphincter muscle 816 spaced at a radial distance from the center of the pupil 812 or from the edge of the iris 810. The iris 820 is shown in a contracted state with the pupil 822 of a substantially small diameter, the movement between the neutral and contracted state, in this case, illustrated primarily by movement 832 of the sphincter muscle 826, the features 828 having moved radially and potentially circumferentially from their original position on the neutral iris 820. The iris 840 is shown in a substantially dilated state with the pupil 842 shown with a substantially large diameter, the movement between the neutral and contracted state, in this case, illustrated primarily by movement 852 of the dilator muscle 844, the features 848 having moved radially and potentially circumferentially from their original position on the neutral iris 820.

In aspects, the features 818, 828, 848, pupil diameter 812, 822, 842, interface between the sphincter muscle 816, 826, 846, and the dilator muscle 814, 824, 844 may vibrate, quiver, at a near microscopic scale due to movement, due to individual muscular unit responses from corresponding PNS and SNS innervation, etc. A strategically arranged imaging sensor in accordance with the present disclosure may be configured to capture images of such movement, an associated processor programmed so as to extract movement of features 818, 828, 848, boundaries, pupil diameter, pupil location with respect to the outer edge of the iris, eye lid position, blinking, etc. as part of an assessment, a response analysis to a stress test, to a procedure, a gaming session, a shopping session, an encounter, etc.

Figure 9A:
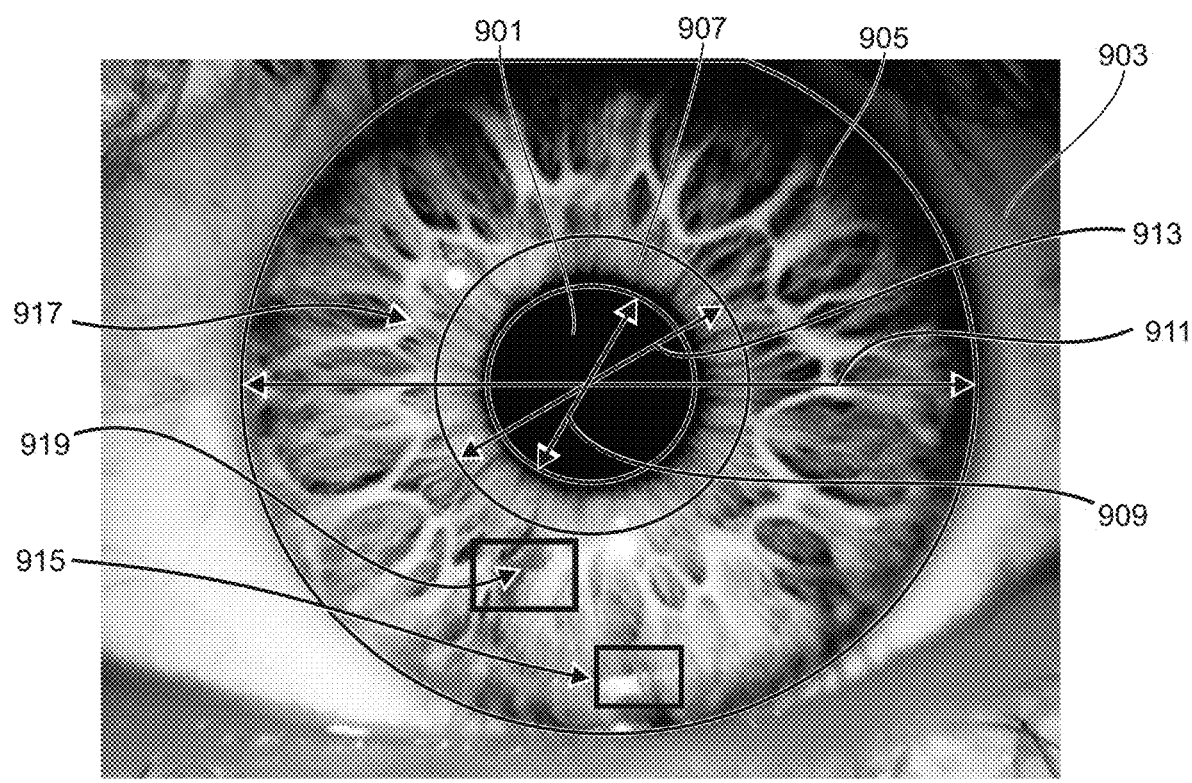
FIG. 9a-9e shows aspects of the iris and approaches to tracking features thereof in accordance with the present disclosure.

FIGS. 9a-9e shows aspects of the iris and approaches to tracking features thereof in accordance with the present disclosure. FIG. 9a shows an image of the iris 905 of a subject taken with a non-limiting example of an imaging sensor in accordance with the present disclosure (i.e. a high definition visible light with a tight field of view around the eye of the subject). The image was captured with sufficient detail so as highlight one or more features 901, 907, 905, 903, 915, 917, 919, 909, 911, 913 from the eye during a monitoring session thereof. Optionally, the imaging sensor may include an infrared or near infrared camera, etc. to capture the features 901, 907, 905, 903, 915, 917, 919, 909, 911, 913 (e.g. so as to improve contrast for individuals with dark colored irises, etc.). Some non-limiting examples of features 901, 907, 905, 903, 915, 917, 919, 909, 911, 913 shown include, the iris 905 or ciliary zone, pupil 901 and diameter thereof 909, sclera 903, sphincter muscle/pupillary zone 907 and diameter thereof 913, iris diameter 911, crypts 917 or peripheral crypts, contraction furrows 915, moles/iris freckles 919 or regions of alternative color, color distorted regions, regions of contrast, an identifiable region, etc. In aspects, a system in accordance with the present disclosure may be configured to adjust one or more components of the light field around the eye from image to image in order to accentuate one or more of the features 901, 907, 905, 903, 915, 917, 919, 909, 911, 913, assist in the tracking thereof, accentuate a high frequency microscopic motion thereof, etc. An associated processor or algorithm may be configured to track one or more of the features 901, 907, 905, 903, 915, 917, 919, 909, 911, 913, which may move radially out from the center of the iris 905, rotate around the center of the iris 905, jitter, move in response to neural signals thereto, translate in the frame of the images, etc. While not shown in color, it is to be noted that the image captured by the imaging sensor may be in color. For example, in FIG. 9a, iris freckle 919 may be a discolored mark (in this case brown) visibly noticeable against the iris 905, which may be blue or any other appropriate color or spectrum of colors. As another example, contraction furrow 915 may be an off-white color against the iris 905 (which may be blue or any other appropriate color).

Figure 9B:
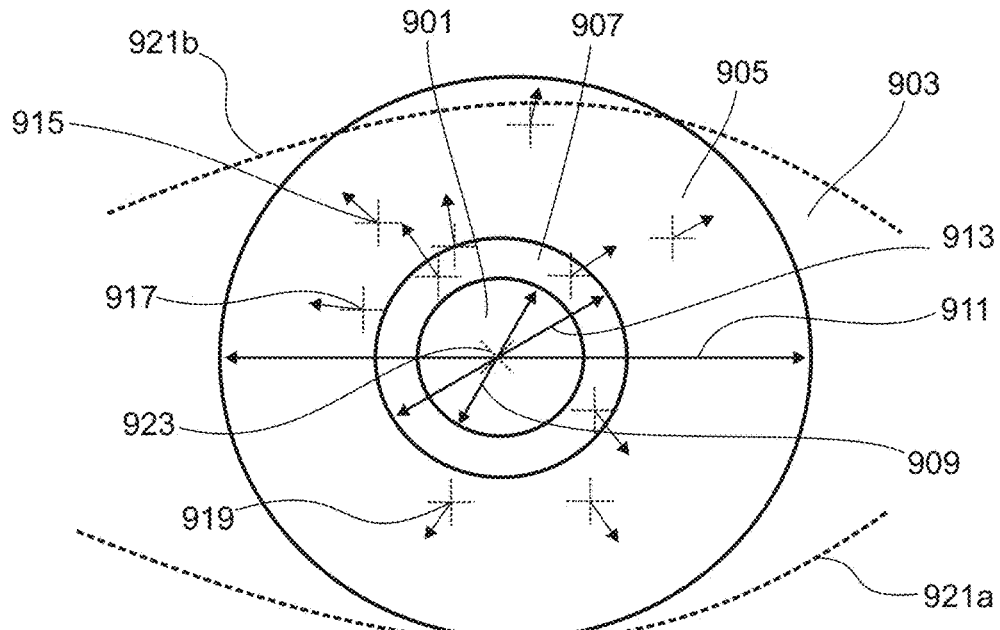

FIG. 9b shows an outline view of the iris 905 of a subject so as to highlight aspects of the feature tracking in more detail. The features shown include the iris 905 or ciliary zone, pupil 901 and diameter thereof 909, sclera 903, sphincter muscle/pupillary zone 907 and diameter thereof 913, iris diameter 911, crypts 917 or peripheral crypts, contraction furrows 915, moles 919 or regions of alternative color, color distorted regions, eye lid positions 921*a,b*, etc. In aspects, a system in accordance with the present disclosure may be configured to adjust one or more components of the light field around the eye from image to image in order to accentuate one or more of the features 901, 907, 905, 903, 915, 917, 919, 909, 911, 913, assist in the tracking thereof, accentuate a high frequency microscopic motion thereof, etc. An approximate center point 923 for the pupil 901 is shown, the center point 923 optionally usable in a differential tracking analysis of one or more of the features. Additional features, which may be tracked, are indicated with crosses. The movement (arrows) of the features, in this case during dilation of the pupil 901 are highlighted to illustrate radial but in some cases lateral movement of the features during movement of the muscles in the iris 905. The movement of such features may be collectively tracked so as to elucidate underlying muscular movement and neural activity associated therewith.

In aspects, the system may include an imaging sensor in the form of a camera (e.g. a visible light camera, a near infrared camera, an infrared camera, a combination thereof, or the like), the camera arranged so as to monitor one or more irises 905 of the subject, the camera configured such that the pixel count across the diameter of the iris 911 is more than 50 pixels, more than 100 pixels, more than 200 pixels, more than 400 pixels, or the like. In aspects, the camera is configured so as to take more than 10 images per second, more than 20 images per second, more than 40 images per second, more than 80 images per second, or the like. In aspects, a high frame-rate camera may be configured so as to track microscopic movements of features of the iris, associated with neuromuscular microscopic movements thereof.

Figure 9C:
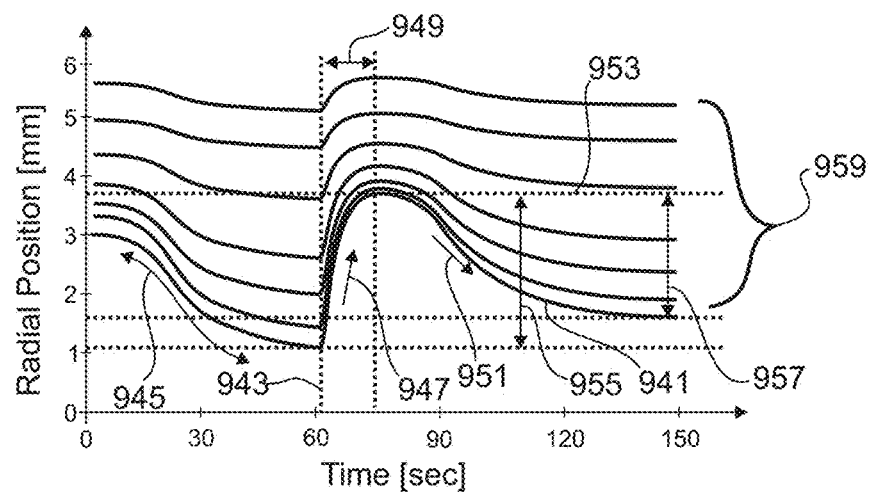

FIG. 9*c* shows a temporal plot of the radial position of several features with respect to the center point 923 of the pupil 901 during a baseline test 945, and after onset of a stress test 943 (of a duration 949) in accordance with the present disclosure. The feature positions 959 change along with the changing pupil diameter 941 on the temporal plot. Microscopic movements of the features are not indicated so as not to obscure clarity of the image but may be tracked with an imaging sensor in accordance with the present disclosure. Features of each movement such as latency of movement, maximal rate of dilation 947, maximum dilation 953, maximum rate of contraction 951, maximum change 955, recovery distance 957, may be considered in evaluating a disease state, a stress response, a procedural response, a patient selection process, an emotional response, a light reflex response, or the like in accordance with the present disclosure.

Figure 9D:
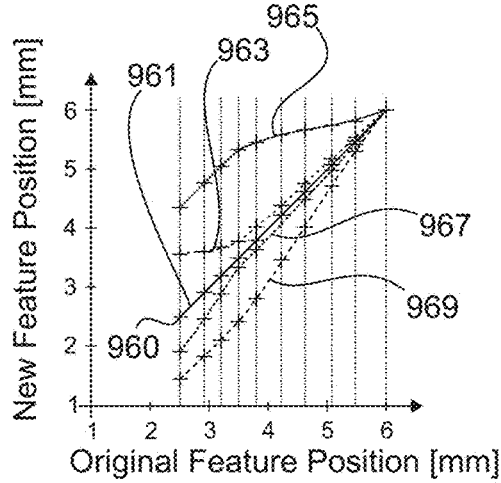

FIG. 9*d* illustrates feature movement during different examples of dilation and contraction of an iris. The original feature positions are shown along a first curve 961, the x-axis reflects the original position of the corresponding feature with respect to a pupil center point 923, and the y-axis reflects the present radial position of the same feature with respect to the present pupil center point 923. The inner most point 960 is representative of the pupil diameter. Two non-limiting examples of dilated responses 963, 965, and two non-limiting examples of contracted responses 967, 969 show some different examples of features moving during different kinds of dilation, contraction.

A first dilated response 963 is shown illustrating dilation of the pupil via primarily contraction of the sphincter muscle of the iris (e.g. such as via a decrease in the corresponding PNS outflow to the eye of the subject), while the dilator muscle did not substantially move during the first dilation response 963. A second dilation response 965 is shown wherein the dilation of the pupil occurred primarily via contraction of the dilator muscle (e.g. such as via increased SNS outflow to the eye of the subject), while the sphincter muscle did not substantially change during the dilation (in actual movement scenarios, the sphincter muscle will change slightly due to the relationship between changing circumference thereof as the pupil dilates).

A first contracted response 967 is shown illustrating contraction of the pupil via primarily expansion of the sphincter muscle of the iris (e.g. such as via an increase in the corresponding PNS outflow to the eye of the subject), while the dilator muscle did not substantially move during the first contraction response 967. A second contraction response 969 is shown wherein the contraction of the pupil occurred primarily via contraction of the dilator muscle (e.g. such as via decreased SNS outflow to the eye of the subject), while the sphincter muscle did not substantially change during the contraction (in actual movement scenarios, the sphincter muscle will change slightly due to the relationship between changing circumference thereof as the pupil dilates).

Such detailed analysis of the feature movement may be advantageous for independently determining the sphincter and dilator movements during a stress test (i.e. and for subsequent assessment of changes in the sympathetic nervous outflow and parasympathetic nervous outflow to the eyes of the subject).

In aspects, a relative movement between features may be converted into a metric in accordance with the present disclosure. Such movement may be transformed with a solid mechanic model of the iris movement to generate a corrected movement. This corrective calculation may be implemented so as to correct for the series mechanical interconnection of the sphincter and dilator muscles coupled to each other, and substantially anchored to the eye at the edge of the iris (i.e. at the interface between the iris and the sclera). Relative movements between one or more features located in the vicinity of the pupil may be representative of sphincter muscle related movement and subsequently related to PNS outflow to the eye, while relative movement between one or more features nearer to the edge of the iris may be representative of dilator muscle movement and subsequently related to SNS outflow to the eye. In aspects, a high speed, microscopic movement, and/or twitching of one or more features on the iris may be representative of individual or group firing nerves innervating the particular feature. Thus a substantially high frame rate assessment of the microscopic movement of one or more features may be representative of SNS or PNS neural activity to the eye.

Figure 9E:
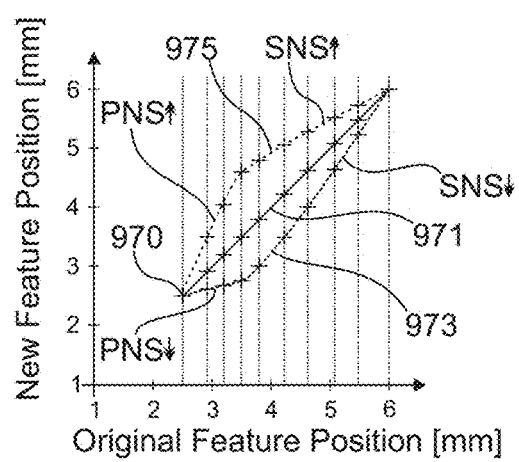

FIG. 9*e* illustrates feature movement during different examples of changes in the iris that substantially do not change the pupil diameter 970. The original feature positions are shown along a first curve 971, the x-axis reflects the original position of the corresponding feature with respect to a pupil center point 923, and the y-axis reflects the present radial position of the same feature with respect to the present pupil center point 923. The inner most point 970 is representative of the pupil diameter. In the first iris response curve 975, a combination of increasing SNS and increasing PNS activity has resulted in substantially no change in the pupil diameter 970, yet the features being tracked have substantially moved as evident from the first iris response curve 975. In the second iris response curve 973, a combination of decreasing SNS and decreasing PNS activity has resulted in substantially no change in the pupil diameter 970, yet the features being tracked have substantially moved as evident from the second iris response curve 973.

Figure 10A:
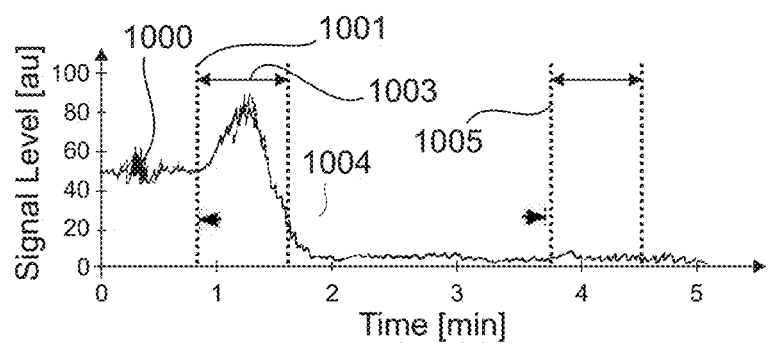
FIGS. 10a-10d illustrate temporal readings of metrics associated with stress testing and procedures in accordance with the present disclosure.

FIGS. 10a-10d illustrate temporal readings of metrics associated with stress testing and procedures in accordance with the present disclosure. FIG. 10a illustrates a time-signal graph of a metric derived from a neural activity signal 1000 or a surrogate thereof in accordance with the present disclosure as generated by one or more systems, devices, patches, patch/module pairs, an HMD, or the like. The signal 1000 may be derived from pupil movements, ocular feature movements, PNS/SNS related feature movements, facial EMG, ERG, EEG, perfusion, a skin SNA recording (e.g. derived from an absolute value thereof, from a pulse-per-second calculation, a filtered version thereof, from a pulse-per-minute calculation of a predetermined signal type, from a count of afferent signals per unit time, a count of efferent signals per unit time, a count of somatosensory nerve action potentials per unit time, SNS, PNS, a signal relating to vasodilation, vasoconstriction, local blood perfusion, sweat, hydration, etc.). The graph shows a first procedure 1001 in accordance with the present disclosure being applied to one or more sites on or within the body of the subject (e.g. a stress test, a nerve block, an ablation procedure, a neuromodulation procedure, etc.), for a first period of time 1003, the signal 1000 demonstrating an initial increase in activity and then an overall decrease in activity over a time period following the first procedure 1001. After a delay 1004, a second procedure 1005 is applied to one or more sites on or within the body of the subject. Following this second procedure 1005 the signal 1000 does not substantially change, thus indicating that the first procedure 1001 affected the ANS in a manner that was substantially durable over the timeframe considered.

Figure 10B:
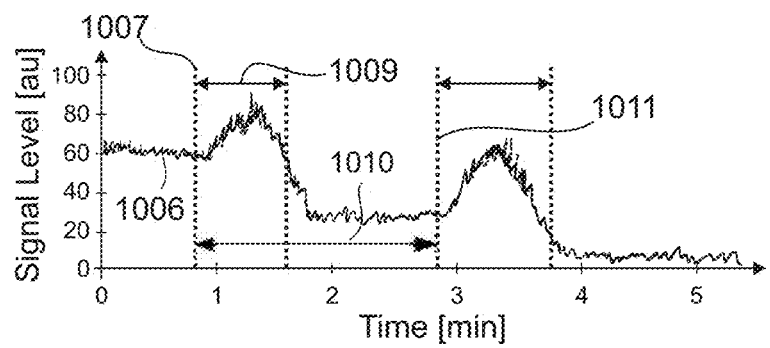

FIG. 10b illustrates a time-signal graph of a metric derived from a neural activity signal 1006 in accordance with the present disclosure as generated by one or more systems, devices, patches, patch/module pairs, HMD, or the like. The signal 1006 may be derived from pupil movements, ocular feature movements, PNS/SNS related feature movements, facial EMG, ERG, EEG, perfusion, a skin SNA recording (e.g. derived from an absolute value thereof, from a pulse-per-second calculation, a filtered version thereof, from a pulse-per-minute calculation of a predetermined signal type, from a count of afferent signals per unit time, a count of efferent signals per unit time, a count of somatosensory nerve action potentials per unit time, SNS, PNS, a signal relating to vasodilation, vasoconstriction, local blood perfusion, sweat, hydration, etc.), or the like each in accordance with the present disclosure. The graph shows a first procedure 1007 in accordance with the present disclosure being applied to one or more sites on or within the body of the subject (e.g. a stress test, a nerve block, an ablation procedure, a neuromodulation procedure, etc.), for a first period of time 1009, the signal 1006 demonstrating an initial increase in activity and then an overall decrease in activity over a time period following the first procedure 1007. After a delay 1010, a second procedure 1011 is applied to one or more sites on or within the body of the subject. Following this second procedure 1011 the signal 1006 substantially changes again, demonstrating that the first procedure 1007 did not significantly affect the ANS of the subject in a manner that was substantially durable over the timeframe considered. A third procedure of higher dosage, longer duration, etc. may be attempted to form a durable procedure if that is the desired affect for the given example.

Figure 10C:
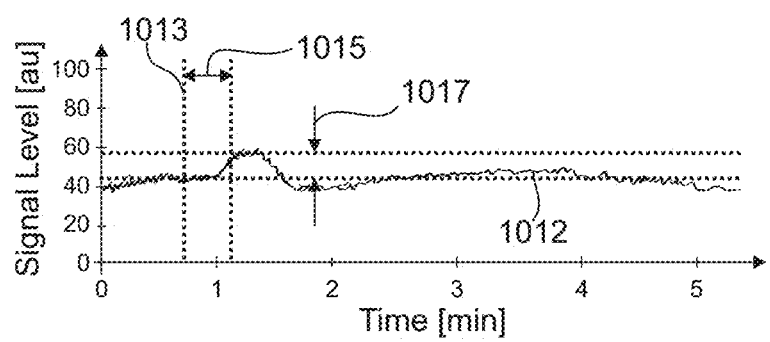

FIG. 10c illustrates a time-signal graph of a metric derived from a neural activity signal 1012 in accordance with the present disclosure as generated by one or more systems, devices, patches, patch/module pairs, an HMD, or the like. The signal 1012 may be derived from pupil movements, ocular feature movements, PNS/SNS related feature movements, facial EMG, ERG, EEG, perfusion, skin SNA recording (e.g. derived from an absolute value thereof, from a pulse-per-second calculation, a filtered version thereof, from a pulse-per-minute calculation of a predetermined signal type, from a count of afferent signals per unit time, a count of efferent signals per unit time, a count of somatosensory nerve action potentials per unit time, SNS, PNS, a signal relating to vasodilation, vasoconstriction, local blood perfusion, sweat, hydration, etc.), or the like each in accordance with the present disclosure. The graph shows a first stress test 1013 in accordance with the present disclosure being applied to one or more sites on or within the body of the subject (e.g. a stress test, delivery of a medication, local administration of a chemical specie, consumption of a drug, questioning the subject, stimulating one or more sites on the subject's body, presenting a visual and/or auditory input to the subject, etc.), for a first period of time 1015, the signal 1012 demonstrating a small change in signal level 1017 over a monitoring period following application of the first stress test 1013. After completion of the monitoring period, one or more additional stress tests may be performed on the subject so as to gauge other metrics, ANS relationships, to generate dose response relationships, etc. In this non-limiting example, the signal 1012 did not change substantially during the monitoring period. Such small changes may indicate that the subject is not a suitable candidate for a procedure, the subject's ANS or the aspect monitored thereof is not substantially influenced by the stress test 1013, etc.

Figure 10D:
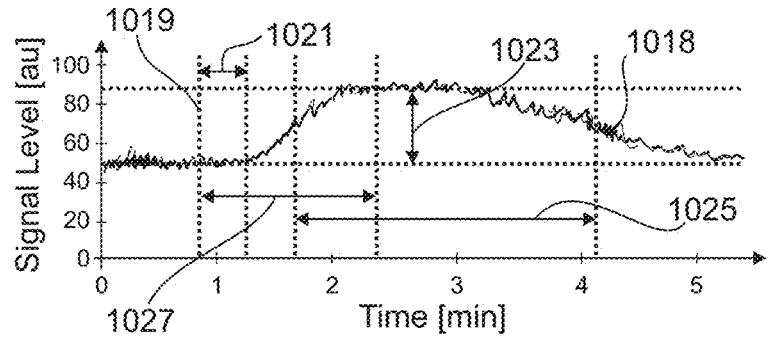

FIG. 10d illustrates a time-signal graph of a metric derived from a neural activity signal 1018 in accordance with the present disclosure as generated by one or more systems, devices, patches, patch/module pairs, an HMD, or the like. The signal 1018 may be derived from pupil movements, ocular feature movements, PNS/SNS related feature movements, facial EMG, ERG, EEG, perfusion, skin SNA recording (e.g. derived from an absolute value thereof, from a pulse-per-second calculation, a filtered version thereof, from a pulse-per-minute calculation of a predetermined signal type, from a count of afferent signals per unit time, a count of efferent signals per unit time, a count of somatosensory nerve action potentials per unit time, SNS, PNS, a signal relating to vasodilation, vasoconstriction, local blood perfusion, sweat, hydration, etc.), or the like each in accordance with the present disclosure. The graph shows a first stress test 1019 in accordance with the present disclosure being applied to one or more sites on or within the body of the subject (e.g. a stress test, delivery of a medication, local administration of a chemical specie, consumption of a drug, questioning the subject, stimulating one or more sites on the subject's body, presenting a visual and/or auditory input to the subject, etc.), for a first period of time 1021, the signal 1018 demonstrating a strong change in response to the stress test 1019. The signal 1018 begins to change after a short delay, the change continues towards a maximum value within a first timeframe 1027, the maximum change in value being registered 1023, and then recovering back to substantially the resting value over a second timeframe 1025 (herein shown the time between half the maximum change on the up-wing and the down-swing of the signal change). The timeframes 1027, 1025, the maximum change 1023, comparison with other stress tests, other response metrics, or the like, may be advantageous in determining if the subject is a suitable candidate for a procedure, a medical procedure, if the subject has a particular disease state, the extent of the disease state, that subject's ANS or the aspect monitored thereof is substantially influenced by the stress test 1019, etc.

In aspects, a method in accordance with the present disclosure may include applying a medicament to each eye of the subject. A first medicament meant to alter the SNS innervated muscle activity of the first eye (i.e. to alter, block, and/or saturate the SNS innervated muscle activity in the dilator muscle of the first eye, etc.), and a second medicament meant to alter the PNS innervated muscle activity of the second eye (i.e. so as to alter, block, and/or saturate the PNS innervated muscle activity of the sphincter muscle in the second eye, etc.). In aspects, a topical dosage of an anticholinergic agent, atropine, hyoscyamine, scopolamine, tropicamide or an equivalent may be suitable to inhibit PNS activity on the second eye, PNS saturation may be induced by a dosage of a muscarinic receptor agonist, a choline, acetylcholine, carbachol, methacholine, bethanechol, muscarine, nicotine, pilocarpine, oxotremorine, or an equivalent. In aspects, a topical dosage of an alpha blocker, an alpha-1 blocker, an alpha andrenergic blocker, thymoxamine, doxazosin, silodosin, prazosin, tamsulosin, alfuzosin, terazosin, trimazosin, phenoxybenzamine, phentolamine, or the like to inhibit SNS related activity of the dilator muscle in the first eye. In aspects, SNS saturation may be induced by a dosage of an alpha agonist, alpha adrenergic agonist, methyldopa, an alpha-1 agonist, a sympathomimetic agent, p-hydroxyamphetamine, methoxamine, methylnorepinephrine, midodrine, oxymetazoline, metaraminol, phenylephrine, epinephrine, or the like.

Such a configuration may be advantageous for independently assessing the SNS outflow to the first eye, and the PNS outflow to the second eye, during a stress test, a procedure, a patient selection protocol, a gaming experience, etc. Independent assessment of the PNS and SNS outflow as measured differentially between the eyes of the subject may be advantageous to determine the effect of a procedure, a neuromodulation, a stress test, etc. on the overall PNS and SNS outflow in the subject.

In aspects, alternatively, the PNS in one eye may be saturated and/or inhibited by application of an appropriate agent, the SNS activity in the second eye may be saturated and/or inhibited, such that a differential SNS, PNS response may be assessed independently by watching one or more features (e.g. pupil diameter, iris features, etc.) on the eyes during a stress test, etc.

In aspects, one or more visual input devices may be coupled to a control circuit, a microcircuit, a processor, etc. configured to induce a flicker, a rotating illuminated field, a sequential excitation of light sources, a changing glare on a facial feature, etc. of the subject during a test.

In aspects, a stress test may include assessing one or more hemodynamic changes (e.g. BP, HR, HR variability) in the subject in relation to one or more autonomic neural activities (e.g. pupillary changes, iris feature changes, piloerection, sweating, skin neural activity, etc.) during a stimulation and/or blockade based stress test, procedure, renal nerve block, renal nerve stimulation, etc. Such monitoring may be to establish one or more relationships between the blockade, stimulation and a hemodynamic and/or autonomic neural outflow change in the subject. In aspects, a stress test may include application of an SNS specific blockade (e.g. a beta-1 for SNS on the juxtaglomerular apparatus), or the like, so as to monitor if there is more or less of a substantive blunting of one or more related autonomic activities (e.g. SNS activity, PNS activity, and/or surrogates thereof). Such a procedure may be advantageous for assessing if the renin-angiotensin-aldosterone sensitivity of a subject may be responsive to a renal denervation procedure. If an unsubstantial response is elicited, in one or more related parameters such as BP/HR/HRV/ANS outflow in response to a pharmacologic specific blockade, it would then suggest that the subject may not be responsive to a renal denervation procedure for the treatment of hypertension.

Stimulation of one or more neural structures, nerves, ganglia, etc. in the body may be stimulated by one or more energy delivery and/or chemical delivery tools in accordance with the present disclosure. Some non-limiting examples include inducing focal nerve stimulation, a focal renal nerve stimulation, etc. with a low intensity focused ultrasound, a low level heating, a chemical delivery, an electrical stimulation, etc.

In aspects, a procedure, a stress test, a calibration procedure, a baseline test, or the like may include administering a audio/visual presentation to the subject, the presentation including one or more automated lighting patterns, automated light intensity changes, color changes, flash, flicker, light field, dark field, multi-color lighting field, etc. so as to assess a dose response, light reflex, or the like of an ocular feature, a pupil diameter, change or movement of an iris feature, an iris sphincter muscle movement, a iris dilator muscle movement, etc. Response to such a presentation may be used to establish a baseline response to the physiologic parameters under measurement, a light-dark response, a retinogram, a combination thereof, or the like.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A system for monitoring a subject, comprising:
a head mounted display configured and sized for placement onto a head of the subject, the head mounted display comprising a visual input device and a back-facing imaging sensor;
the visual input device arranged within a field of view of the subject when the head mounted display is coupled to the head of the subject, the visual input device being configured to display one or more output images for the subject;
the back-facing imaging sensor arranged with the field of view of the subject and covering one or more facial features of the subject when the head mounted display is coupled to the head of the subject, the back-facing imaging sensor being configured to generate one or more feedback images of the subject; and
a processor at least one of electrically coupled and wirelessly coupled to the visual input device and the back-facing imaging sensor, the processor being configured:
to deliver the one or output images to the visual input device;
to accept the one or more feedback images;

to analyze the one or more feedback images to identify sphincter muscle related movement and dilator muscle related movement of one or more features of one or more eyes of the subject; and to generate one or more metrics related to at least one of parasympathetic nervous system (PNS) and sympathetic nervous system (SNS) outflow to the one or more eyes of the subject based at least in part on the identified sphincter muscle related movement and dilator muscle related movement of the one or more features of the one or more eyes of the subject.

2. The system in accordance with claim 1, wherein the head mounted display comprises a shroud, the shroud arranged so as to isolate the one or more eyes of the subject from a surrounding environment, when the head mounted display is coupled to the head of the subject.

3. The system in accordance with claim 2, wherein the shroud comprises at least one of one or more sensors and one or more electrodes, said at least one of the one or more sensors the one or more electrodes being arranged along the shroud so as to bias against one or more skin sites of the subject when the head mounted display is coupled to the head of the subject, and wherein the processor is coupled to said at least one of the one or more sensors the one or more electrodes.

4. The system in accordance with claim 3, wherein the one or more electrodes are arranged along the shroud so as to capture, in conjunction with the processor, at least one of an electroretinogram, an electrooculogram, an electroencephalogram, and an electromyogram from the subject.

5. The system in accordance with claim 1, wherein the visual input device is configured to alter a light field near to at least one of the one or more facial features via at least one of the one or more output images, the back-facing imaging sensor being configured to capture one or more aspects of the light field in at least one of the one or more feedback images.

6. The system in accordance with claim 5, wherein the altered light field occurs over an optical spectrum without substantially impacting a light reflex of the one or more eyes of the subject.

7. The system in accordance with claim 1, wherein at least one of the one or more of the facial features is an iris of a given one of the one or more eyes of the subject, the back-facing imaging sensor configured to image the iris with a pixel count across a diameter of the iris of more than 50 pixels, the processor being configured to track one or more features of the iris.

8. The system in accordance with claim 1, wherein the back-facing imaging sensor is configured to take more than 10 images per second.

9. The system in accordance with claim 7, wherein the one or more of the features of the iris comprise at least one of a ciliary zone, a pupil, a sphincter muscle/pupillary zone, a crypt, a peripheral crypt, a contraction furrow, a mole, a region of alternative/distinct color, a color distorted region, a region of contrast, an identifiable region, a diameter, boundary, centroid, area, and distortion.

10. The system in accordance with claim 1, wherein the visual input device comprises at least one of a display, a light emitting diode (LED), a visible light LED, a broadband light source, one or more narrow band light sources, an infrared (IR) light source, an ultraviolet (UV) light source, an IR LED, a light source array, a curved display, an active-matrix organic light-emitting diode (AMOLED) display, a flexible AMOLED display, a transparent display, a smart glass display, and an electrochromatic film.

11. The system in accordance with claim 1, wherein the visual input device comprises a semi-transparent display.

12. The system in accordance with claim 1, wherein the back-facing imaging sensor comprises at least one of a camera, a visible light camera, a near infrared camera, an infrared camera, short wavelength infrared camera, a complementary metal-oxide-semiconductor (CMOS) imaging sensor, an infrared imaging sensor, a laser speckle imaging sensor, and a coherence tomographic imaging element.

13. The system in accordance with claim 1, wherein the head mounted display comprises at least one of a plurality of visual feedback devices and a plurality of back-facing imaging sensors.

14. The system in accordance with claim 1, wherein the head mounted display comprises one or more audio input devices, arranged so as to interface with one or more ears of the subject when the head mounted display is coupled to the head of the subject, the one or more audio input devices being coupled to the processor, the one or more audio input devices being configured to render an audio stream provided by the processor.

15. The system in accordance with claim 1, wherein the head mounted display comprises one or more optical sensors arranged so as to bias against one or more skin sites of the subject when the head mounted display is coupled to the head of the subject, the processor being coupled to the one or more optical sensors to receive at least one of one or more hemodynamic signals and one or more tissue analyte signals.

16. The system in accordance with claim 15, wherein at least one of the one or more optical sensors is at least one of integrated into a shroud, integrated into one or more audio input devices, and arranged so as to interface with at least one of a nose, a nasal bridge, a temple region, an ocular region, an ear, an earlobe, and an ear canal of the subject.

17. The system in accordance with claim 1, further comprising one or more physiologic sensors coupled to a body of the subject, the one or more physiologic sensors being configured to produce one or more physiologic signals, wherein at least one of the one or more physiologic sensors is configured for wireless communication with the processor to provide the one or more physiologic signals to the processor.

18. The system in accordance with claim 17, wherein at least one of the one or more physiologic sensors comprises an electrophysiologic sensor, a heart-rate sensor, a skin neural activity sensor, a temperature sensor, a thermal gradient sensor, a barometer, an altimeter, an accelerometer, a gyroscope, a humidity sensor, a magnetometer, an inclinometer, an oximeter, a colorimetric monitor, a perfusion sensor, a sweat analyte sensor, a galvanic skin response sensor, an interfacial pressure sensor, a flow sensor, a stretch sensor, and a microphone.

19. The system in accordance with claim 18, wherein at least one of the one or more physiologic sensors is arranged for placement onto at least one of a perineal region of the subject, a perianal region of the subject, a pubic region of the subject, an inner thigh region of the subject, a posterior knee region of the subject, a neck of the subject, an ear of the subject, an ocular region of the subject, a breast of the subject, an axilla of the subject, an elbow of the subject, a wrist of the subject, a palm of the subject, a foot of the subject, a lip of the subject, and an erogenous zone of the subject.

20. The system in accordance with claim 1, further comprising a stimulating device arranged so as to interface with skin of the subject, wherein the stimulating device comprises at least one of an electrical stimulator, a thermo-regulating device, a heating coil, a thermoelectric device, a Peltier device, a tactile stimulating component, and a vibratory stimulating element.

* * * * *